(12) United States Patent
Kompala

(10) Patent No.: US 10,596,492 B2
(45) Date of Patent: *Mar. 24, 2020

(54) PARTICLE SETTLING DEVICES

(71) Applicant: SUDHIN BIOPHARMA, Superior, CO (US)

(72) Inventor: Dhinakar S. Kompala, Superior, CO (US)

(73) Assignee: SUDHIN BIOPHARMA, Superior, CO (US)

(*) Notice: Subject to any disclaimer, the term of this patent is extended or adjusted under 35 U.S.C. 154(b) by 356 days.

This patent is subject to a terminal disclaimer.

(21) Appl. No.: 15/586,902

(22) Filed: May 4, 2017

(65) Prior Publication Data

US 2017/0333815 A1 Nov. 23, 2017

Related U.S. Application Data

(63) Continuation-in-part of application No. 15/324,062, filed as application No. PCT/US2015/039723 on Jul.
(Continued)

(51) Int. Cl.
  *B01D 21/26* (2006.01)
  *B01J 8/00* (2006.01)
  (Continued)

(52) U.S. Cl.
  CPC ....... *B01D 21/265* (2013.01); *B01D 21/0045* (2013.01); *B01J 8/007* (2013.01);
  (Continued)

(58) Field of Classification Search
  CPC .............. B01D 21/265; B01D 21/0045; B01D 17/0211; B01D 17/0214; B01D 17/0217;
  (Continued)

(56) References Cited

U.S. PATENT DOCUMENTS 1,602,935 A * 10/1926 Rasey ................ B01D 17/0211
                                                        210/223
1,701,068 A    2/1929 Flowers
(Continued)

FOREIGN PATENT DOCUMENTS

DE        4438510         4/1996
EP         521583    *   7/1993   ........... B01D 17/028
(Continued)

OTHER PUBLICATIONS

International Preliminary Report on Patentability for International (PCT) Patent Application No. PCT/US15/39723, dated Jan. 10, 2017, 10 pages.
(Continued)

*Primary Examiner* — Joseph W Drodge
(74) *Attorney, Agent, or Firm* — Sheridan Ross PC

(57) ABSTRACT

The present disclosure relates to settling devices for separating particles from a bulk fluid with applications in numerous fields. The particle settling devices of the present disclosure may include a stack of truncoconical cones that may be arranged in opposite orientation, apex to base. Other embodiments include several concentric vertical tubes attached to conical surfaces at the bottom, with inclined settling strips attached to the vertical tubes in annular regions between the tubes. These devices are useful for separating small (millimeter or micron sized) particles from a bulk fluid with applications in numerous fields, such as biological (microbial, mammalian, plant, insect or algal) cell cultures, solid catalyst particle separation from a liquid or gas and waste water treatment.

27 Claims, 24 Drawing Sheets

Related U.S. Application Data 9, 2015, now abandoned, application No. 15/586,902, which is a continuation-in-part of application No. PCT/US2015/063195, filed on Dec. 1, 2015.

(60) Provisional application No. 62/086,122, filed on Dec. 1, 2014, provisional application No. 62/332,546, filed on May 6, 2016, provisional application No. 62/459,509, filed on Feb. 15, 2017, provisional application No. 62/022,276, filed on Jul. 9, 2014, provisional application No. 62/037,513, filed on Aug. 14, 2014.

(51) Int. Cl.
| | |
|---|---|
| *C07K 1/22* | (2006.01) |
| *B01D 21/00* | (2006.01) |
| *B04C 5/10* | (2006.01) |
| *C02F 1/38* | (2006.01) |
| *C07K 1/14* | (2006.01) |
| *C07K 16/00* | (2006.01) |
| *C12N 1/02* | (2006.01) |
| *C12N 1/12* | (2006.01) |
| *C12N 1/16* | (2006.01) |
| *C12N 5/04* | (2006.01) |
| *C12N 7/00* | (2006.01) |
| *C12Q 3/00* | (2006.01) |
| *C12M 1/00* | (2006.01) |
| *B04C 5/103* | (2006.01) |
| *C12M 1/26* | (2006.01) |
| *C12M 1/34* | (2006.01) |
| *C12N 5/0783* | (2010.01) |
| *C12N 5/078* | (2010.01) |
| *C12N 5/0775* | (2010.01) |
| *C02F 103/34* | (2006.01) |

(52) U.S. Cl.
CPC ............ *B01J 8/0055* (2013.01); *B04C 5/103* (2013.01); *C02F 1/38* (2013.01); *C07K 1/14* (2013.01); *C07K 1/22* (2013.01); *C07K 16/00* (2013.01); *C12M 29/10* (2013.01); *C12M 33/22* (2013.01); *C12M 41/00* (2013.01); *C12M 47/02* (2013.01); *C12M 47/10* (2013.01); *C12N 1/02* (2013.01); *C12N 1/12* (2013.01); *C12N 1/16* (2013.01); *C12N 5/04* (2013.01); *C12N 5/0636* (2013.01); *C12N 5/0644* (2013.01); *C12N 5/0662* (2013.01); *C12N 7/00* (2013.01); *C12Q 3/00* (2013.01); *B01J 2208/00761* (2013.01); *C02F 2103/34* (2013.01); *Y02W 10/37* (2015.05)

(58) Field of Classification Search
CPC ............ B01D 21/0039; B01D 21/0048; B01D 21/0069; B01D 21/26; B01D 21/267; B01D 21/30; B01D 21/305; B01D 21/32; C12M 47/10; C12M 33/22; C12M 29/10; C12M 41/00; C12M 47/02; C12M 33/10; C12M 45/05; C12M 47/04; C12M 47/12; B04C 5/103; B04C 3/00; B04C 3/04; B04C 9/00; B04C 11/00; B04C 2009/004; C07K 1/22; C07K 1/14; C07K 16/00; C02F 1/38; C02F 2103/34; C02F 1/385; C02F 2101/30; C02F 2103/32; C02F 2103/343; B01J 2208/00761; B01J 8/0055; B01J 8/007; C12N 5/0636; C12N 5/04; C12N 7/00; C12N 1/02; C12N 5/0662; C12N 5/0644; C12N 1/16; C12N 1/12; C12Q 3/00; Y02W 10/37

USPC ....... 210/739, 742, 743, 745, 787, 788, 800, 210/804, 85, 94, 96.1, 143, 149, 512.1, 210/512.2, 512.3, 522

See application file for complete search history.

(56) References Cited

U.S. PATENT DOCUMENTS

| | | | | |
|---|---|---|---|---|
| 2,230,386 | A * | 2/1941 | Pecker | B01D 21/0018 210/521 |
| 2,261,101 | A * | 10/1941 | Erwin | E21B 43/34 126/355.1 |
| 2,307,154 | A * | 1/1943 | Osuna | B01D 21/0003 127/13 |
| 2,651,415 | A * | 9/1953 | Worthen | B01D 17/0211 210/93 |
| 3,718,257 | A * | 2/1973 | Bach | B01D 21/0024 210/802 |
| 3,960,734 | A | 6/1976 | Zagorski | |
| 4,048,069 | A | 9/1977 | Cuvillier et al. | |
| 4,151,084 | A | 4/1979 | Probstein | |
| 4,859,347 | A * | 8/1989 | Simon | B01D 17/0217 210/788 |
| 4,939,087 | A * | 7/1990 | Van Wie | B04B 5/0442 210/651 |
| 5,401,404 | A * | 3/1995 | Strauss | B01D 17/0208 210/265 |
| 5,624,580 | A | 4/1997 | De Hoxar | |
| 5,817,505 | A | 10/1998 | Thompson et al. | |
| 5,840,198 | A * | 11/1998 | Clarke | B01D 17/0211 210/802 |
| 5,904,855 | A * | 5/1999 | Manz | B01D 21/0003 210/709 |
| 5,948,271 | A * | 9/1999 | Wardwell | B04B 1/20 210/143 |
| 6,133,019 | A * | 10/2000 | Herman | C12M 27/10 435/286.1 |
| 6,146,891 | A * | 11/2000 | Condon | C12N 5/0075 435/235.1 |
| 6,720,358 | B2 | 4/2004 | Espinoza et al. | |
| 7,078,439 | B2 | 7/2006 | Odueyungbo et al. | |
| 7,431,846 | B2 | 10/2008 | Palmer | |
| 7,931,445 | B2 * | 4/2011 | Haans | F03D 1/0608 416/1 |
| 8,216,854 | B2 | 7/2012 | Ballerstadt et al. | |
| 8,728,318 | B2 * | 5/2014 | Vellinga | B01D 21/0045 210/188 |
| 2003/0136729 | A1* | 7/2003 | Batson | B01D 17/0211 210/512.1 |
| 2005/0194316 | A1* | 9/2005 | Pourahmadi | B01L 3/502715 210/638 |
| 2005/0194322 | A1 | 9/2005 | Palmer | |
| 2006/0032486 | A1 | 2/2006 | Prasad | |
| 2007/0246431 | A1* | 10/2007 | Palmer | B01D 21/0045 210/715 |
| 2009/0159523 | A1 | 6/2009 | McCutchen | |
| 2011/0097800 | A1 | 4/2011 | Kauling et al. | |
| 2012/0180662 | A1 | 7/2012 | Missalla et al. | |
| 2013/0052105 | A1 | 2/2013 | Butler | |
| 2013/0272943 | A1* | 10/2013 | Braga | B01D 53/00 423/242.2 |
| 2014/0011270 | A1 | 1/2014 | Chotteau et al. | |
| 2014/0044696 | A1 | 2/2014 | Bamdad | |
| 2014/0225286 | A1 | 8/2014 | Paxton | |
| 2017/0090490 | A1* | 3/2017 | Mills | G05B 19/41865 |

FOREIGN PATENT DOCUMENTS

| | | |
|---|---|---|
| GB | 105318 | 4/1917 |
| RU | 2182508 | 5/2002 |

(56) References Cited

FOREIGN PATENT DOCUMENTS

| WO | WO 91/06627 | 5/1991 |
|---|---|---|
| WO | WO 2016/007730 | 1/2016 |

OTHER PUBLICATIONS

International Preliminary Report on Patentability for International (PCT) Patent Application No. PCT/US15/63195, dated Jun. 6, 2017, 9 pages.
International Search Report and Written Opinion for International (PCT) Patent Application No. PCT/US17/31252, dated Jul. 20, 2017, 8 pages.
U.S. Appl. No. 15/324,062, filed Jan. 5, 2017, Kompala.
Batt et al., "Inclined Sedimentation for Selective Retention of Viable Hybridomas in a Continuous Suspension Bioreactor," Biotechnology Progress, 1990, vol. 6, pp. 458-464, abstract only, 3 page.
Boycott, "Sedimentation of Blood Corpuscles," Nature, 1920, vol. 104(2621), pp. 532, abstract only, 1 page.
Brennan et al., "A perfusion system for antibody production by shear-sensitive hybridoma cells in a stirred reactor," Biotechnol. Techniques, 1987, vol. 1(3), pp. 169-174, abstract only, 5 pages.
Bungay et al., "Cross-Flow Lamellar Settlers for Microbial Cells," Biotechnology and Bioengineering, 1984, vol. 26, pp. 640-641.
Cilliers et al., "The application of mini-gydrocyclones in the concentration of yeast suspensions," Chemical Engineering Journal, 1997, vol. 65(1), pp. 21-26, abstract only, 2 pages.
Elsayed et al., "Use of Hydrocyclones for Mammalian Cell Retention: Separation Efficiency and Cell Viability (Part 1)," Eng. Life Sci., 2006, vol. 6(4), pp. 347-354.
Geiler, et al., "Genetically Engineered in Vitro Erythropoiesis," International Journal of Stem Cells, 2016, vol. 9(1), pp. 53-59.
Gorenflo et al., "Optimization of an Acoustic Cell Filter with a Novel Air-Backflush System," Biotechnology Progress, 2003, vol. 19, pp. 30-36, abstract only, 2 pages.
Himmelfarb et al., "Spin Filter Culture: The Propagation of Mammalian Cells in Suspension" Science, 1969, vol. 164(3879), pp. 555-557, abstract only, 1 page.
Johnson et al., "Use of the Centritech Lab Centrifuge for Perfusion Culture of Hybridoma Cells in Protein-Free Medium," Biotechnology Progress, 1999, vol. 12, pp. 855-864, abstract only, 1 page.
Kitano et al., "Production of human monoclonal antibodies by heterohybridomas," Applied Microbiology and Biotechnology, 1986, vol. 24(4), pp. 282-286, abstract only, 1 page.
Knazek et al., "Cell culture on artificial capillaries: an approach to tissue growth in vitro," 1972, vol. 178(4056), pp. 65-66, abstract only, 1 page.
Panuganti et al., "Three-Stage Ex Vivo Expansion of High-Ploidy Megakaryocytic Cells: Toward Large-Scale Platelet Production," Tissue Engineering Part A, 2013, vol. 19(7&8), pp. 998-1014.
Searles et al., "Viable Cell Recycle with an Inclined Settler in the Perfusion Culture of Suspended Recombinant Chinese Hamster Ovary Cells," Biotechnology Progress, 1994, vol. 10(2), pp. 198-206, abstract only, 1 page.
Yuan et al., "An Investigation into the Possible Use of Hydrocyclones for the Removal of Yeast from Beer," Bioseparation, 1996, vol. 6, pp. 159-163, abstract only, 1 page.
International Search Report and Written Opinion for International (PCT) Patent Application No. PCT/US15/39723, dated Dec. 1, 2015, 14 pages.
International Search Report and Written Opinion for International (PCT) Patent Application No. PCT/US15/63195, dated Feb. 12, 2016, 12 pages.
International Search Report and Written Opinion for International (PCT) Patent Application No. PCT/US19/25884, dated Jul. 30, 2019 10 pages.
Official Action for U.S. Appl. No. 16/099,248, dated Jul. 10, 2019 17 pages.
Official Action for U.S. Appl. No. 16/375,683, dated Jul. 9, 2019 21 pages.
Notice of Allowance for U.S. Appl. No. 16/375,683, dated Oct. 24, 2019, 11 pages.

\* cited by examiner

PARTICLE SETTLING DEVICES

CROSS REFERENCE TO RELATED APPLICATION

This application is a continuation in part of U.S. patent application Ser. No. 15/324,062, filed Jan. 5, 2017, a continuation in part of PCT Application No. PCT/US2015/1063195 having an international filing date of Dec. 1, 2015 and which designated the United States, and also claims priority under 35 U.S.C. § 119(e) to U.S. Provisional Patent Application No. 62/332,546, filed May 6, 2016, and to U.S. Provisional Patent Application No. 62/459,509, filed Feb. 15, 2017. U.S. patent application Ser. No. 15/324,062 is a national stage application under 35 U.S.C. 371 of PCT Application No. PCT/US2015/039723 having an international filing date of Jul. 9, 2015, which designated the United States, which PCT application claims the benefit of U.S. Provisional Patent Application No. 62/022,276, filed Jul. 9, 2014, and to U.S. Provisional Patent Application No. 62/037,513, filed Aug. 14, 2014. PCT Application No. PCT/US2015/063195 claims the benefit of U.S. Provisional Patent Application No. 62/086,122, filed Dec. 1, 2014. All of these applications are incorporated herein by reference in their entirety.

FIELD

This disclosure provides cell or particle settling devices with enhanced settling on multilayered inclined surfaces. The devices of the present disclosure have applications in numerous fields, including: (i) high cell density biological (mammalian, microbial, plant or algal) cell cultures secreting polypeptides, hormones, proteins or glycoproteins, vaccines or vaccine-like particles, or other small chemical products, such as ethanol, isobutanol, isoprenoids, flavor and fragrance compounds, etc.; (ii) separating and recycling porous or non-porous solid catalyst particles catalyzing chemical reactions in liquid or gas phase surrounding solid particles; (iii) separating and collecting newly formed solids in physical transformations such as crystallization, flocculation, agglomeration, precipitation, etc., from the surround liquid phase; (iv) capture and purification of secreted proteins, such as monoclonal antibodies, and others, on affinity ligands, such as protein A immobilized on microspherical beads; (v) in vitro expansion of various mammalian cells, such as human mesenchymal stem cells, differentiated human cells e.g. cardiomyocytes or red blood cells, modified human cells, e.g. chimeric antigen receptor transfected T lymphocytes or CAR-T cells, etc. for autologous or allogenic cell therapy applications; and (vi) clarifying process water in large scale municipal or commercial waste water treatment plants by settling and removing complex biological consortia or activated sludge or other solid particles.

DESCRIPTION OF RELATED ART

Of all the above-mentioned fields of application for settling devices, the more immediately applicable well-established field is the production of biological proteins, polypeptides or hormones secreted from suspension cultures of recombinant microbial or mammalian cells. Most common methods of producing biological proteins in recombinant mammalian and microbial cells rely on fed-batch cultures, wherein cells are grown to high cell densities and then typically exposed to an induction medium or inducer to trigger the production of proteins. If the desired proteins are secreted out of the cells, it is more profitable to switch from a fed-batch culture to a continuous perfusion culture, which can maintain high cell density and high productivity over a much longer duration of culture. During continuous perfusion cultures, live and productive cells are retained or recycled back to the bioreactor while the secreted proteins are continuously harvested from the bioreactor for downstream purification processes.

Some key advantages of continuous perfusion cultures over fed-batch cultures are: (1) the secreted protein products are continuously removed from the bioreactor, without subjecting these products to potential degradation by proteolytic and/or glycolytic enzymes released into the culture medium from dead cells; (2) live and productive cells are retained or recycled back to achieve high cell densities in continuous perfusion bioreactors, where they continue to produce valuable proteins inside the controlled bioreactor environment for much longer culture duration, rather than being killed and removed from the bioreactor at the end of each fed-batch culture; (3) the perfusion bioreactor environment can be maintained much closer to steady state conditions (thereby maintaining a more consistent product quality by design) with the continuous addition of fresh nutrient media and removal of waste products along with the harvested protein products, unlike the dynamically changing concentrations of nutrients and waste products in fed-batch culture; and (4) with a subset of cell retention devices, smaller dead or dying cells can be selectively removed from the perfusion bioreactor before these cells lyse and release their intracellular enzymes, thereby maintaining a high viability fraction of cells and high quality of the secreted protein products as they are harvested.

Many cell retention devices have been developed in the mammalian cell culture industry, such as the internal spin filter devices (Himmelfarb et al., Science 164: 555-557, 1969), external filtration modules (Brennan et al., Biotechnol. Techniques, 1 (3): 169-174, 1987), hollow fiber modules (Knazek et al., Science, 178: 65-67, 1972), gravitational settling in a cyclone (Kitano et al., Appli. Microbiol. Biotechnol. 24, 282-286, 1986), inclined settlers (Batt et al., Biotechnology Progress, 6:458-464, 1990), continuous centrifugation (Johnson et al., Biotechnology Progress, 12, 855-864, 1999), and acoustic filtering (Gorenflo et al., Biotechnology Progress, 19, 30-36, 2003). The cyclones were found to be incapable of producing enough centrifugal force for sufficient cell separation at the device sizes and harvest flow rates used in the mammalian cell culture experiments (Kitano et al., 1986) and mammalian cells are seriously damaged at higher flow rates (and centrifugal forces) necessary for efficient cell separation (Elsayed, et al., Eng. Life Sci., 6: 347-354, 2006). While most of the other devices adequately retain all mammalian cells from the harvest, these devices are unable to separate dead cells from the live cells desired in the bioreactor. Consequently, dead cells keep accumulating inside the perfusion bioreactor and the membrane filters get clogged, necessitating the termination of the continuous perfusion bioreactor, typically within three or four weeks of mammalian cell culture.

Among all the cell retention devices available today, only the inclined settlers (Batt et al., 1990, supra and Searles et al., Biotechnology Progress, 10: 198-206, 1994) enable selective removal of smaller dead cells and cell debris in the overflow or harvest stream, while bigger, live and productive mammalian cells are continually recycled via the underflow back to the perfusion bioreactor. Therefore, it is feasible to continue the perfusion bioreactor operation indefinitely at high viability and high cell densities while the protein product is continuously harvested from the top of the inclined settler.

The inclined settler has previously been scaled up as multi-plate or lamellar settlers (Probstein, R. F., U.S. Pat. No. 4,151,084, April 1979) and used extensively in several large-scale industrial processes such as wastewater treatment, potable water clarification, metal finishing, mining and catalyst recycling (e.g. Odueyngbo et al., U.S. Pat. No. 7,078,439, July 2006).

Citing our first demonstration of a single plate inclined settler (Batt et al., 1990) to enhance productivity of secreted proteins in mammalian cell culture applications, a multi-plate or lamellar settler device has been patented for the scale up of inclined settlers for use in hybridoma cell culture (Thompson and Wilson, U.S. Pat. No. 5,817,505, October 1998). Such lamellar inclined settler devices have been used to culture recombinant mammalian cells in continuous perfusion bioreactors at high bioreactor productivity (due to high cell density) and high viability (>90%) for long durations (e.g. several months without any need to terminate the perfusion culture). U.S. Patent Publication No. 2011/0097800 to Kauling et al., describes a scaled up version of inclined settlers that uses cylindrical tubes wrapped at inclined angles. The device is described as useful in the culturing of larger mammalian cells, such as CHO, BHK, HEK, HKB, hybridoma cells, ciliates, and insect cells.

None of these cell retention devices have been demonstrated for harvesting secreted protein products in perfusion bioreactor cultures of the smaller, and hence more challenging, microbial cells. Lamellar settlers have been tested with yeast cells to investigate cell settling with limited success (Bungay and Millspaugh, Biotechnology and Bioengineering, 23:640-641, 1984). Hydrocyclones have been tested in yeast suspensions, mainly to separate the yeast cells from beer, again with only limited success (Yuan et al., Bioseparation, 6: 159-163, 1996; Cilliers and Harrison, Chemical Engineering Journal, 65: 21-26, 1997).

A modified cyclone with a spiral vertical plate inside the cyclone was proposed to improve the separation efficiency in wastewater treatment (Boldyrev V V, Davydov E I, settling tanks, as described in Russian Patent No. 2,182,508) and an earlier description of this arrangement has been described for the decantation of solids in liquid suspension (U.S. Pat. No. 4,048,069, September 1977). The modified cyclone disclosed in Russian patent No. 2,182,508 includes a spiral wound plate housed in a vertical cylindrical barrel with a conical bottom. A slit is provided along the entire height of a central waste water inlet tube, which is plugged at the bottom in order to channel waste water from the inlet tube into the vertical spiral wound plate. The spiral starts at the central tube and ends at the wall of the cylindrical housing, forming a channel through which particle-laden waste water flows. The particles settle in the vertical sedimentation column of the spiral channel. The height of the settler zone is the vertical height of the spiral plate and the width of the channel is formed by the walls of the spiral wound plate, which is held constant throughout its length. A pipe for removing the purified water is installed at the upper part of the cylindrical body. A conduit for removing sediment is installed at the bottom of the conical bottom portion. In operation, waste water enters through the central tube and enters the spiral zone through the slit or opening. The spiral channel serves to increase the flow path and hence increase the residence time of liquid in the settler. The spiral also serves to increase the contact (wall) area for the fluid. The main driving force in clarification is gravity acting on the particles of the suspension, as the suspension goes around the spiral-wound vertical sedimentation column. The slurry that is left on the wall of the spiral or in the channel, falls into the conical bottom of the settler, and is removed periodically from the settler. Purified water is drawn from a pipe on the side of cylindrical housing near the top.

As described in the Russian patent document, the flow pattern of the waste water-containing solids is reversed from the typical flow pattern of a common cyclone, as the dirty water enters at the center, via the central tube and enters into the spiral channel through the slits, and the purified water is removed from the periphery or outside of the vertical cylindrical body via a purified water pipe. This modified and flow-reversed cyclone device has not been proposed for, or applied to any fields other than waste water treatment.

Thus, a particle settling device that can leverage centrifugal forces and gravitational forces on particles in liquid suspension in a relatively small space is desired.

SUMMARY

This disclosure provides cell or particle settling devices with enhanced settling on multilayered, inclined surfaces arranged within a cyclone housing. The particle separation devices of this disclosure may be used in numerous applications, and represent a large improvement over the prior art separation devices. In some embodiments these surfaces may be attached to a plurality of vertical cylindrical plates. In other embodiments, the settling devices include a spiral conical surface, or several inclined plates approximating an angled conical surface connected to the bottom of a spiral. The numerous, layered inclined plates enhance the settling efficiency of the particles from the bulk fluid moving either downward or upward inside a conical cyclone assembly in which the liquid volume moves progressively from the periphery of the conical spiral to the center of the settler device.

In one or more embodiments, the settler devices of this disclosure include a cyclone housing (often referred to as a "hydrocyclone"), a spiral vertical plate positioned inside the cyclone housing, the spiral vertical plate joined at its bottom with a spiral conical surface tapering down to an opening. Notably, in some embodiments, there is no plug or other impediment preventing the flow of liquid or suspended particles from the spiral vertical plates or spiral conical surfaces toward the opening. The spiral conical surface forms lamellar inclined settler plates in a conical geometry.

In related embodiments, the devices of the disclosure include a cyclone housing, a spiral vertical plate positioned inside the cyclone housing, the spiral vertical plate joined at its bottom with a spiral conical settling surface tapering down to an opening. In this embodiment, the vertical spiral plate has a decreasing height towards the center of the device, and substantially constant spacing between the successive spiral rings. The spiral conical settling surfaces at the bottom of a spiral vertical plate have increasing lengths to match the decreasing height of the vertical spiral plate and extend to approximately the center of the settler device. Similarly, in some embodiments, there is no plug or other impediment preventing the flow of liquid or suspended particles from the spiral vertical plates or spiral conical surfaces toward the opening.

In one embodiment, the inclined settling surfaces are provided by numerous annular strips, or 'ramps', of metal stretched and aligned at an angle between about 30 degrees and about 60 degrees from vertical, and joined to the outer surface of each cylinder or tube. In another embodiment, the angle of the ramps is about 45 degrees from the vertical. The horizontal spacing between the successive parallel ramps in each annular region between the cylinders can be varied between about 5 mm to about 15 mm.

The inclined settling strips significantly enhance the settling efficiency of the particles from the bulk fluid as the bulk fluid moves upward in the annular settling zones created between the vertical tubes. As the harvest moves up through the annular inclined settling zones, bigger particles (e.g., live and productive cells) settle on the strips, slide down, exit at the outer edges of the strips and fall down vertically into the conical section of the cyclone assembly. These devices can be scaled up or down to suit the separation needs of different industries or applications or sizes as the separation surface is scaled up or down volumetrically in three dimensions, compared to the more typical one- or two-dimensional scaling of previous settling devices.

In all of the embodiments described above, attaching the spiral vertical plates to the spiral conical settling surfaces can be accomplished by welding or otherwise joining (i.e., gluing or other adhesives, bonding, ultrasonic welding, clamping, or the like) curved angular plates at a fixed inclination to the circular bottom edge of the spiral vertical plate.

In all of the embodiments described above, the spiral conical surface can be tightly fitted to obtain a continuous conical spiral surface. Alternatively, small gaps between the spiral conical surfaces are acceptable for a discontinuous conical spiral surface, provided the gaps in the surface are staggered between successive conical spirals.

In all of the embodiments described above, the angle of inclination for the conical spiral surfaces can be between 30 degrees and 60 degrees from the vertical. In certain embodiments, the angle of inclination for the conical spiral surfaces is about 45 degrees from the vertical. For stickier particles (typically mammalian cells), the angle of inclination is preferably closer to the vertical (i.e., about 30 degrees from the vertical. For non-sticky solid particles (for example, catalyst particles), the angle of inclination can be further from the vertical (preferably, about 60 degrees from vertical).

In other embodiments, the settler device of this disclosure includes a cyclone housing that encloses a series of stacked cones positioned inside the cyclone housing, tapering down to a central opening, with no vertical plates. The cones of this embodiment are supported in the stack, one above the other, by supports that maintain a distance (or channel width) between the successive cones in the stack. In certain embodiments, the supports comprise three or more projections attached to the upper and/or lower surface of one or more of the cones to position successive cones at a desired distance (the desired channel width) apart. Optionally, the supports may comprise at least three L-shaped elements interconnected to a surface of each cone that is distal to the truncated apex of the cone. The L-shaped elements include a first side interconnected to a second side at an apex and are interconnected to the surface such that the first side supports a second cone in the stack of cones. The second side is substantially parallel to the surface of the cone. Optionally, the second side may project beyond the cone to space the cone from an interior surface of the cyclone housing. As in the previous embodiments, in some embodiments, there is no plug or other impediment preventing the flow of liquid or suspended particles from the stacked conical surfaces toward the central opening.

In another embodiment, a settler devices of this disclosure includes a cyclone housing enclosing:

1) a first stack of two or more stacked cones, each having a central opening, and, 2) an optional second stack of two or more stacked cones, each having a central opening, joined at or near their bottom with conical surfaces tapering down to a central opening at the bottom of the cyclone housing.

The stacked cones (in both the first and optional second stack of two or more stacked cones) comprise at least three projections supporting each cone above the next successive cone in the stack. The projections are preferably placed at a substantially constant distance and are formed at a generally equal size to hold each successive cone in the stack at about an equal spacing between all of the cones in the stacks. In one embodiment, there are at least three projections for each cone to properly support each successive cone, but each cone may comprise more than three projections, as needed to adequately or properly support the cone. For example, each cone may comprise four projections, or may comprise eight projections, to support the next successive cone in the stack.

The projections, or "vertical supports," may represent an impediment to settled particles or cells sliding down the surface of a cone towards the central opening or the gap around the inner circumference of the cyclone housing between the housing and the cones. These projections are attached to one surface of a cone, but these projections do not attach to another cone in a stack of cones. Thus, these projections do not attach two or more cones in a stack to one another.

There is preferably a substantially constant spacing between each successive conical surface created by the projections supporting each successive cone in a stack of cones. The spacing between successive cones may be varied between about 1 mm to about 2.5 cm.

This arrangement of settling surfaces, provided by the successive stacks of cones, each of which is supported by the next successive cone, but is not permanently attached to the next successive cone, is particularly useful for separation applications in which the particle settling device, and the conical surfaces therein, requires regular or continual service, such as disassembly and cleaning of the conical settling surfaces within the settler device.

This arrangement of first and optional second stacks of cones significantly enhances the settling efficiency of particles from a bulk fluid as the bulk fluid moves through the settling device. As the bulk liquid, including particles such as cells, moves through the stacked cones of the settler device of this disclosure, bigger particles (e.g., live and productive cells) settle on the surface of the cones. Cells sliding down the upper or first stack of cones, slide down the conical surfaces to the outer edges of the cones and fall down vertically into the conical section of the cyclone housing. Additionally, cells sliding down the lower or second stack of cones, slide down the conical surfaces to the central opening of the cones and fall down vertically towards the central opening of the cyclone housing.

These devices can be scaled up or down to suit the separation needs of different industries or applications or sizes as the separation surface is scaled up or down volumetrically in three dimensions, compared to the more typical one- or two-dimensional scaling of previous settling devices.

Scale up of the devices of this disclosure can be performed simply by increasing the diameter of the cyclone housing (and correspondingly increasing the diameter of cones stacked inside) and/or increasing the height of the cyclone (which increases the number of cones in either one or both of the first and second stack of cones). For example, using a 10-inch (25.4 cm) diameter cylinder, with a spacing of approximately 10 mm between successive ramps, about 80 ramps going up may be welded to the outside of the 10-inch (25.4 cm) diameter cylinder. For a 12-inch (30.5 cm) diameter cylinder, approximately 92 inclined settling ramps can be placed within the cylinder, and so on, in proportion. The effective projected area for cell settling increases proportional to the square of the diameter of cyclone housing and increases proportional to the height of internal cylinders. So the effective settling area of the compact settling devices of this disclosure scales up proportional to the cube of cyclone diameter (assuming the height of the internal settler is also increased proportionally) or equivalently, to the volume of cyclone housing. This three dimensional or volumetric scale-up of the effective settling area makes the settling device of this disclosure much more compact compared to previous inclined settler devices.

The radial spacing in the annular regions between different cylinders can be between about 1 cm to about 10 cm, with an optimum around about 2.5 cm. A small clearance of about 1 mm between the inclined settling ramps and the internal surface of the next successive cylinder provides useful space for settled particles (for example cells) to slide down the surface of the ramps and exit the ramps on the side, rather than sliding all the way down to the bottom of the ramp. The side-exiting cells settle vertically along the inside of each cylinder. When these settling cells reach the conical surface at the bottom of each cylinder, they slide down on the inclined surface on the cone to the central opening at the bottom of the cyclone housing. An advantage of the increasing fluid velocity while going down the inclined conical surface to the central opening is that the increasing number of settled cells sliding down the cone are swept down to the central opening, rather than being allowed to accumulate by the faster liquid velocities.

In all of the embodiments of the settler devices of this disclosure, the components of the settler devices may be composed of a metal and/or a plastic. In certain embodiments, the components of the settler devices are composed of stainless steel (such as stainless steel alloy 316 or similar materials used for applications in microbial or mammalian cell culture, as well as other metals used for applications in chemical process industries, such as catalyst separation and recycle). In specific embodiments these settler devices are composed entirely of stainless steel. In specific embodiments including a spiral vertical plate, and the spiral conical surface and the spiral vertical plate are metals joined by welding.

Metal settling devices of this disclosure can be constructed by forming the cyclone housing and forming the number of desired cones constituting each of the first and optional second stack of cones, sized to fit within the cyclone housing. Projections of the desired size, shape, and number may then be mounted on one or both surfaces of each cone in order to support the next successive cone. In some embodiments, metal settling devices can be constructed by cutting out annular strips from a flat metal sheet, and stretching them in a perpendicular direction to reach an angle between about 30 degrees and about 60 degrees (preferably about 45 degrees) from vertical around an inner cylinder, and welding tabs at the ends of the metal annular strips to the outside of the cylinder.

In other embodiments, the material of construction of these settler devices may also include non-metals including, for example, plastics for use as single-use disposable settler devices, or glass for housing transparency, etc. Optionally, in one embodiment, the settler devices are composed entirely of plastic. A plastic settling device according to this disclosure can be fabricated continuously, as a single piece, using, for example, injection molding or three-dimensional printing technologies. In some embodiments, the plastic settling device may be transparent or translucent. In one embodiment, at least a portion of the settling device is translucent or transparent. In still another embodiment, the material of at least a portion of the settling device is transparent to light of a predetermine range of wavelengths.

The angle of inclination for the conical surfaces (or "ramps") may be between about 30 degrees to about 60 degrees from the vertical. For use with stickier particles (typically mammalian cells), the angle of inclination may be closer to the vertical (i.e., around 30 degrees from vertical). For use with non-sticky solid catalyst particles, the angle of inclination can be further from vertical (for example, around 60 degrees from vertical).

In all embodiments, all or some of the surface of the cyclone housing, the spiral vertical plate or the conical surfaces may be completely or partially coated with one or more of a non-sticky plastic, teflon, and silicone. Additionally, or alternatively, the metals (especially stainless steel) may be electropolished to provide a smooth surface.

One or more sensors may be positioned to monitor conditions within all embodiments of the settler devices of this disclosure. In one embodiment, at least one sensor is positioned to monitor conditions with a tube or line interconnected to the settler devices of this disclosure. In another embodiment, the line is a return line interconnected to a bottom outlet port of the settler device.

The sensors may be selected to determine one or more of pH, DO, Glucose, temperature, and $CO_2$ (include dissolved $CO_2$ which is also known as partial $CO_2$) within the cyclone housing or the line. In one embodiment, the sensors include a probe in contact with a solution within the cyclone housing or the line. The probe may be affixed to an interior surface portion of the settler device or the line. In one preferred embodiment, at least one sensor and/or probe is positioned within the lower conical portion of the settler device. In another embodiment, the sensor and/or probe is spaced from one or more of the side port and the bottom port. In still another embodiment, the sensor and/or probe is positioned within the line.

The probe may transmit data without contact to a reader. In this manner, the probe may measure a condition within the settler device and/or the line and transmit data to the reader outside the settler device. In one embodiment, the probe is a fluorescent probe. One or more of pH, DO, Glucose, temperature, and $CO_2$ may be measured by the probe within the cyclone housing. The probe is affixed to a portion of the cyclone housing. The portion of the cyclone housing is operable to transmit light produced by the fluorescent probe. In one embodiment, the portion of the cyclone housing is transparent or translucent. The reader (or meter) receives light from the fluorescent probe. In one embodiment, the reader includes an optical fiber that collects light transmitted by the fluorescent probe. Suitable probes and readers are available from a variety of vendors, including PreSens Precision Sensing GmbH.

In another embodiment, the probe within the settler device can transmit data to the reader outside the settler device by a network connection. For example, in one embodiment the probe can communicate with the reader by WiFi, Bluetooth, or any other wireless communication modality.

All of the embodiments of the settler devices of this disclosure may include a closure or lid over at least a portion of the cyclone housing at an end of the cyclone housing opposite the first opening. In all of these embodiments, the closure or lid may also include an outlet or port for removing liquids or entering liquids into the settler device. In all of these embodiments, the opening and the additional ports or outlets in the cylindrical housing and/or the lid are in liquid communication with the outside and the inside of the cyclone housing to allow the passage of liquids into and/or out of the cyclone housing of the settler device, and in each instance of such opening or inlet/outlet, these passage ways into and out of the cyclone housing may include valves or other mechanisms that can be opened or closed to stop or restrict the flow of liquids into or out of the settler devices of this disclosure.

The thickness of the material constructing the cones is preferably as thin as necessary to maintain the rigidity of shape and to minimize the weight of the concentric stack of cones to be supported inside the cyclone housing. The radius and height of this device can be scaled up independently as much as needed for the large-scale processes as may be calculated from predictive equations such as provided for inclined plate settlers (Batt et al. 1990, supra).

An important factor causing particle separation in the settler devices of this disclosure is the enhanced sedimentation on the inclined surfaces, which has been successfully demonstrated by Boycott (Nature, 104: 532, 1920) with blood cells and on inclined rectangular surfaces as successfully demonstrated by Batt et al. (1990) with hybridoma cells producing monoclonal antibodies. Additional factors enhancing the cell/particle separation are the centrifugal force on the cells/particles during their travel up the annular regions between successive cylinders and the settling due to gravity in the vertical sedimentation columns of the spiral channel.

While lamellar plates have been used to scale up inclined plate settlers by each dimension independently, i.e. increasing the length, or the width or the number of plates stacked on top of the each plate, the spiral conical settling zone can be scaled up in three dimensions simultaneously by simply increasing the horizontal radius of this device. As the horizontal radius of the device increases, the number of vertical and conical surfaces can be proportionally increased by keeping a constant distance (or channel width) between the successive spirals. The particle separation efficiency is directly proportional to the total projected horizontal area of the inclined settling surfaces. With an increase in device radius, the projected horizontal area increases proportional to the square of the radius, and the number of feasible spiral cones at a channel width also increases with the radius, resulting in a three dimensional scale up in the total projected area (i.e. proportional to the cube of radius) by simply increasing the radius.

Thus, a particle settling device of this disclosure may include a cyclone housing and at least one vertical tube disposed inside the cyclone housing, the at least one vertical tube joined at one end with a conical surface tapering down to a first opening in the cyclone housing. At least one annular strip is attached to a vertical surface of the at least one vertical tube at an angle between about 30 degrees and about 60 degrees from vertical. There is at least one additional opening in the cyclone housing substantially opposite the first opening. The vertical tubes may include at least one material selected from the group consisting of a metal and a plastic. The vertical tubes may be stainless steel, and may be composed entirely of stainless steel. The vertical tubes, the annular strip, and the conical surfaces may all be metals joined by welding. Alternatively, the tubes may be composed entirely of plastic. At least one surface of the cyclone housing, the at least one vertical tube, the annular strip, and the spiral conical surface is coated with a non-sticky plastic or silicone.

The angle of inclination for the conical surfaces is about 45 degrees from vertical, or between about 30 degrees from vertical and about 60 degrees from vertical.

The width of an annular ringed channel formed between adjacent vertical tubes is between about 1 mm and about 50 mm. The number of vertical tubes within the settler device may be between about 2 and about 30.

The settler device may include a closure over at least a portion of the cyclone housing at an end of the cyclone housing opposite the first opening. At least one additional opening in the cyclone housing, may be configured to open from a side of the cyclone housing tangential to at least one vertical tube, in liquid communication with the outside and the inside of the cyclone housing.

A liquid harvest outlet may be formed in the closure, in liquid communication with the outside and the inside of the cyclone housing.

The annular strip is attached to the at least one vertical tube in a spiral that rises at an angle of about 45 degrees to vertical from an end of the tube adjacent the first opening spiraling around the at least one vertical tube up to the opposite end of the at least one vertical tube. The annular strip may be attached to the at least one vertical tube and may be of sufficient width to leave a gap of between about 0.5 mm and about 10 mm between an edge of the annular strip and the cyclone housing or an adjacent vertical tube.

Thus, another aspect of this disclosure provides a method of settling particles in a liquid suspension. The method includes, but is not limited to: (i) introducing a liquid suspension of particles into a particle settling device of this disclosure; (ii) collecting particles from a first opening in a cyclone housing of the settler device; and (iii) collecting a liquid from another opening in the settling device. In certain embodiments of this method, the liquid is collected from an opening in a closure that covers at least a portion of the cyclone housing at an end of the cyclone housing opposite the first opening. In certain embodiments, liquid is collected from at least one additional opening in the cyclone housing, which opening is configured to open from a side of the cyclone housing.

In certain embodiments of these methods, the liquid suspension may include at least one of a recombinant cell suspension, an alcoholic fermentation, a precipitating protein solution, a mixture of aqueous fluid containing cells and organic layer containing extracted organic products produced by the cells, a suspension of solid catalyst particles in a liquid mixture containing mostly the products and depleted reactants, a suspension of microspheres coated with protein A molecules which can bind the monoclonal antibodies from the cell culture broth, a suspension of microcarrier beads with mammalian cells growing attached on the beads, a municipal waste water, and an industrial waste water. In certain embodiments of these methods, the liquid suspension may include at least one of mammalian cells, bacterial cells, yeast cells, plant cells, algal cells, human stem cells or differentiated human cells and/or insect cells. In certain embodiments of these methods, the liquid suspension may include at least one of biodiesel-producing algae cells, recombinant mammalian and/or murine hybridoma cells, metabolically engineered yeast cells producing secreted organic products, and yeast in beer. In certain embodiments of these methods, the liquid suspension may include recombinant microbial cells selected from *Pichia pastoris, Saccharomyces cerevisiae, Kluyveromyces lactis, Aspergillus niger, Escherichia coli,* and *Bacillus subtilis.*

In certain embodiments of these methods, the step of introducing a liquid suspension into the settler device includes directing a liquid suspension from a plastic bioreactor bag into the particle settling device.

In certain embodiments of these methods, the liquid collected from the settler device may include at least one of biological molecules, organic or inorganic compounds, chemical reactants, and chemical reaction products. In certain embodiments of these methods, the liquid collected from the settler device includes at least one of hydrocarbons, polypeptides, proteins, alcohols, fatty acids, hormones, carbohydrates, antibodies, antibodies, terpenes, isoprenoids, biodiesel, polyprenoids, and beer. In certain embodiments of these methods, the liquid collected from the settler device includes at least one of biodiesel components, secreted therapeutic proteins or hormones such as insulin or its analogs, antibodies, monoclonal antibodies, brazzein, growth factors, sub-unit vaccines, viruses, virus-like particles, colony stimulating factors, erythropoietin (EPO), secreted flavor or fragrance compounds, including geraniol, myrcene, sweetener protein brazzein, etc.

Another aspect of the present disclosure is a particle settling device that may include, but is not limited to, a cyclone housing including one or more of: (1) a first conical portion; (2) a second conical portion; (3) a cylindrical portion located between the first and second conical portions; (4) at least one inlet for introducing a liquid into the cyclone housing; (5) a first outlet port; (6) a second outlet port; and (7) a first stack of cones located within the cyclone housing. In one embodiment, the first outlet port is associated with the first conical portion and the second outlet port is associated with the second conical portion. Optionally, the liquid introduced into the cyclone housing may be a liquid suspension including particles. The particles may be of a plurality of sizes.

In one embodiment, the first outlet port may be for harvesting a clarified liquid. The clarified liquid may include a first subset of particles. The first subset of particles may comprise cell debris, dead cells, and the like. Optionally, the first outlet port may be formed in a closure of the cyclone housing. The first outlet port being in liquid communication with the outside and the inside of the cyclone housing.

Optionally, in another embodiment, the second outlet port may be for harvesting a concentrated liquid. The concentrated liquid may include a second subset of particles. In one embodiment, the second subset of particles may include live cells. In another embodiment, particles of the second subset of particles are generally larger than particles of the first subset of particles. In still another embodiment, each particle of the second subset of particles generally has a greater mass than the particles of the first subset of particles. The second outlet port being in liquid communication with the outside and the inside of the cyclone housing.

In one embodiment, the first stack of cones occupies at least a portion of the first conical portion. Optionally, the first stack of cones occupies at least a portion of the cylindrical portion. Optionally, one or more cones of the first stack of cones includes a truncated apex oriented towards the first outlet port. Additionally, or alternatively, at least one cone of the first stack of cones is devoid of the central opening. In another embodiment, each cone of the first stack of cones includes an open base oriented towards the second outlet port. In one embodiment, the cones of the first stack of cones are generally centered in the cyclone housing. In another embodiment, the cones of the first stack of cones are about centered around a substantially central opening formed by the truncated apex of one or more of the cones.

Optionally, the cyclone housing may further include a second stack of cones. In one embodiment, the second stack of cones occupies at least a portion of the second conical portion. In another embodiment, the second stack of cones occupies at least a portion of the cylindrical portion. In one embodiment, each cone of the second stack of cones is transverse to the cones of the first stack of cones.

In one embodiment, at least one cone in the first stack of cones is composed of a metal or a plastic. In another embodiment, at least one cone in the first stack of cones is composed at least partially of stainless steel. In still another embodiment, at least one cone in the first stack of cones is composed entirely of a plastic. Additionally, or alternatively, at least one surface of a cone in the first stack of cones is coated with a plastic or silicone.

Optionally, an angle of inclination for a surface of a cone in the first stack of cones is between about 30 degrees to about 60 degrees from vertical. In another embodiment, the angle of inclination of the cones is about 45 degrees.

In another embodiment, each cones of the second stack of cones includes a truncated apex oriented towards the second outlet port. Each cone of the second stack of cones may also include an open base oriented towards the first outlet port. In one embodiment, the cones of the second stack of cones are generally centered in the cyclone housing. In another embodiment, the cones of the second stack of cones are about centered around a substantially central opening formed by the truncated apex of one or more of the cones. When present, the cones of the second stack of cones may be comprised of at least one of a metal and a plastic. In one embodiment, at least one cone in the second stack of cones is composed at least partially of stainless steel. In still another embodiment, at least one cone in the second stack of cones is composed entirely of a plastic. Additionally, or alternatively, at least one surface of a cone in the second stack of cones may be coated with a plastic or silicone.

In one embodiment, an angle of inclination for a surface of a cone in the second stack of cones is between about 30 degrees to about 60 degrees from vertical. In another embodiment, the angle of inclination of the cones in the second stack of cones is about 45 degrees.

In one embodiment, the cones of the first stack of cones have a substantially uniform spacing. Additionally, the cones of the second stack of cones may have a substantially uniform spacing. In one embodiment, the cones of the first stack of cones have a different spacing compared to the cones of the second stack of cones.

In one embodiment, the at least one inlet is configured as an inlet port in liquid communication with the outside and the inside of the cyclone housing. In another embodiment, the at least one inlet is associated with at least one of the first conical portion, the second conical portion, and the cylindrical portion of the cyclone housing. In one embodiment, a first inlet of the at least one inlets is associated with the cylindrical portion of the cyclone housing. In another embodiment, a second inlet of the at least one inlets is associated with one of the first and second conical portions. In yet another embodiment, the second inlet is associate with the second conical portion. In another embodiment, the at least one inlet is configured to be interconnected to a disposable bioreactor bag. The disposable bioreactor bag may comprise a plastic material.

In one embodiment, the cyclone housing further includes a fluid jacket. The fluid jacket is associated with one or more of the first conical portion, the second conical portion, and the cylindrical portion. In one embodiment, the fluid jacket is associated with the second conical portion and the cylindrical portion. The fluid jacket may include at least one port to receive a fluid of a predetermined temperature. Optionally, the fluid jacket may include a second port to extract fluid from the fluid jacket.

In one embodiment, the cyclone housing further includes a sensor. The sensor is configured to measure a condition within the cyclone housing. In one embodiment, the sensor comprises a fluorescent probe. Optionally, the sensor is positioned to measure a condition within the second conical portion. In another embodiment, the sensor is associated with a line interconnected to the second outlet port. In one embodiment, at least a portion of cyclone housing proximate to the sensor is transparent or translucent. Additionally, or alternatively, the second conical portion is transparent or translucent. In one embodiment, the sensor comprises a plurality of sensors. In another embodiment, the sensor is operable to measure at least one of pH, dissolved oxygen (DO), Glucose, temperature, and dissolved $CO_2$ ($pCO_2$). In one embodiment, data from the sensor may be used to adjust a temperature of fluid within the fluid jacket. In another embodiment, the data from the sensor may be used to adjust one or more of pH, temperature, dissolved oxygen concentration, dissolved carbon dioxide, and nutrient concentrations within the particle settling device.

It is another aspect of the present disclosure to provide a method of settling particles in a suspension. The method includes, but is not limited to, one or more of: (1) introducing a liquid suspension of particles into a particle settling device; (2) collecting a clarified liquid from a first outlet port of the particle settling device; and (3) collecting a concentrated liquid suspension from a second outlet port of the particle settling device. The particle settling device may be any particle settling device disclosed herein.

In one embodiment, the clarified liquid may include a first subset of particles of the suspension. The first subset of particles may comprise cell debris, dead cells, and the like.

In one embodiment, the concentrated liquid may include a second subset of particles of the suspension. The second subset of particles may include live cells. In another embodiment, particles of the second subset of particles are generally larger than particles of the first subset of particles. In still another embodiment, each particle of the second subset of particles generally has a greater mass than the particles of the first subset of particles.

In one embodiment, the particle settle device includes a cyclone housing, comprising: (a) a first conical portion; (b) a second conical portion; (c) a cylindrical portion located between the first and second conical portions; (d) at least one inlet for the liquid suspension to enter the cyclone housing; (e) the first outlet port for harvesting the clarified liquid; (f) the second outlet port for discharging the concentrated liquid suspension; and (g) a first stack of cones located within the cyclone housing. In one embodiment, the first stack of cones occupies at least part of the first conical portion. Additionally, the first stack of cones may occupy at least part of the cylindrical portion.

In one embodiment, each cone of the first stack of cones includes (i) a truncated apex positioned distal to the second conical portion, and (ii) an open base positioned proximate to the second conical portion. Optionally, the cones of the first stack are generally centered around a substantially central opening formed by the truncated apex in each cone in the first stack of cones.

In one embodiment, at least one cone in the first stack of cones is composed of a metal or a plastic. In another embodiment, at least one cone in the first stack of cones is composed at least partially of stainless steel. In still another embodiment, at least one cone in the first stack of cones is composed entirely of a plastic. Additionally, or alternatively, at least one surface of a cone in the first stack of cones is coated with a plastic or silicone.

Optionally, an angle of inclination for a surface of a cone in the first stack of cones is between about 30 degrees to about 60 degrees from vertical. In another embodiment, the angle of inclination of the cones is about 45 degrees.

In one embodiment, an angle of inclination for a surface of a cone in the second stack of cones is between about 30 degrees to about 60 degrees from vertical. In another embodiment, the angle of inclination of the cones in the second stack of cones is about 45 degrees. In one embodiment, the cones of the first stack of cones have a substantially uniform spacing.

In one embodiment, the particle settling device further includes a fluid jacket. The fluid jacket is associated with one or more of the first conical portion, the second conical portion, and the cylindrical portion. In one embodiment, the fluid jacket is associated with the second conical portion and the cylindrical portion. The fluid jacket may include at least one port to receive a fluid of a predetermined temperature. Optionally, the fluid jacket may include a second port to extract fluid from the fluid jacket.

In another embodiment, the particle settling device further includes a sensor. The sensor is configured to measure a condition within the particle setting device. Optionally, the sensor is positioned to measure a condition within the second conical portion. In another embodiment, the sensor is associated with a line interconnected to the second outlet port. In one embodiment, the sensor comprises a plurality of sensors. In one embodiment, the sensor is operable to measure at least one of pH, DO, Glucose, temperature, and $pCO_2$. In another embodiment, the sensor is a fluorescent probe. In one embodiment, at least a portion of cyclone housing proximate to the fluorescent probe is transparent or translucent. Additionally, or alternatively, the second conical portion may be transparent or translucent.

Optionally, the method further comprises collecting data from the sensor. Additionally, the method may include using data received from the sensor to adjust one or more of pH, temperature, dissolved oxygen concentration, dissolved carbon dioxide, and nutrient concentrations within the particle settling device.

In one embodiment, the liquid suspension comprises at least one of a recombinant cell suspension, an alcoholic fermentation, a suspension of solid catalyst particles, a municipal waste water, and industrial waste water. In another embodiment, the liquid suspension comprises at least one of mammalian cells, bacterial cells, yeast cells, and plant cells. In another embodiment, the liquid suspension comprises at least one of algae cells, plant cells, mammalian and/or murine hybridoma cells (i.e., cells in different stages of differentiation), stem cells, CAR-T cells, red blood precursor and mature cells, cardiomyocytes or other attachment prone cells growing attached on microcarrier beads, yeast in beer, and eukaryotic cells. In still another embodiment, the liquid suspension comprises recombinant microbial cells selected from at least one of *Pichia pastoris, Saccharomyces cerevisiae, Kluyveromyces lactis, Aspergillus niger, Escheri-* chia coli, Bacillus subtilis, and other microbial cells. In yet another embodiment, the liquid suspension comprises non-cellular particles. For example, the liquid suspension may include one or more of microcarrier beads for attached stem cell growth, an affinity ligand coated microspheric bead or resin, surface activated microspherical beads, and the like.

Optionally, the clarified liquid collected may comprise at least one of biological molecules, organic or inorganic compounds, chemical reactants, and chemical reaction products. In one embodiment, the clarified liquid collected comprises at least one of hydrocarbons, polypeptides, proteins, alcohols, fatty acids, hormones, carbohydrates, antibodies, glycoproteins, terpenes, isoprenoids, polyprenoids, fragrance and flavor compounds, and beer. In another embodiment, the clarified liquid collected comprises at least one of biodiesel, insulin or its analogs, brazzein, antibodies, growth factors, colony stimulating factors, and erythropoietin (EPO).

In one embodiment, introducing the liquid suspension into the particle settling device comprises directing the liquid suspension from a plastic disposable bioreactor bag into the particle settling device.

Yet another aspect of the present disclosure is a particle settling device, comprising: (A) a cyclone housing; (B) at least two conical plates disposed inside the cyclone housing; (C) a first opening in the cyclone housing; and (D) a second opening in the cyclone housing. In one embodiment, the at least two conical plates are stacked one above the other. In one embodiment, the cyclone housing include between about 3 and about 30 conical plates.

In another embodiment, the at least two conical plates are separated by a substantially constant distance. Optionally, a width of a channel formed between adjacent surfaces of the at least two conical plates is between about 1 mm and about 50 mm. In one embodiment, at least three supports hold each of the conical plates in the stack.

In one embodiment. each of the conical plates include a truncated apex proximate to the first opening and an open base positioned distal to the first opening. The conical plates may be generally centered in the cyclone housing. In one embodiment, the stack of at least two conical plates is arranged in a substantially vertical position within the cyclone housing. Optionally, an angle of inclination for a surface of each of the at least two conical plates is between about 30 degrees and about 60 degrees from vertical.

Optionally, the at least two conical plates comprise at least one material selected from the group consisting of a metal and a plastic. In one embodiment, the at least two conical plates are comprised stainless steel. In another embodiment, at least one surface of the cyclone housing and the at least two conical plates is coated with a non-sticky plastic or silicone.

In one embodiment, the cyclone housing is comprised entirely of plastic. In another embodiment, the cyclone housing is comprised entirely of stainless steel.

In one embodiment, the cyclone housing includes a cylindrical portion and a conical portion. In one embodiment, the first opening is associated with the conical portion. Optionally, the second opening may be associated with the cylindrical portion. In one embodiment, the second opening is positioned in a sidewall of the cylindrical portion. In another embodiment, the second opening is positioned in a lid associated with an open end of the cylindrical portion. In yet another embodiment, the second opening is positioned in the conical portion.

The preceding is a simplified summary of the disclosure to provide an understanding of some aspects of the settler devices of this disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below. Additional aspects of the present disclosure will become more readily apparent from the Description of Embodiments, particularly when taken together with the drawings.

DESCRIPTION OF EMBODIMENTS

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The phrases "at least one," "one or more," and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the disclosure such as impurities ordinarily associated therewith.

The transitional phrase "consisting essentially of" limits the scope of a claim to the specified materials or steps and those that do not materially affect the basic and novel characteristic(s) of the claimed invention.

Figure 1A:
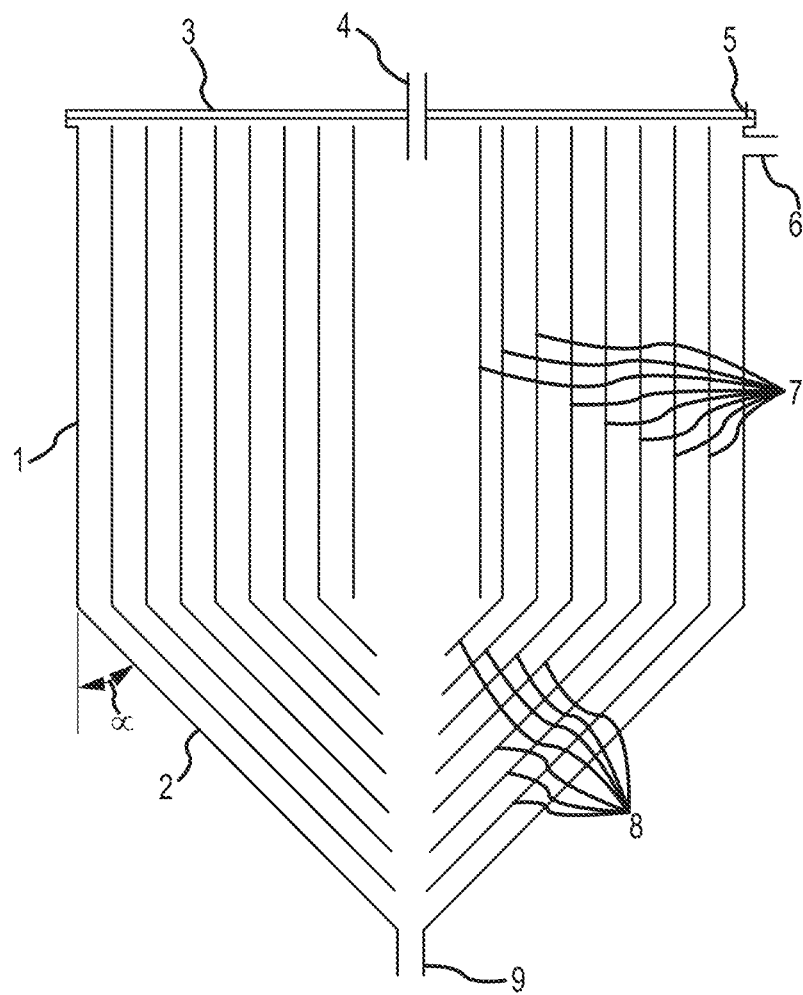
FIG. 1A shows a cross sectional view through the side of one embodiment of a conical spiral settler device of this disclosure.
Figure 1B:
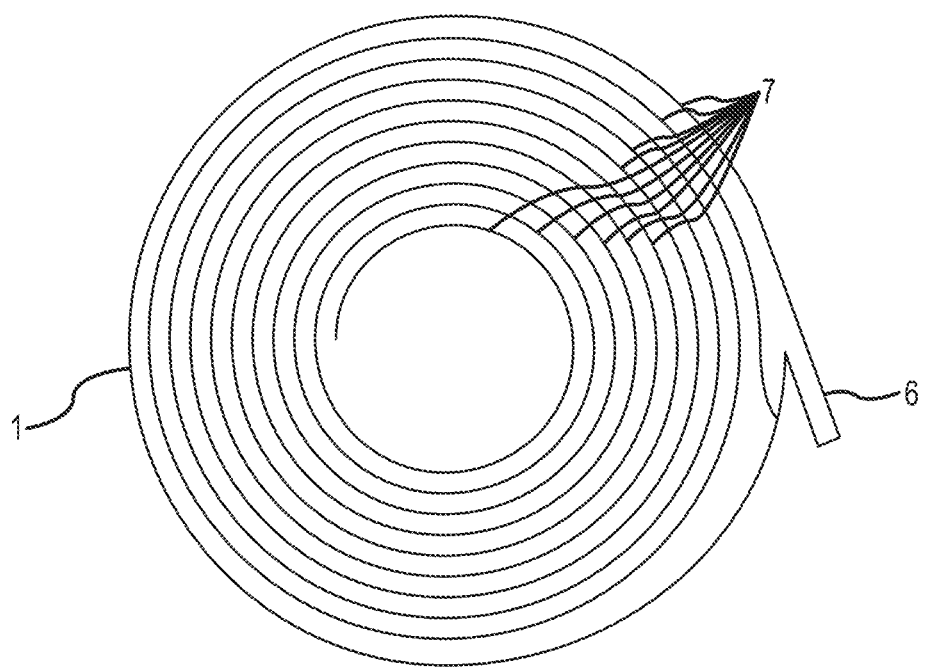
FIG. 1B is a cross sectional view through the top of the conical spiral settler device of FIG. 1A, showing a top view of spiral plates inside a cyclone housing.

In one embodiment, depicted in FIGS. 1A and 1B, a settler device of this disclosure includes a cyclone housing (1) enclosing a spiral vertical plate (7). The spiral vertical plate (7) is joined at one end with a conical surface (8) which tapers down to an opening (9). As depicted in FIG. 1B, the spiral vertical plate (7) is supported within the cyclone housing by attachment to the cyclone housing (1). Optionally, the spiral vertical plate (7) may also include one or more supporting attachments to a top plate (3).

Opening (9) is of sufficient diameter to allow removal of settled cells or particles. In one embodiment, there is a substantially constant spacing between successive rings of the spiral vertical plate (7). The conical surface (8) joined to the spiral vertical plate (7) may be formed as a single continuous spiral surface, or individual angled plates, and acts as a lamellar inclined settler plate, in a conical geometry.

The cyclone housing (1) optionally includes a means to control the temperature of the settler device, such as a temperature control jacket or reservoir for cooling or heating fluids to be circulated around all or part of the cyclone housing (1).

The conical bottom portion (2) of the cyclone housing (1) extends from a vertical surface of the cyclone housing (1) to the opening (9) and is preferably positioned at an angle α from the vertical that substantially matches the angle of at least one conical surface (8).

The top plate (3), which may function as a lid to the cyclone housing, may be optionally attached to the top of the cyclone housing (1) by at least one screw (5). The top plate (3) may optionally be secured in place over the cyclone housing (1) over an o-ring (not shown).

The top port (4) may act as an inlet or outlet port for liquid and/or particles entering or exiting the settler device through the top plate (3). In one embodiment, the top port (4) is substantially centered in the top plate (3).

One or more tangential ports (6) located in the cyclone housing (1) may also act as one or more of an inlet and outlet port for liquid and/or particles entering or exiting the settler device through the cyclone housing (1). These one or more tangential ports (6) may be positioned in the cyclone housing (1) at any position between the opening (9) and the top plate (3). In one embodiment, at least one tangential port (6) is positioned in the conical bottom portion (2). The tangential ports (6) may each be dedicated inlet ports, dedicated outlet ports, or dual function inlet/outlet ports, for the transfer of liquid and/or particles into or out of the settler device. As noted above, in one embodiment, there is no plug or other impediment preventing the flow of liquid or suspended particles from the spiral vertical plate (7) or the conical surfaces (8), toward the opening (9). Alternatively, a plug may be provided for one or more of the tangential ports (6) and opening (9).

Figure 2:
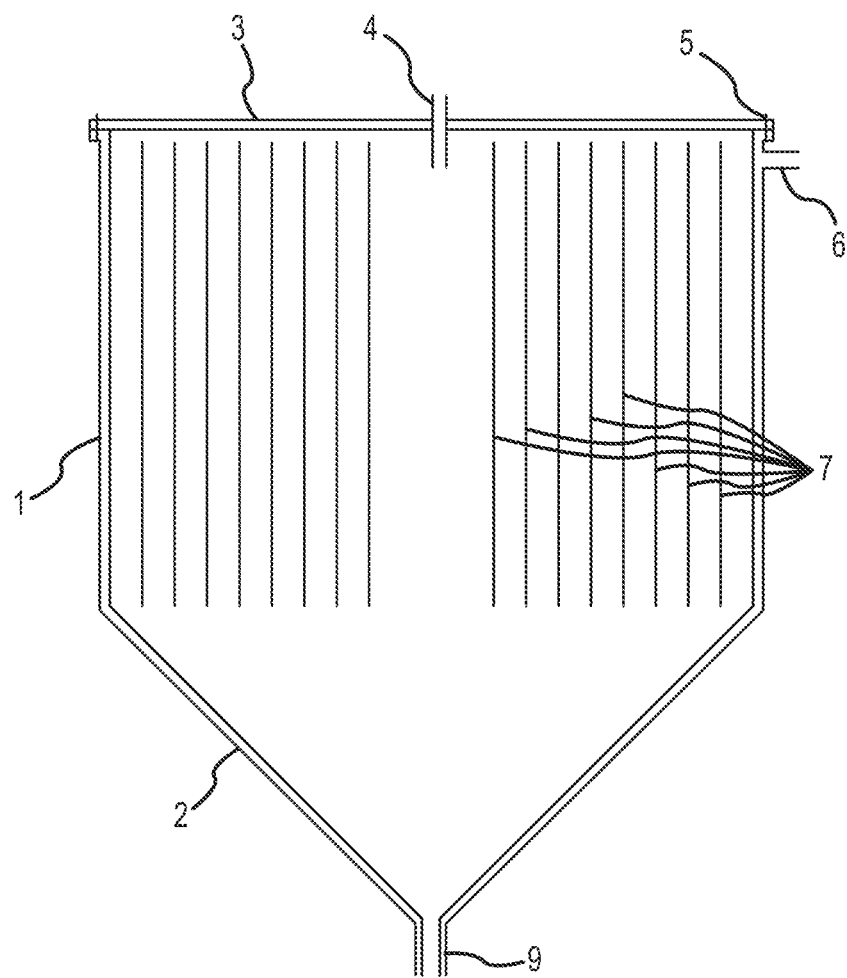
FIG. 2 shows a cross sectional view through another embodiment of the settler device of this disclosure, without the conical spiral surface.

A modified version of the settler device of this disclosure is depicted in FIG. 2. In this embodiment, the conical surface (illustrated in FIG. 1A, reference number 8) is omitted. Thus, the conical bottom portion (2) of the settler device is at least substantially empty. The settler device of the embodiment illustrated in FIG. 2 also works well for many separation applications due to the synergistic effects of centrifugal forces acting on particles in this settler device, when a liquid suspension of particles is introduced through a tangential port (6) near the top of cyclone housing (1) proximate the top plate (3) and the increased residence time of particles in the vertical sedimentation channel of the vertical conical plate (7).

Figure 3:
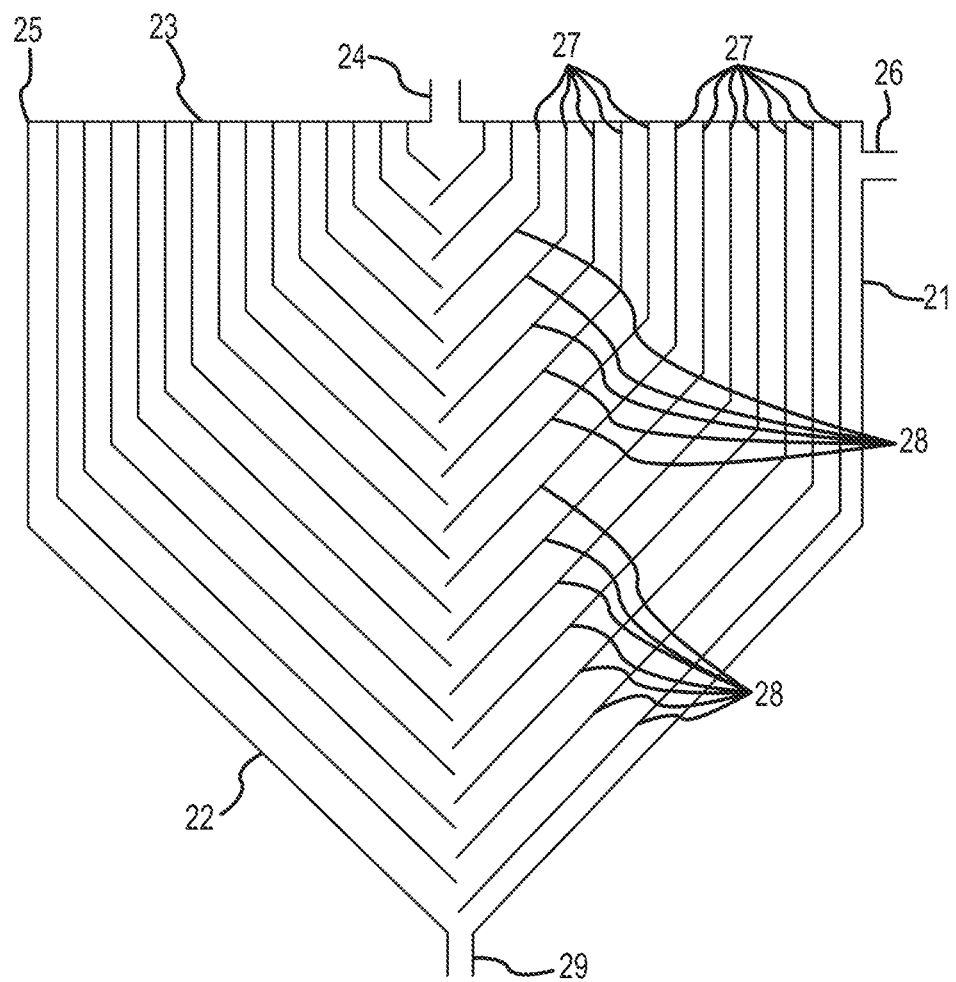
FIG. 3 shows a cross sectional view of an alternate configuration of a spiral conical surface, with extensions to the conical settler surface to ensure the upward flow of cell culture broth through all the conical spiral and vertical sedimentation chambers within a settler device of this disclosure.

Another embodiment of the settler device of this disclosure is depicted in FIG. 3. This embodiment is particularly useful for smaller scale particle separation applications, such as particle settlers for use with a plastic bag bioreactor using only two vertical ports. In this embodiment, the settler device of this disclosure includes a cyclone housing (21) enclosing spiral vertical plate (27). The spiral vertical plate (27) is joined at one end with a conical surface (28) tapering down to an opening (29) in a conical bottom portion (22). The spiral vertical plate (27) is supported within the cyclone housing (21) by attachment to the cyclone housing (not shown). Optionally, the spiral vertical plate (27) may also include one or more supporting attachments to a top plate (23). The cyclone housing (21), including the conical bottom portion (22), of this embodiment may also include a means to control the temperature of the settler device, such as a fluid jacket as described herein.

The spiral vertical plate (27) is formed with progressively longer vertical spirals, moving from the center of the settler device of this embodiment towards the cyclone housing (21). The conical surfaces (28) joining one end of the spiral vertical plate (27) are formed in increasingly longer lengths to extend from the joined end of the spiral vertical plates (27) to a position proximate the center of the settler device, in order to direct cells or particles towards the opening (29).

As depicted in FIG. 3, the end of the conical surfaces (28) opposite the end joining the spiral vertical plate (27) may extend beyond the center of the settler device to partially overlap successive conical surfaces (28). In one embodiment, there is no plug or other impediment preventing the flow of liquid or suspended particles from the spiral vertical plate (27) or the conical surfaces (28), toward the opening (29). As with the embodiment depicted in FIG. 1, in one embodiment there is a substantially constant spacing between successive rings of the spiral vertical plate (27). Optionally, the conical surface (28) joined to the spiral vertical plate (27) may be formed as a single continuous spiral surface, or individual angled plates. For use in small scale, bioreactor or biobag separation applications, opening (29) may function for inlet of cell culture broth as well as recycling settled cells or particles back to a biobag or bioreactor.

Top plate (23) is optionally attached to the top of the cyclone housing (21) by at least one screw (25), and may be secured in place over the cyclone housing (21) over an o-ring (not shown). Top port (24) may act as an inlet or outlet port for liquid and/or particles entering or exiting the settler device through the top plate (23). In this embodiment, top port (24) is particularly useful for removing clarified cell culture liquid. In one embodiment, top port (24) is substantially centered in the top plate (23).

Similarly, one or more optional tangential ports (26) located in the cyclone housing (21) and/or the conical bottom portion (22) may also act as an inlet or outlet port for liquid and/or particles entering or exiting the settler device through the cyclone housing (21). These one or more optional tangential ports (26) may be positioned in the cyclone housing (21) and/or the conical bottom portion (22) at any position between the opening (29) and the top plate (23). The optional tangential ports (26) may each be dedicated inlet ports, dedicated outlet ports, or dual function inlet/outlet ports, for the transfer of liquid and/or particles into or out of the settler device. Such optional tangential port (26) located in the cyclone housing (21) proximate the top plate (23) is typically not needed in small scale, bioreactor or biobag separation applications, but may be useful for faster filling of the settler device with cell culture liquids before priming a pump in liquid communication with the central top port (24), as described below. If the optional tangential inlet port (26) is not used, the cell culture broth can be sucked up through opening (29) by a peristaltic pump in fluid communication with the top port (24), as described below.

Figure 4:
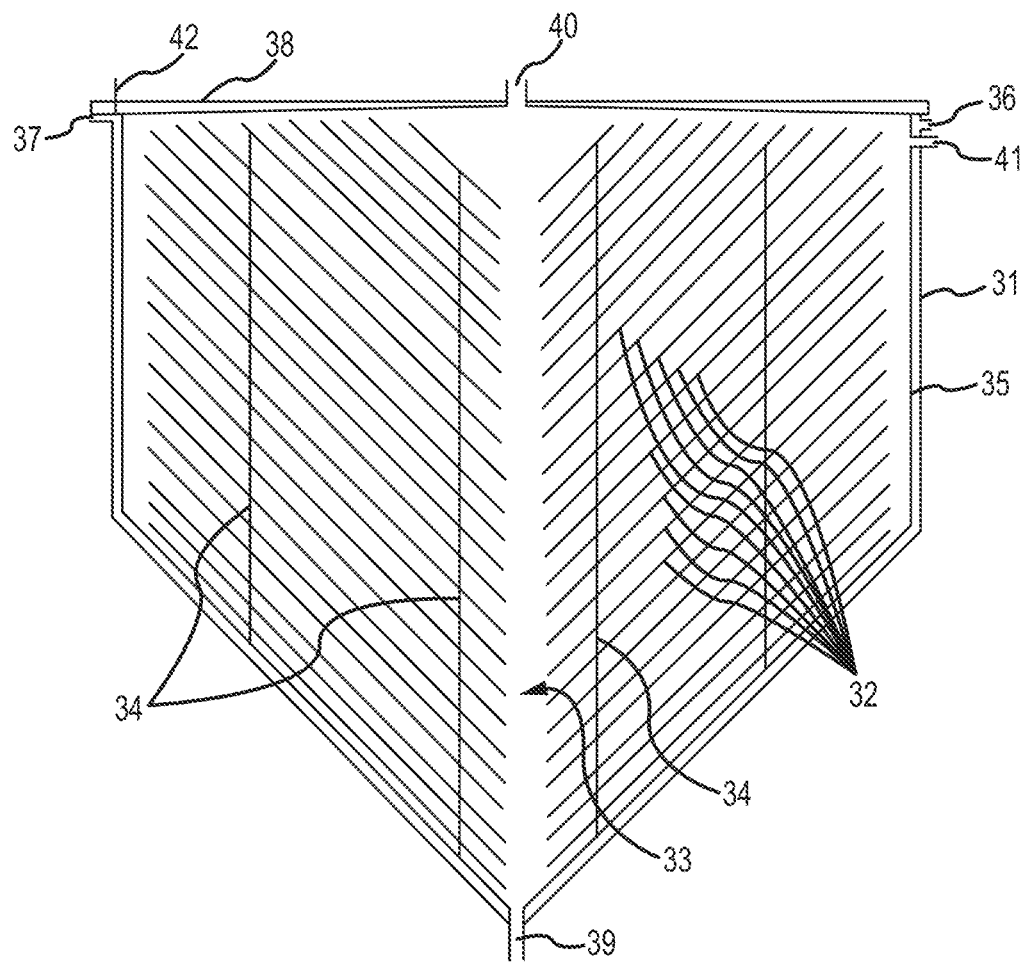
FIG. 4 shows a cross sectional view through the side of one embodiment of a conical settler device of this disclosure.

Another embodiment of the settler device of this disclosure is depicted in FIG. 4. This embodiment is particularly useful for separation applications in which the particle settling device requires regular or continual service, such as disassembly and cleaning of the conical settling surfaces within the settler device. In this embodiment, the settler device of this disclosure includes a cyclone housing (31) enclosing a stack of two or more stacked cones (32), each having a central opening (33), the cyclone housing (31) tapering down to an opening (39).

The stacked cones (32) comprise at least three vertical supports (34) supporting each cone (32) above the next successive cone (32) in the stack. In preferred embodiments, the vertical supports (34) are preferably placed at about a constant distance and are formed at a substantially equal length to hold each successive cone (32) in the stack at substantially an equal spacing between all of the cones (32) in the stack. There should be at least three vertical supports for each cone (32) to properly support each cone, but each cone (32) may comprise more than three vertical supports as needed to adequately or properly support the cone (32). However, each vertical support represents an impediment to settled particles or cells sliding down the surface of the cone (32) towards the central opening (33).

The vertical supports (34) may be attached to the top of each cone (32), thereby supporting the next successive cone (32) in the stack. Alternatively or additionally, the vertical supports (34) may be attached to the bottom of each cone (32), thereby supporting the cone (32) above the next successive cone (32) in the stack.

Optionally, in another embodiment, the vertical supports (34) may comprise at least three L-shaped spacers or triangular spacers interconnected to an upper surface of each cone (34) that is distal to the truncated apex of the cone. The L-shaped spacers include a first side interconnected to a second side at an apex. In one embodiment, the L-shaped spacers and/or triangular spacers are interconnected to the upper surface such that the first side supports the next successive cone (32) in the stack. The second side is substantially parallel to the surface of the cone (32). Optionally, the second side may project beyond the cone (32) to space the cone a predetermined distance from an interior surface of the cyclone housing (31). In one embodiment, the L-shaped spacers and the triangular spacers have a substantially thin cross-section to prevent or minimize interference with the movement or flow of liquid and suspended particles within the cyclone housing (31). Optionally, the L-shaped spacers and/or the triangular spacers may be integrally formed with the cone (32). In another embodiment, the L-shaped spacers and/or the triangular spacers are interconnected to the cone (32).

In one embodiment, there is no plug or other impediment preventing the flow of liquid or suspended particles from the central opening (33) in each cone (32) toward the opening (39).

As depicted in FIG. 4, the cyclone housing (31), may include a means to control the temperature of the settler device, such as a jacket or reservoir (35) for cooling or heating fluids to be circulated around all or part of the cyclone housing (31). Ports (36, 37) may be inlet or outlet ports for the circulation of heating or cooling fluids through the reservoir (35).

Top plate (38) is optionally attached to the top of the cyclone housing (31) by at least one screw (42), and may be secured in place over the cyclone housing (31) over an o-ring (not shown). Top port (40) may act as an inlet or outlet port for liquid and/or particles entering or exiting the settler device through the top plate (38). Top port (40) is particularly useful for removing clarified cell culture liquid. In one embodiment, the top port (40) is substantially centered in the top plate 38.

Similarly, one or more optional tangential ports (41) located in the cyclone housing (31) may also act as an inlet or outlet port for liquid and/or particles entering or exiting the settler device through the cyclone housing (31). These one or more optional tangential ports (41) may be positioned in the cyclone housing (31) at any position between the opening (39) and the top plate (38). The optional tangential ports (41) may each be dedicated inlet ports, dedicated outlet ports, or dual function inlet/outlet ports, for the transfer of liquid and/or particles into or out of the settler device.

In each of the embodiments of this disclosure, the number of spirals or cones typically range from about 3 to about 30 or more, depending on the radius of the device. In each of the embodiments of this disclosure, the channel width (i.e., the distance between each successive spiral or each successive conical cone) can range between about 1 mm and to about 50 mm. For larger flow rates, device sizes, and dense fluids, the larger channel width will be preferable to minimize the pressure drop or friction. A smaller channel width can increase the number of spirals or cones that can fit inside a given radius of the device. Smaller channel widths are, however, more prone to clogging by dense packing of the settled or settling particles. The thickness of spiral or cone material should be as small as possible to maintain the rigidity of shape while minimizing the weight of the spiral or cones supported inside the cyclone housing.

The radius and size of these settler devices can be scaled up easily in three dimensions, as much as needed for large-scale/large-volume processes. However, the scale up of these devices needs to be carried out empirically, as theoretical development of predictive equations is not yet available, as they were for lamellar settlers (Batt et al. 1990). These settler devices can be scaled up or down to suit the separation needs of different industries or applications or sizes as the separation surface is scaled up or down approximately in three dimensions, compared to the more typical one- or two-dimensional scaling of previous settling devices.

In each of the embodiments of this disclosure, the angle of inclination of the surfaces of the conical surfaces or the stacked cones can also be between about 30 degrees and about 60 degrees from the vertical. In certain embodiments, the angle of inclination for the surfaces of the conical surfaces or stacked cones is about 45 degrees from the vertical. As described above, for the separation of stickier particles (typically mammalian cells), the angle of inclination is preferably closer to the vertical (i.e., about 30 degrees from the vertical). For less-sticky solid particles (for example, catalyst particles), the angle of inclination can be further from the vertical (preferably, about 60 degrees from vertical).

The material of construction of any of the settler devices of this disclosure can be stainless steel (especially stainless steel 316), or similar materials used for applications in microbial or mammalian cell culture, as well as other metals used for applications in chemical process industries, such as catalyst separation and recycle. In certain embodiments, the settler devices of this disclosure include stainless steel surfaces that are partially or completely electropolished to provide smooth surfaces that cells or particles may slide down after settling out of liquid suspension. In certain embodiments, some or all of the surfaces of the settler device may be coated with a non-sticky plastic or silicone, such as dimethyldichlorosilane. In related embodiments, the material construction of any of these settler devices may be non-metals, including plastics, for use in, for example, single use disposable bioreactor bags, etc. While metal settling devices of the disclosure can be constructed via standard plate rolling and welding of steel angular plates to the bottom of the spiral plate, a plastic settler device of this disclosure, or individual parts thereof, may be more easily fabricated continuously as a single piece using, for example, injection molding or three-dimensional printing technologies.

In each of the embodiments of this disclosure, liquid may be directed into, or drawn out of, any of the ports or openings in the conical settling device by one or more pumps (for example a peristaltic pump) in liquid communication with the port or opening. Such pumps, or other means causing the liquid to flow into or out of the settler devices, may operate continuously or intermittently. If operated intermittently, during the period when the pump is off, settling of particles or cells occurs while the surrounding fluid is still. This allows those particles or cells that have already settled to slide down the inclined conical surfaces unhindered by the upward flow of liquid. Intermittent operation has the advantage that it can improve the speed at which the cells slide downwardly, thereby improving cell viability and productivity. In a specific embodiment, a pump is used to direct a liquid suspension of cells from a bioreactor or fermentation media into the settler devices of the present disclosure.

In each of the embodiments of this disclosure, the top plate, or lid, covering the cyclone housing may be concave, rising to a central core point. In these embodiments, the angle of rise in the concave top plate may preferably be between about 1 degree and about 10 degrees, more preferably between about 1 degree and about 5 degrees. This concave top plate creates a tent-like space above the center of the cyclone housing. Gas, bubbles, froth or the like may accumulate in this space and a tube may be inserted through an opening in the cyclone housing or through an opening in the top plate to withdraw such gasses, etc. from the space beneath the top of the cyclone housing. Similarly, fluid or gas may be pumped into the cyclone housing through such tube that is inserted through an opening in the cyclone housing or through an opening in the top plate.

Methods of Use and Operation Processes

The settling devices of this disclosure have applications in numerous fields, including: (i) high cell density biological (mammalian, microbial, plant or algal) cell cultures secreting polypeptides, hormones, proteins or glycoproteins, subunit vaccines, viruses, virus-like particles or other small chemical products, such as ethanol, isobutanol, isoprenoids, etc.; (ii) separating and recycling porous or non-porous solid catalyst particles catalyzing chemical reactions in liquid or gas phase surrounding solid particles; (iii) separating and collecting newly formed solids in physical transformations such as crystallization, flocculation, agglomeration, precipitation, etc., from the surround liquid phase; and (iv) clarifying process water in large scale municipal or commercial waste water treatment plants by settling and removing complex biological consortia or activated sludge or other solid particles.

Figure 5:
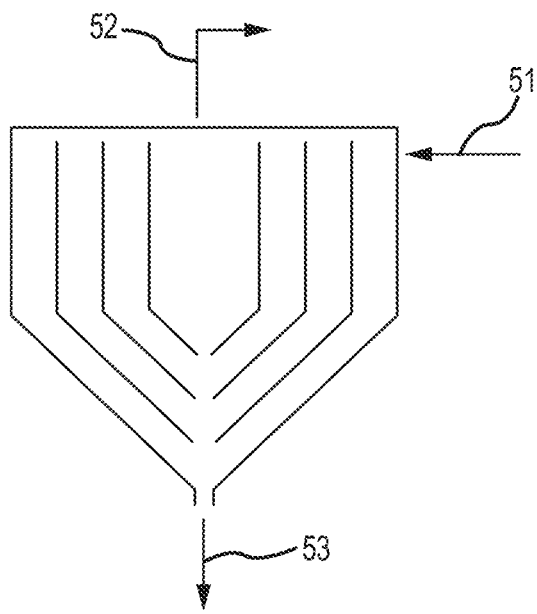
FIGS. 5-7 show schematic diagrams of different liquid flow patterns through a bioreactor of this disclosure.

FIG. 5 shows an effective flow pattern of liquid and particles through a settler device of this disclosure, producing maximal particle separation efficiency. As depicted in FIG. 5, a particle containing liquid (including, for example, cell culture liquid, waste water or reaction fluid containing solid catalyst particles, etc.) is preferably introduced tangentially into a settler device of this disclosure near the top of the cylindrical housing from the side along the direction of arrow (51), to take full advantage of the centrifugal forces on the particles, pushing them against the wall of the spiral vertical plate. The channel within the spiral vertical plate creates increased contact area, residence time and gradually increasing centrifugal force for the particles to be pushed against the spiral wall. The particles or cells sliding down the walls and settling in the vertical sedimentation columns of the spiral channel enter an enhanced sedimentation zone of the conical surfaces. Particles or cells settled on the inclined conical surfaces are swept down to the opening at the bottom of the conical housing by the dense liquid (i.e. liquid containing concentrated particles or cells) exiting at the bottom of the cone in the direction of arrow (53). Liquid exiting the outlet in the direction of arrow (53) contains concentrated cells or particles to be recycled to a bioreactor or directed to a chemical reactor, or waste water tank, etc. Clarified liquid containing any secreted proteins or other products and smaller particles or dead cells or cell debris, is harvested at an outlet along the direction of arrow (52).

In one embodiment, clarified liquid entering the central tube is removed or harvested at the top by suction from a pump attached on the tube connected to the top port. The dense liquid containing concentrated particles or cells can be recycled to the reactor or bioreactor or harvested as desired. The flow rate of the dense liquid exiting the bottom of the conical device is ideally equal to the difference in the inlet flow rate at the tangential entry near the top and outlet flow rate at the top, each controlled by a separate pump. Additional control valves may be added to the bottom liquid exit tube to ensure that the clarified liquid exits at the top and may be fully opened as needed to prevent or remove any dense packing of particles clogging the underflow stream.

Figure 6:
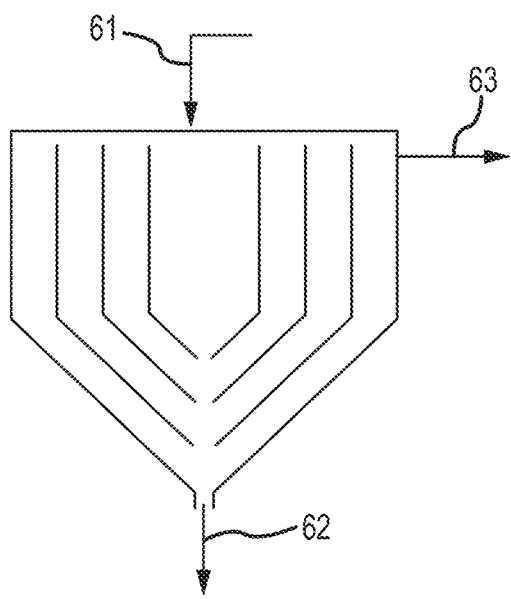

Another flow configuration for liquid and particles through a settler device of this disclosure is depicted in FIG. 6. This flow configuration results in a slightly reduced separation efficiency compared to the flow configuration depicted in FIG. 5 because the top vertical entry does not take advantage of any small centrifugal forces which can be created by the tangential entry depicted in FIG. 5. Nevertheless, this configuration makes use of the major separating principle of enhanced sedimentation on inclined surfaces and will be sufficient for full separation of larger live mammalian cells from smaller dead cells and cell debris if the device is sized adequately for use with a bioreactor.

In this operating embodiment, liquid containing cells or solid particles, or waste water is directed into the top of the settler device along the direction of arrow (61). Outlet liquid containing concentrated cells, particles or sludge to be recycled back to the bioreactor, chemical reactor or waste water tank exits the settler device along the direction of arrow (62). Clarified liquid containing any secreted proteins, smaller dead cells or cell debris, is harvested from the settler device near the top of the conical housing proximate the top of the settler device, along the direction of arrow (63).

Figure 7:
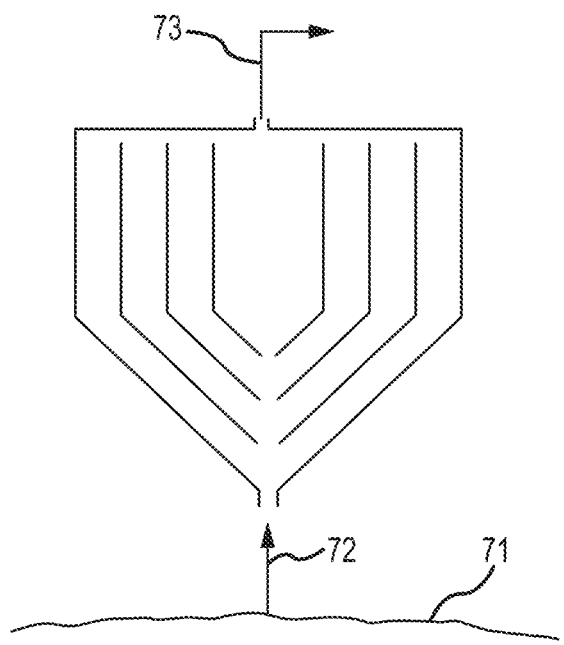

A third flow configuration useful for a settler device of this disclosure that includes only two ports is depicted in FIG. 7. A liquid suspension is directed along the direction of arrow (72) from a single-use disposable plastic bioreactor bag (71), which may be culturing either mammalian or microbial cells secreting one or more desired chemical products, into a bottom port of the settler device. The inlet port is firmly attached to the plastic bioreactor bag (71), but without any pump. This inlet port carries both the contents of the bioreactor bag upwards, and the settled cells downward back to the bioreactor bag. Thus, the feed inlet to the settler device and the underflow of settled particles or cells cross paths in the same bottom port of the conical settler device, i.e., the two streams (feed inlet and underflow) occur via the same bottom port. This flow configuration may be useful in connection with a single use, plastic disposable bioreactor bag, or with other applications used with smaller scale settler devices of this disclosure. Such smaller scale settler devices are typically made of plastic, and may be single-use, disposable plastic devices. In this flow configuration, clarified liquid outlet containing any secreted protein product and fewer smaller cells or cell debris, exits from the top port of the settler device along the direction of arrow (73).

If a third port is provided in the configuration of FIG. 7, it may be used initially to provide a vacuum suction to fill up or prime the device. In some embodiments, the third port is not provided in the settler device as it is not needed in conjunction with this embodiment containing a single port in which feed inlet and underflow of settled particles or cells cross paths in the same bottom port.

For the smaller scale applications with a plastic bag bioreactor with only two vertical ports used in the flow configuration as shown in FIG. 7, it is advantageous to extend the conical spiral surface closer to the center of the settler device to prevent a direct flow of inlet cell culture broth from the bottom port up through the central opening in the device. One possible extension of the conical spiral surface to ensure the flow of cell culture broth from bottom inlet through all the spiral conical and vertical sedimentation chambers of the device is shown in the sectional diagram of FIG. 3.

Figure 8:
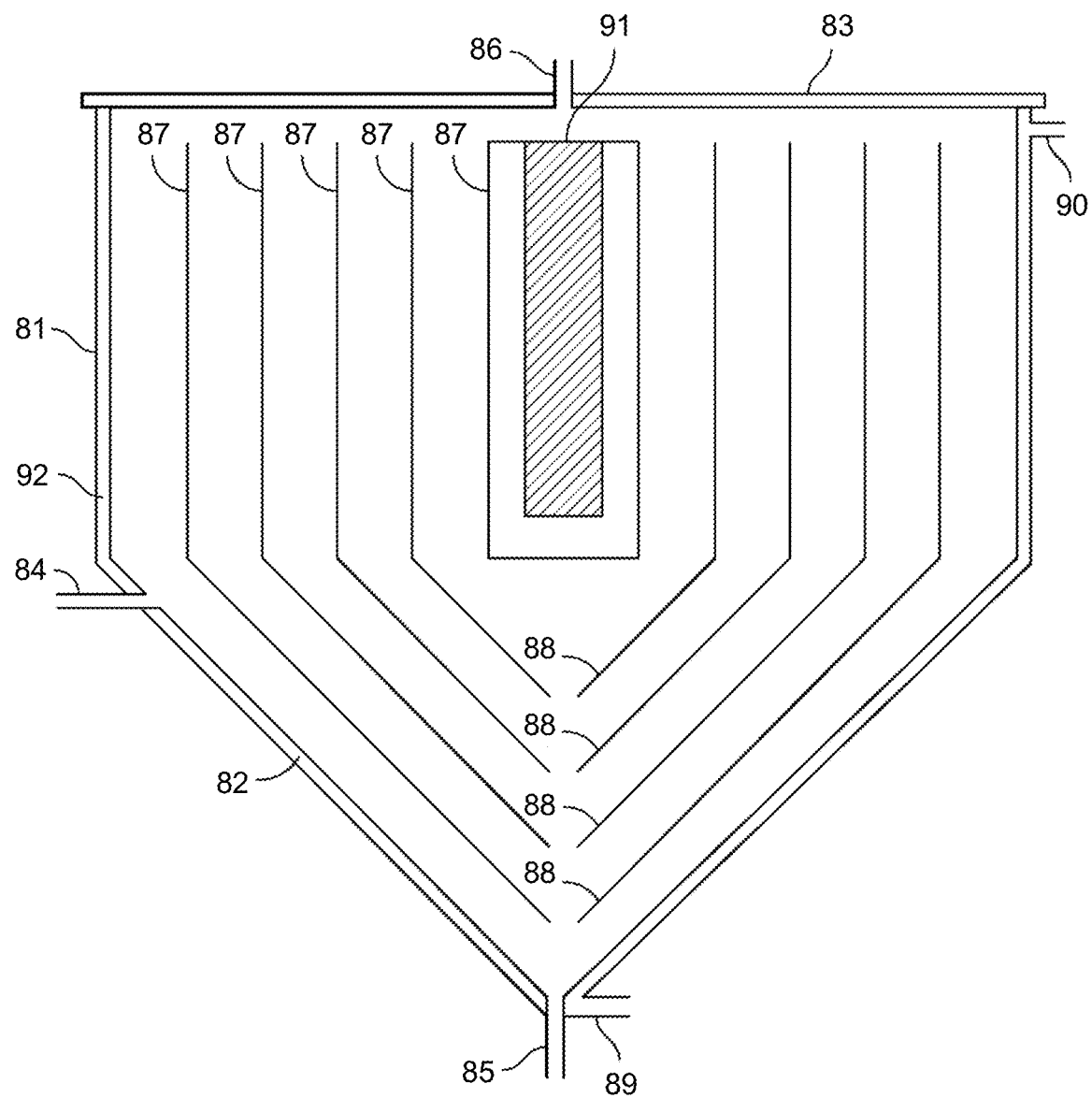
FIG. 8 shows a sectional view through a concentric cylindrical inclined settler device of this disclosure, including a vertical sight glass on the outer surface to show the inclined settling ramps in the outermost annular region.

Referring to FIG. 8, a sectional view of a concentric cylindrical inclined settler device of this disclosure includes an outer wall (81) of cylindrical section of the cyclone assembly, shown in FIG. 8 with an optional fluid jacket (92), a conical portion (82) of the cyclone assembly, with the optional fluid jacket (92) extending to this conical portion (82), a lid (83) on top of the assembly, a tangential port inlet (84) for a liquid (for example, a cell culture), entering near the top of conical portion (82), through the optional fluid jacket (92), a bottom outlet port (85) for returning concentrated liquid (for example, a concentrated cell culture containing settled cells to a bioreactor), and a top outlet port (86) for harvesting the clarified liquid (for example, culture liquid containing very few cells, which are mostly smaller dead cells and cell debris).

Concentric cylindrical tubes (87) are located within the outer wall (81). Annular strips (not shown) are attached to the concentric cylindrical tubes (87) at an angle between about 30 degrees to about 60 degrees (or, in another embodiment, about 45 degrees) from vertical. In one embodiment, the annular strips are attached to the inner cylinder, but not to the outer cylinder. Concentric cones (88) channel settled particles (for example, cells) to the bottom outlet port (85).

A first fluid port (89) accesses the optional fluid jacket (92) on the outside of the cyclone assembly. A second fluid port (90) accesses the optional fluid jacket (92) near the top of the cylindrical section (81) of the cyclone assembly. The first fluid port (89) may be used to inject (or remove) a fluid of a predetermined temperature into the optional fluid jacket (92). The second fluid port (90) may be used to remove (or inject) the fluid from the optional fluid jacket (92). In this manner, a selected fluid may circulate at a predetermined rate through the fluid jacket (92). Accordingly, the fluid jacket (92) may be used to heat or cool the cyclone assembly or maintain a predetermined temperature of the cyclone assembly. In one embodiment, the fluid for the fluid jacket (92) comprises water; however, other fluids are contemplated for use with the cyclone assemblies of the present disclosure.

As depicted in FIG. 8, an optional sight glass (91) is provided showing the inclined settler strips attached to the inside cylinder in the outermost annular region between the cylindrical tubes. As noted above, in one embodiment of the present disclosure, annular strips are not attached to the outer cylinder, intentionally leaving a small (approximately 0.5 mm-10 mm) gap between the strips and the outer cylinder, thereby allowing the settled particles to fall down through this gap.

As depicted in FIG. 8, the settler devices of this disclosure may include a closure or lid (83) over at least a portion of the settler device at an end of the settler device opposite the bottom outlet port (85). The closure or lid (83) may also include an outlet or port (86) for removing gases and liquids or entering liquids into the settler device. The opening and the additional ports or outlets in the lid are in liquid communication with the outside and the inside of the settler device to allow the passage of liquids and gases into and/or out of the settler device, and in each instance of such opening or inlet/outlet, these passageways into and out of the cyclone housing may include valves or other mechanisms that can be opened or closed to stop or restrict the flow of liquids into or out of the settler devices of this disclosure.

The lid (83) covering the settler device may be concave, rising to a central core point. The angle of rise in the concave top plate may preferably be between about 1 degree and about 10 degrees, more optionally between about 1 degree and about 5 degrees. Such concave top plate creates a tent-like space above the center of the settler device. Gas, bubbles, froth or the like may accumulate in this space and a tube may be inserted through an opening in the settler device or through an opening in the top plate to withdraw such gasses, etc. from the space beneath the top of the settler device. Similarly, fluid or gas may be pumped into the settler device through such tube that is inserted through an opening in the settler device or through an opening in the lid.

Figure 9:
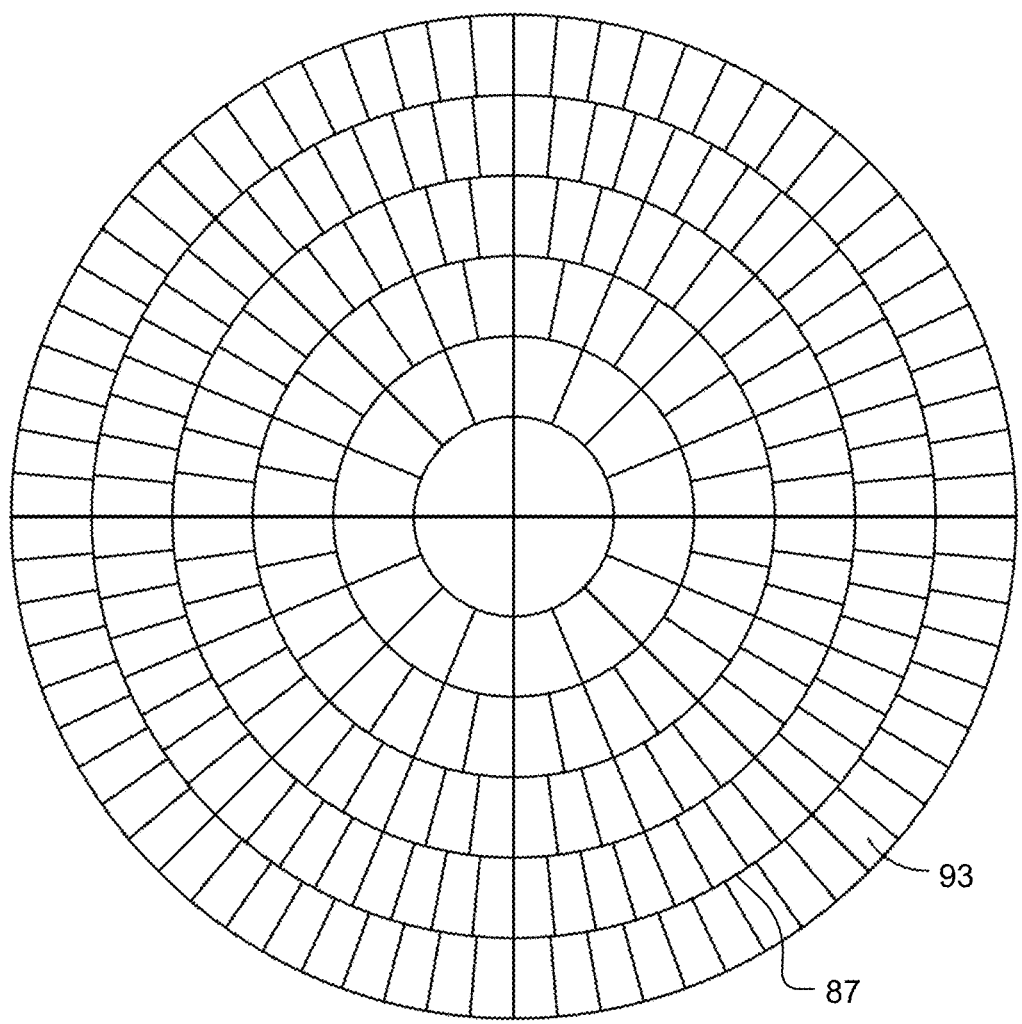
FIG. 9 shows a top view through a settler device of this disclosure, showing numerous inclined settling ramps welded to inner cylinders in the annular regions.

As depicted in FIG. 9, a top view of the concentric cylindrical inclined settler device of this disclosure shows numerous annular strips attached to the outside of each cylinder (87). The strips may be attached to the vertical cylinders at an angle between about 30 degrees to about 60 degrees to the vertical (typically at an angle of about 45 degrees to the vertical). As shown in FIG. 9, small (approximately 1 mm) spacings (93) are provided between each inclined settler strip and the next successive outer cylinder of each annular region, to allow the settled particles to fall down along the outer cylindrical wall onto the concentric cones in the bottom section of the assembly.

These settler devices may include a means to control the temperature of the settler device, such as reservoir for cooling or heating fluids to be circulated around all or part of the outer wall of the settler device. Ports may be inlet or outlet ports for the circulation of heating or cooling fluids through the reservoir.

A lid is optionally attached to the top of the settler device by one or more screws, and may be secured in place over the settler device over an o-ring.

Methods of Use and Operation of Processes of the Settling Devices Depicted in FIGS. 8 and 9

Referring now to the settling device depicted in FIGS. 8 and 9 of this disclosure, exemplary methods of using the settling devices are described.

A particle containing liquid (including, for example, cell culture liquid, waste water or reaction fluid containing solid catalyst particles, etc.) is introduced tangentially into a device of this disclosure though the port (84) near the top of the conical section (82) of cyclone housing assembly. Approximately 50%-99% of the entering liquid (typically about 90%) is removed through the bottom port (85), while the remaining 1%-50% (typically about 10%) of the liquid is removed through the top port (86). A pump (such as a peristaltic pump) may be used to suck liquid out of this top port (86), while the concentrated liquid exiting the bottom may be allowed to exit the bottom outlet (85) of the cyclone housing due to gravity, without the need for a pump. Most of the entering cells (or particles) are pushed against the conical walls of this assembly (88) through centrifugal forces upon entry, settle down the conical portion through a gentle vortex motion initially, getting faster as the liquid and particles/cells go down and exit via the bottom port. The rest of the cells, which have not settled, will move up through the annual regions in between the numerous inclined settling strips attached to the inside cylinder. As the liquid moves slowly up the annular inclined channels, bigger particles (e.g., live cells) will settle on the ramp and either slide down the ramp or more likely fall down the small (approximately 1 mm) spacing provided between the ramps and the outer walls of each annular region. These settled particles fall down vertically along the outer cylindrical walls until they reach the bottom conical section of the assembly and proceed to slide down the conical section to the bottom port (85).

By increasing the liquid flow rate through top port (86), it is possible to reduce the residence time of liquid inside the inclined settling zones such that smaller particles (for example dead cells and cellular debris) will not have settled by the time the liquid reaches the top of the settling zone, and therefore these smaller particles exit the settling device via the top port (86). This feature provides a simple method to remove smaller particles (such as dead cells and cellular debris) selectively via the top port (86) into a harvest stream, while larger particles (such as live and productive cells) are returned from the bottom port (85) to another vessel (such as a bioreactor).

Thus, in these methods, the step of introducing a liquid suspension into the settler device includes directing a liquid suspension from a plastic bioreactor bag into the particle settling device.

Liquid may be directed into, or drawn out of, any of the ports or openings in the settling device by one or more pumps (for example a peristaltic pump) in liquid communication with the port or opening. Such pumps, or other means causing the liquid to flow into or out of the settler devices, may operate continuously or intermittently. If operated intermittently, during the period when the pump is off, settling of particles or cells occurs while the surrounding fluid is still. This allows those particles or cells that have already settled to slide down the inclined conical surfaces unhindered by the upward flow of liquid. Intermittent operation has the advantage that it can improve the speed at which the cells slide downwardly, thereby improving cell viability and productivity. In a specific embodiment, a pump is used to direct a liquid suspension of cells from a bioreactor or fermentation media into the settler devices of the present disclosure.

In certain embodiments of these methods, the clarified liquid collected from the settler device includes at least one of biological molecules, organic or inorganic compounds, chemical reactants, and chemical reaction products. In certain embodiments of these methods, the clarified liquid collected from the settler device includes at least one of hydrocarbons, polypeptides, proteins, alcohols, fatty acids, hormones, carbohydrates, antibodies, isoprenoids, biodiesel, and beer. In certain embodiments of these methods, the clarified liquid collected from the settler device includes at least one of insulin or its analogs, monoclonal antibodies, growth factors, sub-unit vaccines, viruses, virus-like particles, colony stimulating factors and erythropoietin (EPO).

Figure 10:
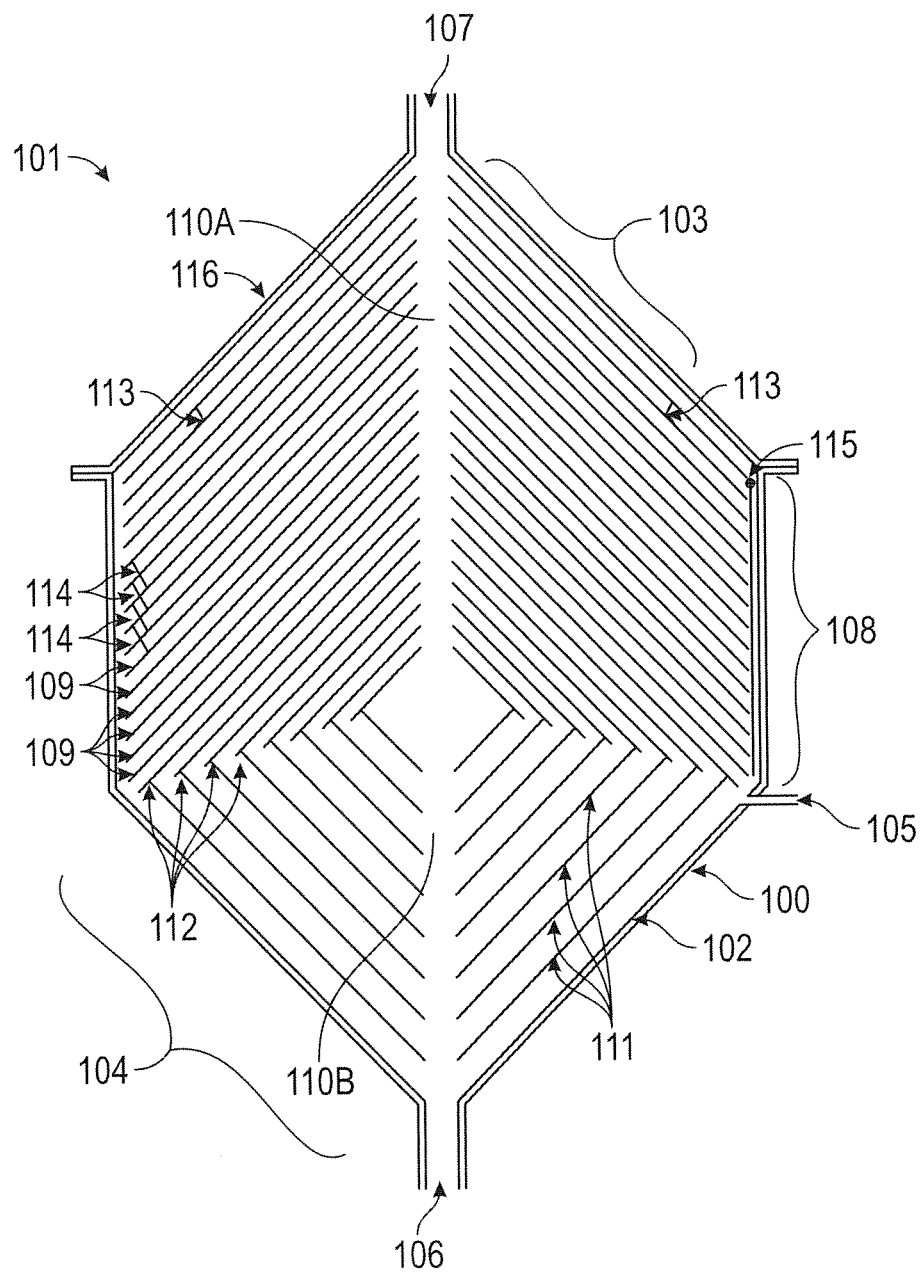
FIG. 10 is a sectional view through a settler device of this disclosure, including a first and second stack of cones arranged in opposite orientations, apex to base, inside a cyclone housing.

Referring now to FIG. 10, which is a cross-sectional view of a cylindrical inclined settler device of this disclosure, an embodiment of the settling devices of this disclosure includes: an outer wall (100) of a cyclone housing (101), which includes an optional fluid jacket (102), a first, upper conical portion (103) of the cyclone housing (101), a second, lower conical portion (104) of the cyclone housing (101), a vertical (or generally cylindrical) portion (108) of the cyclone housing (101), located between the first, upper conical portion (103) and the second, lower conical portion (104), with the optional fluid jacket (102) extending to conical portions (103) and/or (104), and vertical portion (108), of the cyclone housing, an inlet (105) for a liquid (for example, cell culture media) entering the cyclone housing (101), which inlet (105) extends through the optional fluid jacket (102), a bottom outlet port (106) for returning concentrated liquid (for example, a concentrated cell culture liquid containing settled cells) back to a bioreactor or other vessels such as harvest or collection or holding tanks, and a top outlet port (107) for harvesting a clarified liquid (for example, culture liquid containing very few cells, which are mostly smaller dead cells and cell debris).

A first stack of cones (109) is located within the outer wall (100) of the cyclone housing, occupying the first, upper conical portion (103) and at least part of the vertical portion (108) of the cyclone housing (101). The first stack of cones (109) is generally centered around a substantially central opening (110) in the first stack of cones (109). Each of the cones in the first stack of cones (109) illustrated in FIG. 10, are truncated cones (i.e., the shape is "truncoconical") as the apex of each cone is truncated to form an opening that, in conjunction with the other cones in the first stack of cones (109), forms the central opening (110). As depicted in FIG. 10, the cones (109) comprising the first stack of cones (109) are arranged within the outer wall (100) of the cyclone housing (101) with the truncated apex of each cone (109) oriented towards the top outlet port (107) and the open base of the cone oriented towards the bottom outlet port (106).

A second stack of cones (111) is optionally located within the outer wall (100) of the cyclone housing (101), occupying the second, lower conical portion (104) and at least part of the vertical portion (108) of the cyclone housing (108) and generally centered around the central opening (110) in the second stack of cones (111). The central opening (110) extends from the first stack of cones (109). Similarly, each of the cones in the second stack of cones (111) illustrated in FIG. 10, are truncated cones, and the apex of each cone is truncated to form an opening that, in conjunction with the other cones in the second stack of cones (111), continues the central opening (110). As depicted in FIG. 10, the cones comprising the second stack of cones (111) are arranged within the outer wall (100) of the cyclone housing with the open base of each cone oriented towards the top outlet port (107) and the truncated apex of the cone oriented towards the bottom outlet port (106), (i.e., the open bases of the first stack of cones (109) is oriented in the opposite direction of the second stack of cones (111)). In one embodiment, the opening (110B) formed by the truncated apex of each cone (111) in the second stack of cones has about the same diameter as the opening (110A) formed by the truncated apex of each cone (109) of the first stack of cones.

As illustrated in FIG. 10, at least one of the cones in the first stack of cones (109) is attached to a cone in the second stack of cones (111). Such attachment is typically proximate an end of both the cone in the first stack of cones (109) and the cone in the second stack of cones (111), opposite the central opening (110). In one embodiment, the attachment may be configured to form an extension or overlap (112) of the at least one cone in the first stack of cones (109) at the point of attachment to the cone in the second stack of cones (111).

The cones comprising the first stack of cones (109) and the second stack of cones (111), may include a projection (113) supporting the next successive cone in the stack. These projections (113) are preferably placed at a constant distance and are formed at an equal size to hold each successive cone in the stack at about an equal spacing between all of the cones in the stacks. At least three projections (113) are needed for each cone to properly support each successive cone, but each cone may comprise more than three projections (113), as needed to adequately or properly support the cone (only two such projections (113) are illustrated in the cross-sectional view of FIG. 10). For example, each cone may comprise between four and eight projections (113), or may comprise more than eight projections (113), to support the next successive cone in the stack. The projections (113) are attached to at least one surface of a cone, but these projections do not attach to another cone in a stack of cones. Thus, these projections do not attach two or more cones in a stack of cones to one another. The projections (113) extend from at least one surface of a cone to support the next successive cone in the stack, or to support the cone above the next successive cone in the stack (i.e., the projections may extend above a cone, or extend below a cone, or extend both above and below a cone). The projections are typically of uniform size such that the projections support each cone in the first and second stack of cones (109 and 111) at a substantially uniform distance between each cone in the stack.

The projections may be configured as pins (114) that extend from a surface of a cone to support each successive cone in a stack of cones. Such pins may project at an angle between about 30 degrees to about 120 degrees from the surface of the cone. In a preferred configuration, illustrated in FIG. 10, the pins (114) project both above and below the surface of at least one cone in a stack of cones, at an angle of about 90 degrees from the surface of the cone, to support the next successive cone in the stack, and to support the cone above the next successive cone in the stack.

In another embodiment, the pins (114) may optionally have an "L" shape or a triangular shape. The L-shaped and/or triangular spacers (114) may be interconnected to an upper surface of each cone (109) that is distal to port 106. The L-shaped spacers (114) include a first side interconnected to a second side at an apex. In one embodiment, the L-shaped spacers (114) and/or triangular spacers (114) are interconnected to the upper surface such that the first side supports the next successive cone (109) in the stack. The second side is substantially parallel to the surface of the cone (109). Optionally, the second side may project beyond the cone (109) to space the first stack of cones (109) a predetermined distance from an interior surface of the wall (100) of cyclone housing (101). In one embodiment, the L-shaped spacers and the triangular spacers (114) have a substantially thin cross-section to prevent or minimize interference with the movement or flow of liquid and suspended particles within the cyclone housing (101). Optionally, the L-shaped spacers and/or the triangular spacers may be integrally formed with the cones (109). In another embodiment, the L-shaped spacers and/or the triangular spacers are separately formed and subsequently interconnected to the cones (109).

A cylindrical inclined settler device of this disclosure may optionally include at least one spacer configured to prevent a stack of cones residing within the outer wall (100) of the cyclone housing from shifting to touch the interior walls of the cyclone housing. As illustrated in FIG. 10, spacer (115) extends along the end of the first stack of cones (109) opposite the central opening (110), and approximately parallel to the outer wall (100) of the cyclone housing. In this configuration, the spacer (115) prevents the first stack of cones (109) from shifting or falling against the vertical portion (108) of the cyclone housing, for example if the cyclone housing (101) is set on its side or inverted while the stacks of cones remain inside the cyclone housing. The spacer (115) may be formed as a ring that encircles the circumference of the cyclone housing with three or more "legs" that extend substantially parallel to the vertical portion of the cyclone housing (108), thereby supporting the stacks of cones on several sides.

The spacer (115), formed as a ring that encircles the circumference of the cyclone housing as described above, may be attached to at least one rod at a first point of attachment. The at least one rod extends substantially parallel to the vertical portion of the cyclone housing (108), horizontally across the cyclone housing, and again substantially parallel to the vertical portion of the cyclone housing (108) to attach to the spacer (115) at a second point of attachment, on a side substantially opposite the first point of attachment. This spacer (115), attached to at least one rod is shown in the cross-sectional view of the settler devices depicted in FIGS. 12A, 12B, 13, 14A, 14B, 14C (137, 144, 151, 159 respectively). These rods may support an upper, first stack of cones independently from the lower, second stack of cones.

As depicted in FIGS. 13, 14A, 14B, and 14C, this configuration allows the settler devices of this disclosure to be constructed and used with only an upper, first stack of cones (109), i.e., without a lower, second stack of cones below the rod (151 and 159). In these configurations, the lower conical portion (104) of the cyclone housing (152 and 160) may act as a receptacle or incubator for live cells. Thus, in this configuration, port (145 and 153) may function to supply liquids and/or gasses, as needed to support the growth of cells. Thus, such chemicals as cellular growth nutrients, pH modifying chemicals and buffers, and oxygen, nitrogen, or carbon dioxide may be added or removed from port (145 and 153). Similarly, bottom outlet port (146 and 154), may also function as an inlet or outlet port for the introduction and/or removal of such liquids or gasses.

The settler devices illustrated in FIGS. 10-14C may include a means to control the temperature of the settler device, such as a reservoir for cooling or heating fluids to be circulated around all or part of the outer wall of the settler device. Thus, an optional fluid jacket (102) may be included on the outside of the cyclone housing. Water or other fluids may be directed into the fluid jacket (102) to maintain the cyclone housing and all of its contents within a desired temperature range. Ports may be formed in the outer wall (100) of the cyclone housing, to reach the jacket (102). The ports may function as inlet or outlet ports for the circulation of cooling or heating fluids through the jacket.

As depicted in FIG. 10, the settler devices of this disclosure may include a closure or lid (116) over at least one end of the settler device opposite the bottom outlet port (106). The closure (116) may also include a port (107) for removing liquids from, or entering liquids into, the settler device. The top outlet port (107) and any additional ports or outlets in the lid are in liquid communication with the outside and the inside of the settler device to allow the passage of liquids/gases into and/or out of the settler device, and in each instance of such opening or inlet/outlet, these passage ways into and out of the cyclone housing may include valves or other mechanisms that can be opened or closed to stop or restrict the flow of liquids/gases into or out of the settler devices of this disclosure.

As depicted in FIG. 10, the lid (116) covering the settler device may be concave, rising to a central core point. The angle of rise in the concave lid (116) may be between about 20 degrees and about 60 degrees. In another embodiment, the concave lid (116) rises at an angle of between about 30 degrees and about 50 degrees. Gas, bubbles, froth or the like may accumulate in this space and a tube may be attached to an opening in the settler device or through top outlet port (107) to withdraw such gasses, etc. from the space beneath the top of the settler device. Similarly, fluid or gas may be pumped into the settler device through such tube that is inserted through an opening in the settler device or through an opening in the lid (116). The lid (116) may be attached to the settler device by one or more screws, and may be secured in place over the settler device over an o-ring.

Figure 11:
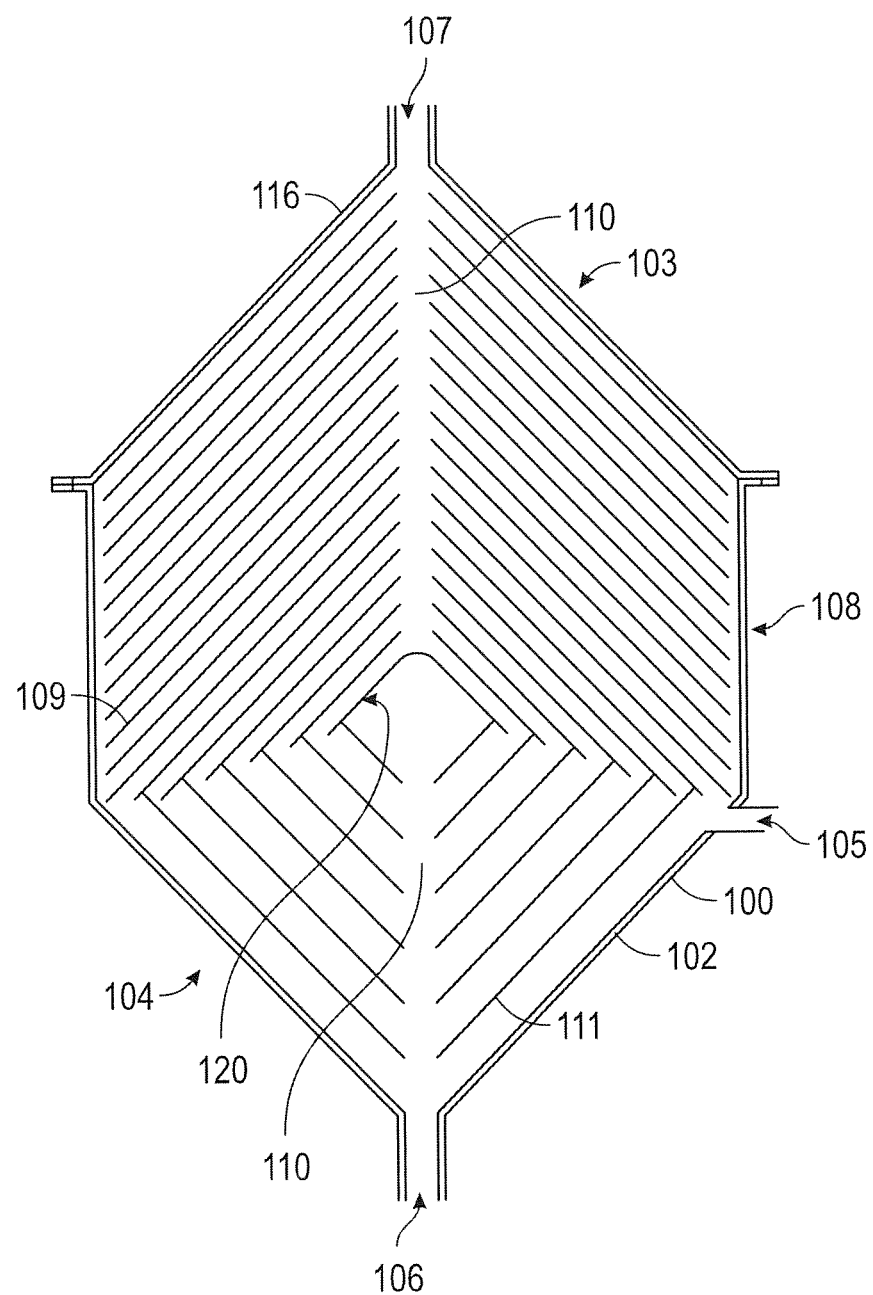
FIG. 11 is a sectional view of a settler device of this disclosure, including at least one cone from the first stack of cones that is not truncated at the apex.

As depicted in FIG. 11, one or more cones (120) in the first stack of cones (109) located within the outer wall (100) of the cyclone housing, occupying the first, upper conical portion (103) and at least part of the vertical (or cylindrical) portion (108) of the cyclone housing, and generally centered around a central opening (110) in the first stack of cones (109), may be devoid of a central opening, or may have a much smaller central opening than other cones in this first stack of cones. These cones (120) may direct particles or cells settling within the central opening (110) to the surfaces of cones in the first stack of cones (109). These cones (120) may also direct particles or cells settling within the central opening (110) to the surfaces of cones residing in the second stack of cones (111). Similar to the settler device depicted in FIG. 10, second stack of cones (111) is arranged with the truncated apex of each cone oriented towards the bottom outlet port (106) and the open base of the cone oriented towards the top outlet port (107)). In one embodiment of the cyclone housings of FIGS. 10, 11, spacing between the cones of the first stack of cones (109) is substantially the same as the spacing between the cones of the second stack of cones (111). Optionally, in another embodiment cyclone housings of FIGS. 10, 11, the space between the cones of the first stack of cones (109) is one of greater than and less than the spacing between the cones of the second stack of cones (111).

Figure 12A:
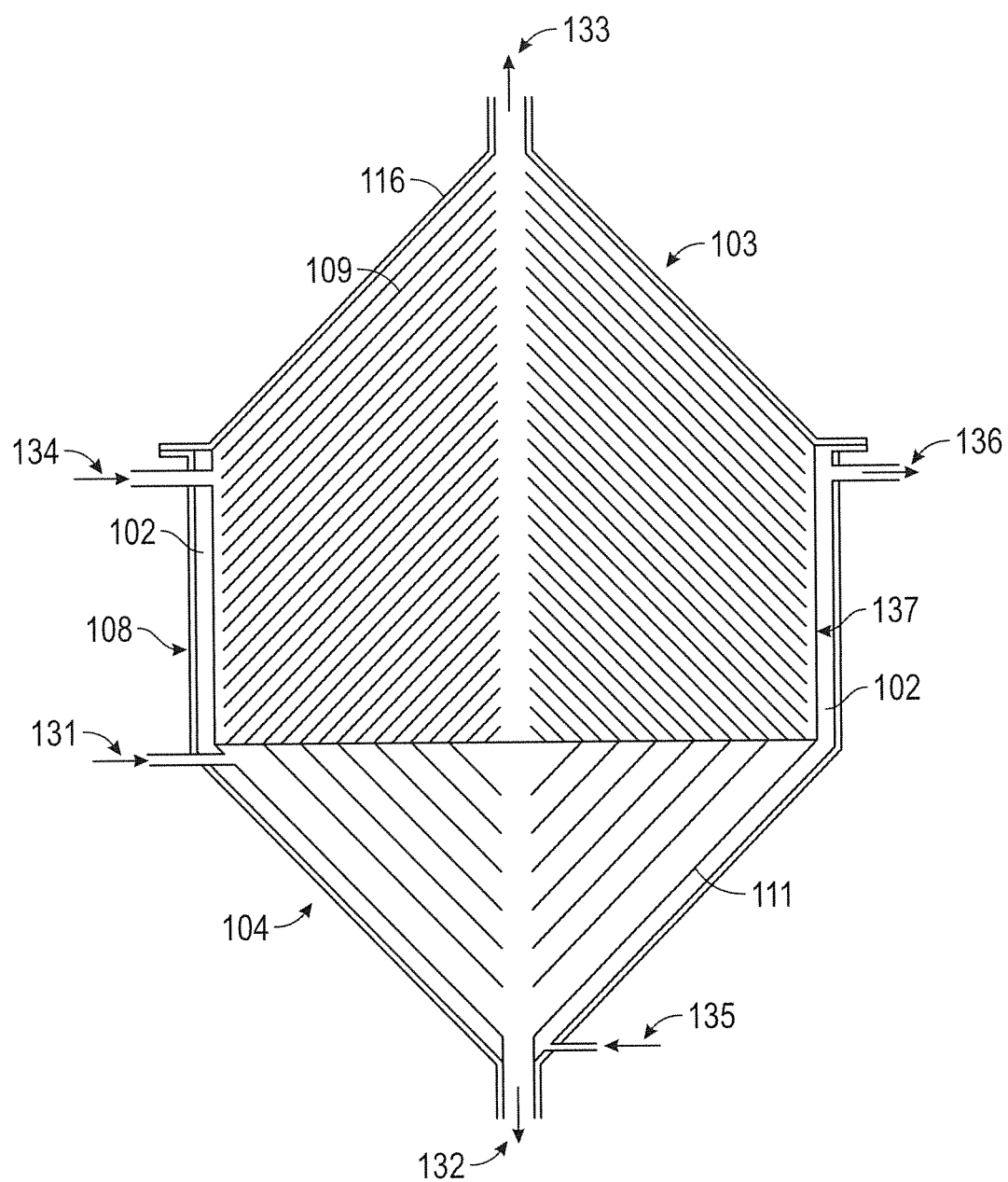
FIG. 12A is a sectional view of another configuration of a settler device of this disclosure in which the top and bottom stack of cones have different separation distances between successive cones in each stack.
Figure 12B:
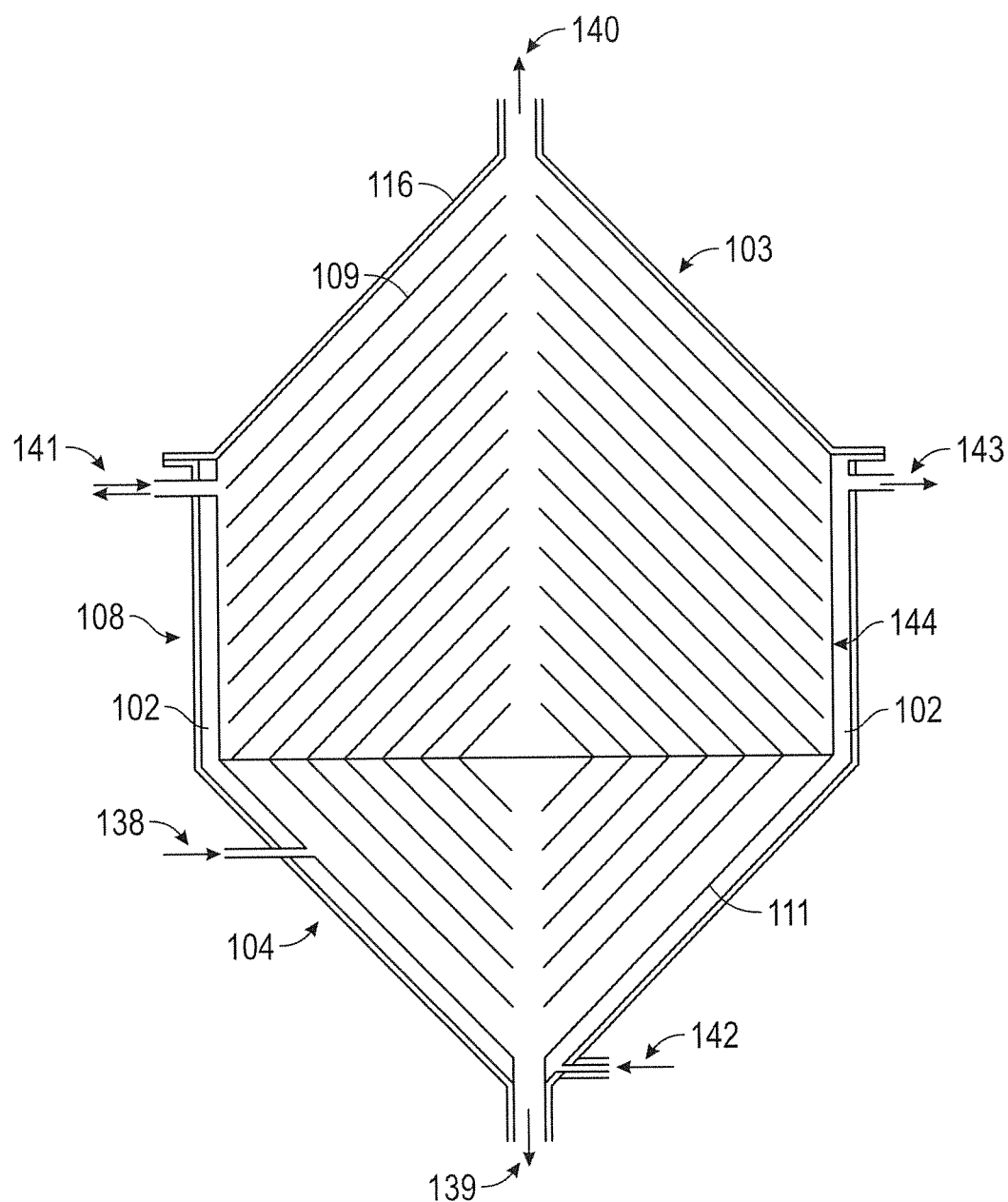
FIG. 12B is a sectional view of another configuration of a settler device of this disclosure that may function as a cell retention device attached to a perfusion bioreactor.

FIGS. 12A and 12B depict another configuration of a settler device of this disclosure. The devices illustrated of FIGS. 12A and 12B, which depict cross-sectional views of a cell or particle retention device that may be attached to a perfusion bioreactor, include: an inlet (131 and 138) of cell culture liquid that may be pumped in continuously from the perfusion bioreactor, an outlet port (132 and 139) from which concentrated settled cells flow out and are returned to a bioreactor, a top outlet port (133 and 140) from which clarified culture fluid flows, which fluid may contain a secreted product, as well as some of the not-yet settled smaller dead cells and cellular debris, an optional second inlet (134 and 141) from the bioreactor, which inlet may pass gas and/or cellular culture media, a first port (135 and 142) for cooling/heating fluid to an optional fluid jacket, and a second port (136 and 143) to the fluid jacket. In one embodiment, the first port (135, 142) is an inlet into the optional fluid jacket and the second port (136, 143) is an outlet from the optional fluid jacket.

In these examples of a settler device of this disclosure, cell culture liquid from a bioreactor is pumped into the settler via the tangential inlet port (131 and 138) near the top of the bottom conical section (104). Any gas in the liquid inlet can be easily separated with a t-junction on the inlet line and the upper line carrying mostly the gas with some cell culture liquid can be inlet via the upper tangential port (134 and 141) near the top of the cylindrical portion (108) of the settlers. The clarified harvest output containing the secreted protein is harvested continuously from the top outlet (133 and 140) of the cell retention device, while the concentrated cells from the bottom outlet (132 and 139) are recycled back to the bioreactor, resulting in a high cell density perfusion bioreactor that can be operated indefinitely, i.e. over several months of continuous perfusion operation. The continuous high titer harvest from a single, 1000-liter, high cell density perfusion bioreactor can easily exceed the accumulated production from a large (>20,000 liter) fed-batch bioreactor on an annual basis.

As illustrated in FIG. 12A, the spacing between the cones in the first and second stacks (109, 111) can be different. This may be advantageous, for example when it may be desirable to have liquid flow be larger in the bottom section (104), and cell separation in the top or first stack of cones (109) is more efficient with smaller spacing than is typically required for the bottom stack of cones (111). As illustrated in FIG. 12B, the spacing between the cones in the first and second stacks (109, 111) can be the same or substantially the same, allowing for similar flow rates for liquid and particles or cells in both stacks of cones.

Figure 13:
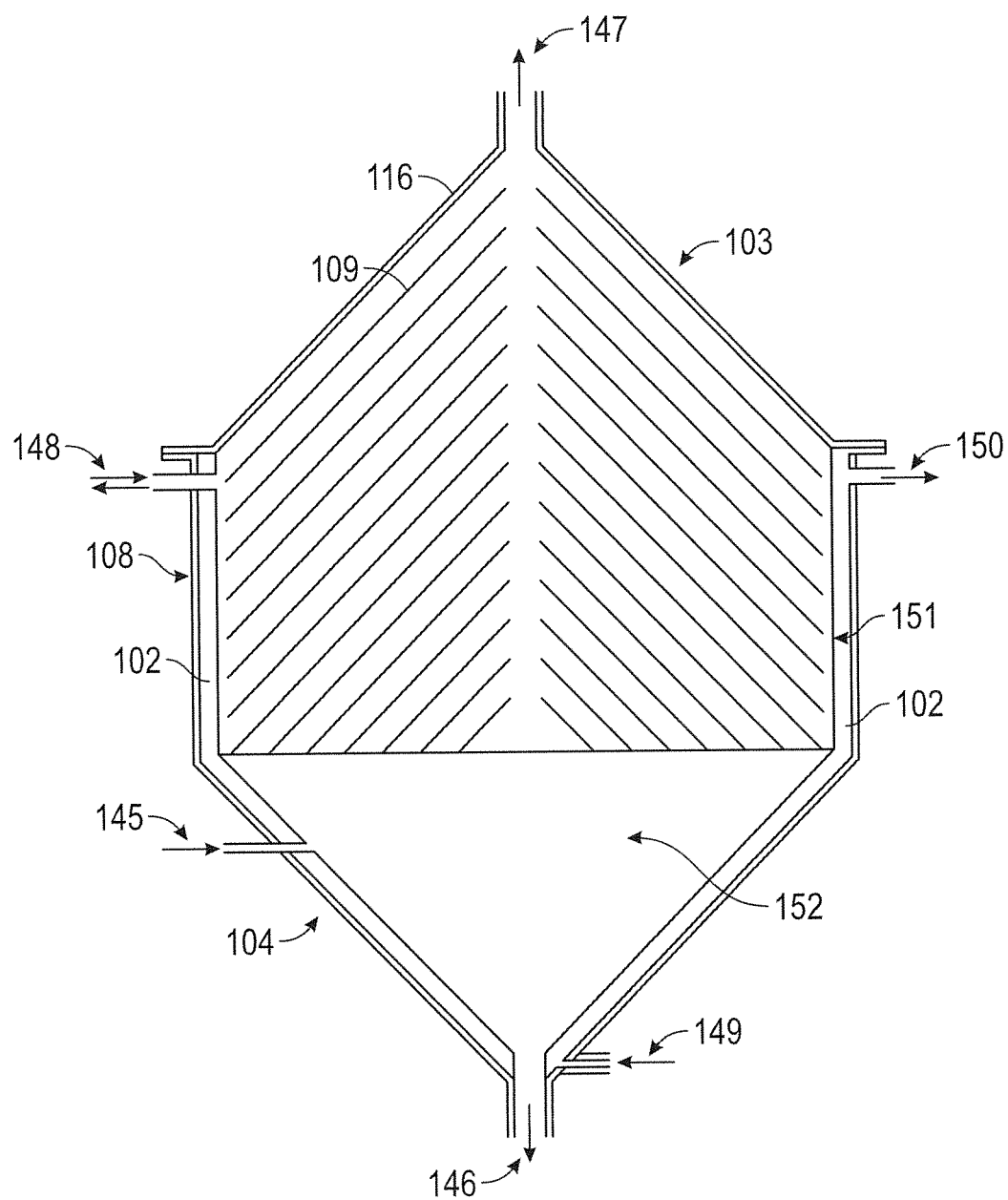
FIG. 13 is a sectional view of another configuration of a settler device of this disclosure including only a first stack of cones supported on at least one rod.
Figure 14A:
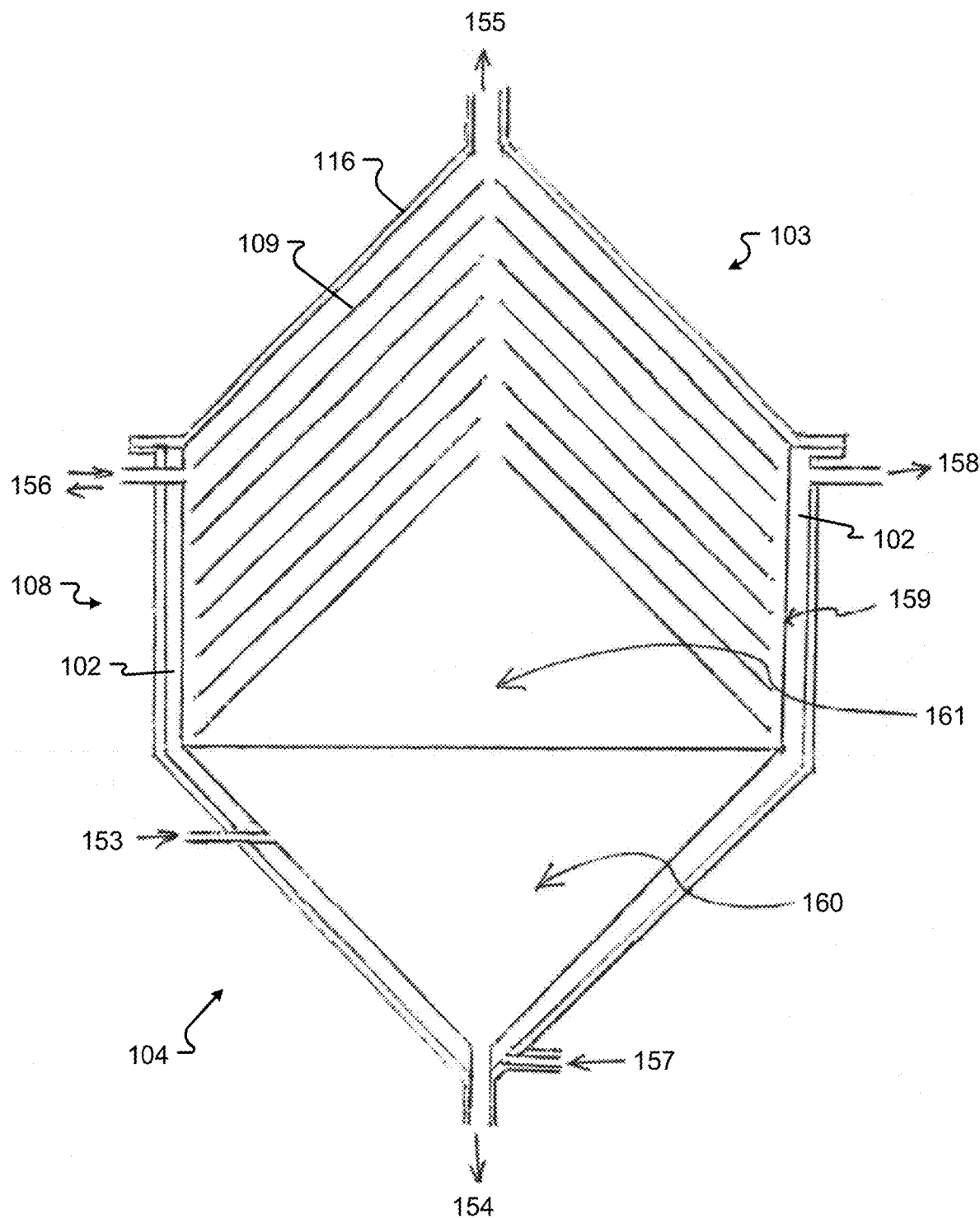
FIG. 14A is a sectional view of another configuration of a settler device of this disclosure including only a first stack of substantially equal-sized cones supported on at least one rod.
Figure 14B:
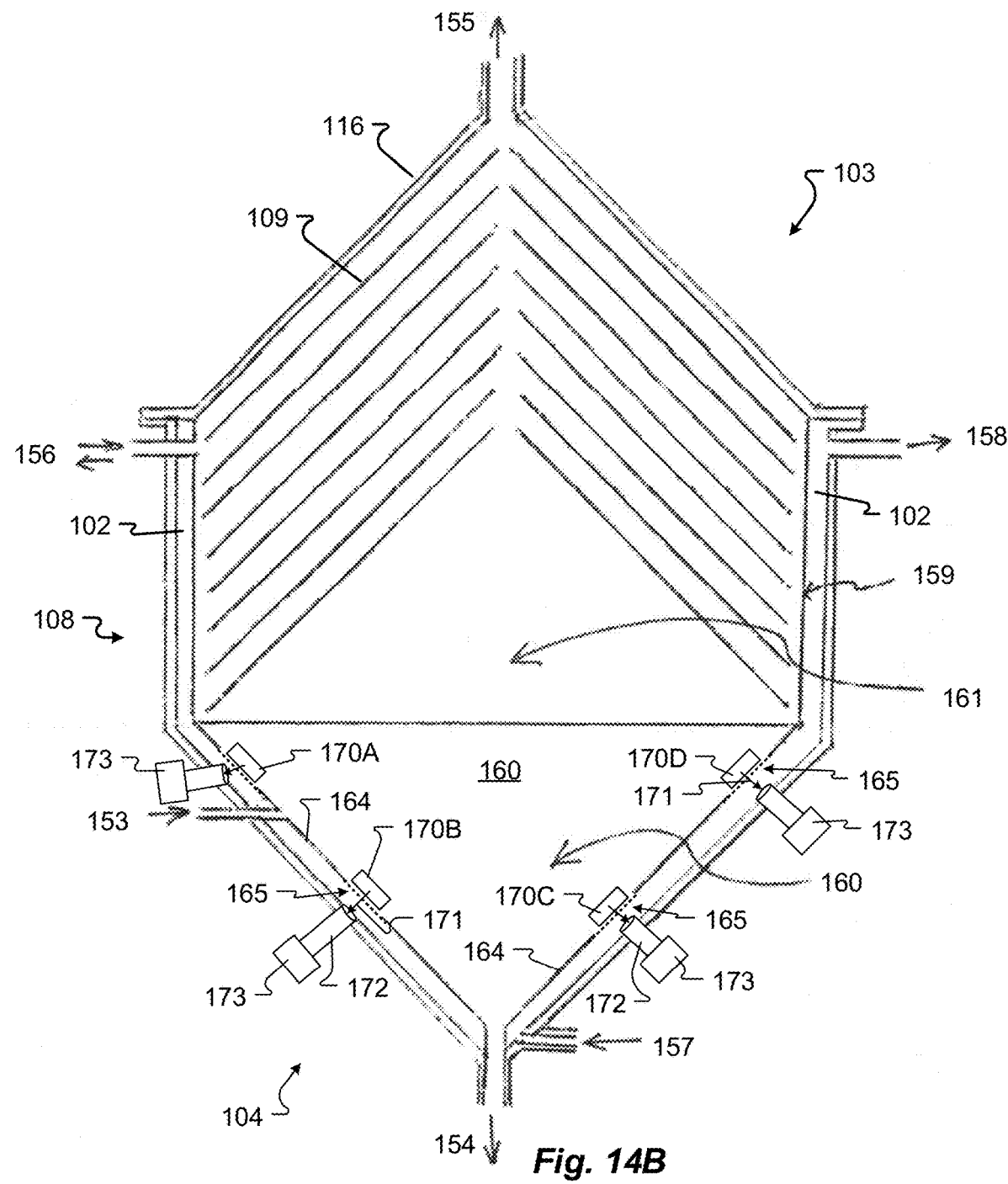
FIG. 14B is a sectional view of a settler device of an embodiment of this disclosure similar to the settler device of FIG. 5A but which includes at least one sensor within the lower conical portion of the cyclone housing.

FIGS. 13, 14A and 14B, depict cross-sectional views of a cell or particle separation devices that can function as a stand-alone perfusion bioreactor for the in vitro expansion of mammalian cells, such as stem cells and CAR-T cells for autologous cell therapy. In these examples of settler devices of this disclosure, inlet of serum-free or animal protein-free cell culture medium may be pumped continuously into the settler/perfusion bioreactor, through bottom port (146 and 154) and/or side port (145 and 153). A controlled mixture of $O_2$, $CO_2$, and $N_2$ may also be pumped in to control the pH and DO of the culture supernatant inside the settler/bioreactor. At the end of in vitro cell expansion, the concentrated settled cells collecting at the bottom can be harvested from bottom port (146 and 154).

Clarified culture fluid containing any metabolic waste products, such as ammonia and lactate, or gasses, along with any not-yet settled smaller dead cells and cell debris, may be removed through top port (147 and 155). Optional liquid outlet (148 and 156) from the bioreactor may be used for sampling bioreactor contents, for example to check cell viability, and continuous measurement of liquid pH and DO for inputs into a computer-controlled multi-gas mass flow controller. Cooling/heating fluid may be directed into (or out of) a first port (149 and 157) to the fluid jacket (102) and flow out from (or into) a second port (150 and 158) to the fluid jacket (102).

FIG. 13 depicts a configuration of the compact cell settler device that can function as a stand-alone perfusion bioreactor in which the lower conical portion (104) of the cyclone housing (152) is empty of a second stack of cones and may thus house cells in culture. The surface of the cyclone housing at least in the lower conical portion of the cyclone housing (152) may comprise a plastic, and/or may be coated with a plastic or other material that supports the growth of cells in culture.

FIG. 14A depicts another possible configuration of the compact cell settler device that can function as a stand-alone perfusion bioreactor in which the lower conical portion (104) of the cyclone housing (160) and at least part of the vertical portion (108) of the cyclone housing (161) are empty of a stack of cones and may thus house cells in culture. The surface of the cyclone housing at least in the lower conical portion of the cyclone housing and the vertical portion of the cyclone housing (160 and 161) may comprise a plastic, and/or may be coated with a plastic or other material that supports the growth of cells in culture.

During operation of the settler devices of the embodiments depicted in FIGS. 13 and 14A, inlet of serum-free or animal protein-free cell culture medium is pumped continuously into the settler/perfusion bioreactor, through bottom port (146, 154) and/or side port (145, 153). A controlled mixture of $O_2$, $CO_2$, and $N_2$ may also be pumped in to control the pH and DO of the culture supernatant inside the settler/bioreactor. At the end of in vitro cell expansion, the concentrated settled cells collecting at the bottom can be harvested from bottom port (146, 154). Clarified culture fluid containing any metabolic waste products, such as ammonia and lactate, or gasses, along with any not-yet settled smaller dead cells and cell debris, may be removed through top port (147, 155). Optional liquid outlet (148, 156) from the bioreactor may be used for sampling bioreactor contents, for example to check cell viability, and continuous measurement of liquid pH and DO for inputs into a computer-controlled multi-gas mass flow controller.

FIG. 14B depicts another compact cell settler device of the present disclosure which is similar to the device of FIG. 14A. The cell settler device may be used as a stand-along bioreactor/cell sorter combination. Accordingly, the cell settler device of the embodiment of FIG. 14B may be used without the perfusion bioreactor described in conjunction with FIG. 15.

Sensors (170) are positioned within the cyclone housing (160). In one embodiment, the sensors (170) are arranged on an interior surface (164) of the cyclone housing (160). As describe above, the surface (164) of the cyclone housing at least in the lower conical portion (104) may comprise a plastic. In one embodiment, the plastic is transparent or at least translucent. Optionally, at least a portion of the cyclone housing (160) is transparent or translucent. For example, a portion (165) of transparent or translucent material may be interconnected to an aperture in the surface (164) of the cyclone housing similar to a window. The transparent portion (165) may comprise glass, plastic, or any other suitable material. The transparent portion (165) may be formed of a material which is transparent to light of a predetermined range or ranges of wavelengths.

Figure 15:
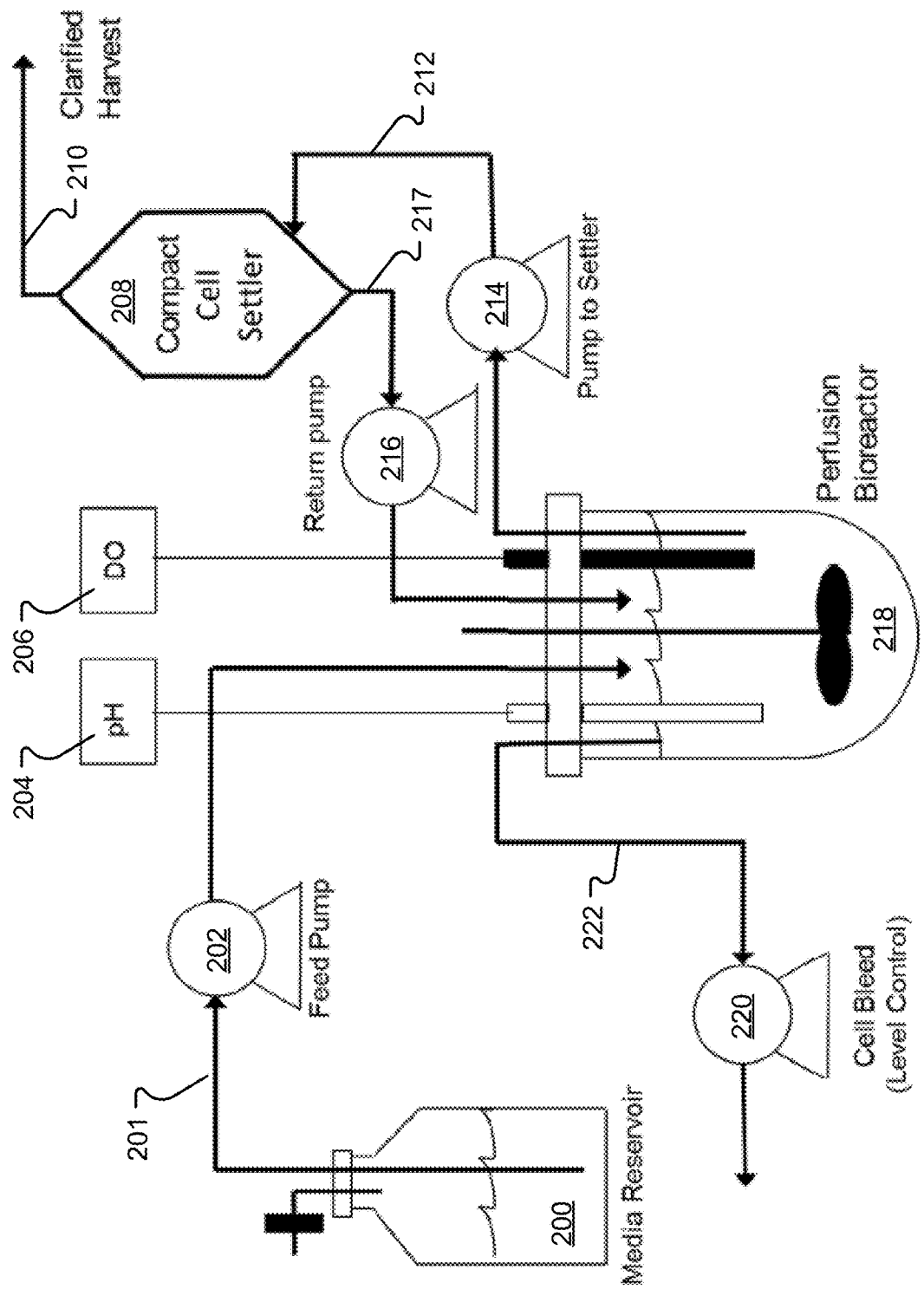
FIG. 15 is a schematic representation of the attachment of a compact cell/particle settler device of this disclosure to a modular bioreactor.

The sensors (170) are in contact with media within the cyclone housing (160). Each sensor (170) is operable to monitor one or more of pH, DO, Glucose, temperature, and $CO_2$ (including dissolved or partial $CO_2$) in the cyclone housing (160). Growth media may be added to the cyclone housing (160) through side port (153). In this manner, the embodiment of the compact cell settler device illustrated in FIG. 14B may be used as a bioreactor without an external modular bioreactor such as illustrated in FIG. 15.

In one embodiment, each sensor (170) measures one of pH, DO, Glucose, temperature, and $CO_2$. Optionally, one or more of the sensors may comprise a fluorescent probe. As one of skill in the art will appreciate, the fluorescent probes (170) emit light (171) that varies based on a condition sensed by the probe. The light (171) passes through the surface (164) or the transparent portion (165) and is collected by a reader or meter (173). Optionally, the light may be collected by an optional fiber cable (172) and transmitted to the meter (173). The meter (173) is operable to report or display levels of at least one of pH, DO, Glucose, temperature, and $CO_2$ sensed by the fluorescent probes (170).

The fluorescent probes (170) may be affixed in a variety of different positions within the cyclone housing (160). Thus, the probes (170) can be arranged to measure different conditions, or changes of conditions, at different areas of the cyclone housing. In one embodiment, the probes (170) are spaced from ports (153, 154) of the cyclone housing (160).

In one embodiment, the stand-along bioreactor/cell sorter combination illustrated in FIG. 14B can be fabricated in single-use disposable plastic. Alternatively, the stand-along bioreactor/cell sorter combination of the embodiment of FIG. 14B can be manufactured of more durable stainless steel for larger scale perfusion bioreactors. Like all embodiments of the present disclosure, the device of FIG. 14B may be scaled to any desired size.

Figure 14C:
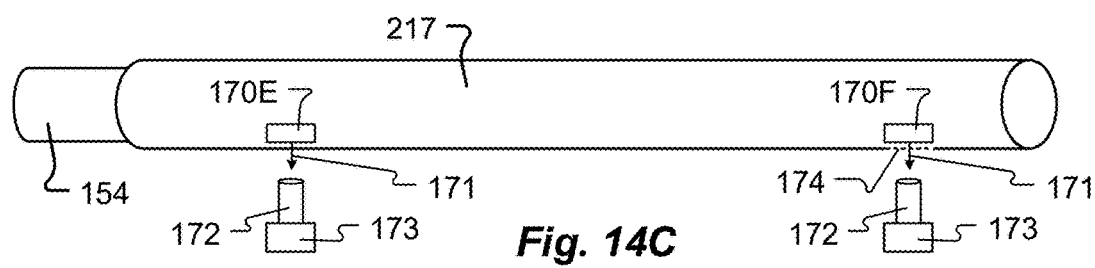
FIG. 14C is a section view of a line configured to be interconnected to a settler device of the present disclosure, the line including at least one sensor.

Referring now to FIG. 14C, a partial view of a line (217) that may be interconnected to any of the compact cell settler devices of the present disclosure is illustrated. The line (217) may have a diameter or otherwise be configured to interconnect to any port (4, 6, 9, 24, 26, 29, 39, 40, 41, 84, 85, 86, 105, 106, 107, 131, 132, 133, 134, 138, 139, 140, 141, 145, 146, 147, 148, 153, 154, 155, 156) of embodiments of the present disclosure. The line (217) may optionally include at least one sensor (170E, 170F) positioned within a hollow interior. The sensors (170E, 170F) are in contact with fluid and/or particles within the line (217). Optionally, the sensors (170E, 170F) are arranged on an interior surface of the line (217) although other configurations are contemplated.

Sensors (170E, 170F) may be the same as, or similar to, the sensors (170) described in conjunction with FIG. 14B. Accordingly, each sensor (170E, 170F) is operable to monitor one or more of pH, DO, Glucose, temperature, and $CO_2$ (including dissolved or partial $CO_2$) in the line (217). In one embodiment, each sensor (170E, 170F) measures one of pH, DO, Glucose, temperature, and $CO_2$.

Optionally, one or more of the sensors (170E, 170F) may comprise a fluorescent probe which emits light (171) that varies based on a condition sensed by the probe (170E, 170F). The light (171) is collected by a reader or meter (173). Optionally, the light (171) may be collected by an optional fiber cable (172) and transmitted to the meter (173). The meter (173) is operable to report or display levels of at least one of pH, DO, Glucose, temperature, and $CO_2$ sensed by the fluorescent probes (170E, 170F).

In one embodiment, line (217) may comprise a material that is transparent or at least translucent. Thus, light (171) generated by sensor (170E) may pass through the line (217). In another embodiment, at least a portion (174) of the line (217) is transparent or translucent, similar to a window. Accordingly, light (171) generated by the sensor (170F) may be transmitted through window portion (174) and collected by meter (173).

Methods of Use and Operation of Processes

Referring now to the settling device depicted in FIGS. 10 and 11 of this disclosure, exemplary methods of using the settling devices are described. A particle containing liquid (including, for example, cell culture liquid, waste water or reaction fluid containing solid catalyst particles, etc.) is introduced tangentially into a device of this disclosure though the port (105). Approximately 50%-99% of the entering liquid (typically about 90%) is removed through the bottom port (106), while the remaining 1%-50% (typically about 10%) of the liquid is removed through the top port (107). A pump (such as a peristaltic pump) may be used to suck liquid out of this top port (107), while the concentrated liquid exiting the bottom may be allowed to exit the bottom outlet (106) of the cyclone housing due to gravity, without the need for a pump. Alternately, the liquid containing the settled cells or particles, may be pumped out from the bottom port (106) of the conical settler at about 50%-99% of entering liquid flow rate, and the remaining clarified liquid (1-50%) may exit via the top port (107). Optionally, fluid exiting port (107) may be pumped out into a harvest line.

Most of the entering cells (or particles) are pushed against the walls of this assembly (100) through centrifugal forces upon entry, settle down the conical portion through a gentle vortex motion initially, getting faster as the liquid and particles/cells go down and exit via the bottom port (106). Cells or particles which have not settled will move up through the stacks of cones (109 and 111). As the liquid moves slowly up through the stacks of cones (109 and 111), bigger particles (e.g., live cells) will settle on the surfaces of the cones and either slide down the cones or fall down the small spacing provided between the cones and the outer walls of the cyclone housing (100). These settled particles fall down vertically along the outer cylindrical walls until they reach the bottom conical section of the assembly (104) and proceed to slide down the conical section to the bottom port (106).

By increasing the liquid inlet flow rate through port (105), it is possible to reduce the residence time of liquid inside the inclined settling zones such that smaller particles (for example dead cells and cellular debris) will not have settled by the time the liquid reaches the top of the settling zone, and therefore these smaller particles exit the settling device via the top port (107). This feature provides a simple method to remove smaller particles (such as dead cells and cellular debris) selectively via the top port (107) into a harvest stream, while larger particles (such as live and productive cells) are returned from the bottom port (106) to another vessel (such as a bioreactor).

Thus, in these methods, the step of introducing a liquid suspension into these settler devices may include directing a liquid suspension from a plastic bioreactor bag into the particle settling device.

Liquid may be directed into, or drawn out of, any of the ports or openings (105, 106, 107) in the settling device by one or more pumps (for example a peristaltic pump) in liquid communication with the port or opening. Such pumps, or other means causing the liquid to flow into or out of the settler devices, may operate continuously or intermittently. If operated intermittently, during the period when the pump is off, settling of particles or cells occurs while the surrounding fluid is still. This allows those particles or cells that have already settled to slide down the inclined conical surfaces unhindered by the upward flow of liquid. Intermittent operation has the advantage that it can improve the speed at which the cells slide downwardly, thereby improving cell viability and productivity. In a specific embodiment, a pump is used to direct a liquid suspension of cells from a bioreactor or fermentation media into the settler devices of the present disclosure.

One parameter that may be adjusted in these methods of using the settler devices of this disclosure is the liquid flow rate into and out of the settler devices. The liquid flow rate will depend entirely on the particular application of the device and the rate can be varied in order to protect the particles being settled and separated from the clarified liquid. Specifically, the flow rate may need to be adjusted to protect the viability of living cells that may be separated in the settler devices of this disclosure and returned to a cell culture, but the flow rate should also be adjusted to prevent substantial cell or particle build up in the settler devices or clogging of the conduits that transfer liquid into and out of the settler devices.

In examples of these methods, the clarified liquid collected from the settler device includes at least one of biological molecules, organic or inorganic compounds, chemical reactants, and chemical reaction products. In certain embodiments of these methods, the clarified liquid collected from the settler device includes at least one of hydrocarbons, polypeptides, proteins, alcohols, fatty acids, hormones, carbohydrates, antibodies, isoprenoids, biodiesel, and beer. In examples of these methods, the clarified liquid collected from the settler device includes at least one of insulin or its analogs, monoclonal antibodies, growth factors, sub-unit vaccines, viruses, virus-like particles, colony stimulating factors and erythropoietin (EPO).

Each publication or patent cited herein is incorporated herein by reference in its entirety. The settling devices of the present disclosure now being generally described will be more readily understood by reference to the following examples, which are included merely for the purposes of illustration of certain aspects of the embodiments of the present disclosure. The examples are not intended to limit the disclosure, as one of skill in the art would recognize from the above teachings and the following examples that other techniques and methods can satisfy the claims and can be employed without departing from the scope of the present disclosure.

EXAMPLES

Example 1: Yeast or Other Microbial Cells Secreting Protein Products

Recombinant microbial cells, such as yeast or fungal (*Pichia pastoris, Saccharomyces cerevisiae, Kluyveromyces lactis, Aspergillus niger*, etc.) or bacterial (*Escherichia coli, Bacillus subtilis*, etc.) cells, which have been engineered to secrete heterologous proteins (for example, insulin or brazzein) or naturally secreting enzymes (e.g. *A. niger, B. subtilis*, etc.) can be grown in bioreactors attached to the compact settler device of this disclosure, to recycle live and productive cells back to the bioreactor, which will thereby achieve high cell densities and high productivities. Fresh nutrient media is continuously supplied to the live and productive cells inside the high cell density bioreactors and the secreted proteins or enzymes are continuously harvested in the clarified outlet from the top port (or top-side outlets as shown in FIGS. 5, 6 and 7), while the concentrated live and productive cells are returned back to the bioreactor. As dead cells and a small fraction of live cells are continuously removed from the bioreactor via the harvest outlet, cell growth and protein production can be maintained indefinitely, without any real need for terminating the bioreactor operation. In operations using yeast *Pichia* cells with the conical settler devices of this disclosure, the perfusion bioreactor has been operated for over a month. As the microbial cells grow in suspension culture and the cell retention device can be scaled up to any desired size, this disclosure can be attached to suspension bioreactors of sizes varying from lab scale (<1 liter) to industrial scale (>50,000 liters) or any size therebetween to achieve high cell density perfusion cultures.

In one specific example, a perfusion bioreactor culture of yeast *Pichia pastoris* cells is described. Yeast *Pichia pastoris* cells were grown in a 5-liter, computer-controlled bioreactor, initially in batch mode to grow the cells from the inoculum for the first 50 hours, then in fed-batch mode to fill up the attached 12-liter cell settler slowly for the next 100 hours, and then in continuous perfusion mode with a compact cell settler of this disclosure to remove the smaller dead cells and recycle the larger live cells back into the bioreactor. A typical schematic of the attachment of a compact cell/particle settler of this disclosure to any modular bioreactor is shown in FIG. 15.

Referring to FIG. 15, the yeast *Pichia pastoris* cells were grown in a perfusion bioreactor (218). Growth media was added to the bioreactor (218) from media reservoir (200) via a first pump (202) interconnected to input line (201). Dissolved oxygen content and pH were continuously monitored in the bioreactor (218) by dissolved oxygen monitor (206) and pH monitor (204). Yeast cell culture from the bioreactor (218) was delivered to a 12-liter compact cell settler (208) of the present disclosure via a second pump (214) interconnect to line (212). Effluent from the compact cell settler (208), which contained smaller dead cells, was evacuated by effluent line (210). Larger live cells were recycled from the cell settler (208) back to the bioreactor (218) via third pump (216) and return line (217). Media and cell culture levels in the bioreactor (218) were controlled by removing excess cell culture via fourth pump (220) and removal line (222) to be captured or discarded.

Figure 16:
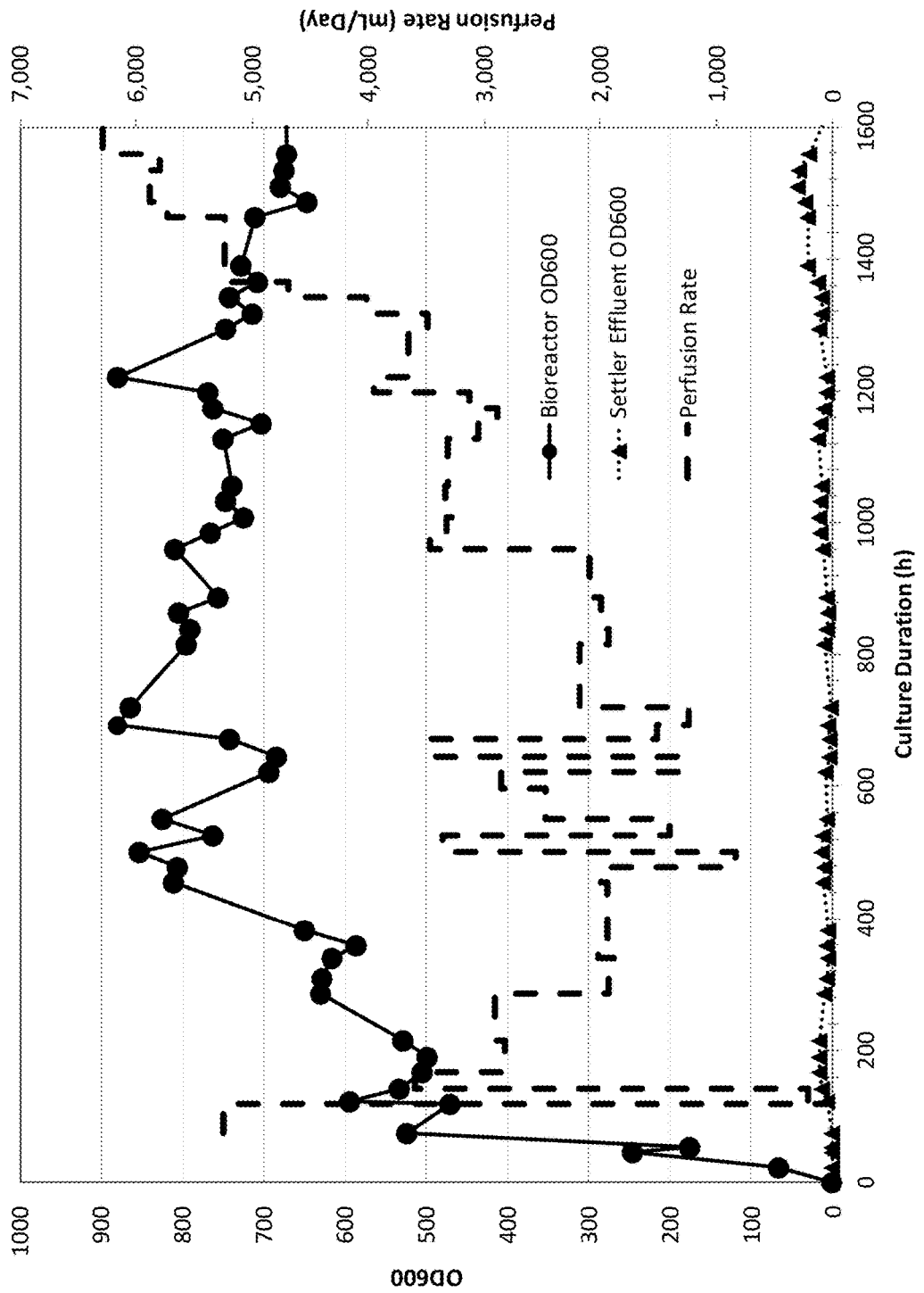
FIG. 16 is a graph which shows results of perfusion bioreactor culture of yeast *P. pastoris* cells, with a fully packed compact cell settler as the cell retention device and set up as depicted in FIG. 15.

Results obtained with this perfusion bioreactor set up with a compact cell/particle settler of this disclosure are shown in FIG. 16. The circles show the optical density of bioreactor samples, measured at 600 nm, building up during the initial batch and fed-batch culture period of about 150 hours, followed by continuous perfusion operation up to 1600 hours or longer than 2 months. The settler effluent or harvest rate is adjusted by manipulating either settler inlet pump setting and/or settler recycle pump setting. The cell concentration (as measured by OD at 600 nm) and the size distribution are determined by the harvest flow rate and cell size distribution of the cells entering from the bioreactor and other factors such as the recycle ratio from the settler. The effluent stream contains very little cells, as measured by the very low OD's in the range from 0 to 30, even as the perfusion rate is gradually increased from 2000 ml/day to over 6,000 ml/day. These results demonstrate that very high cell density was obtained and maintained in the bioreactor due to the recycle of most of the live cells back to the bioreactor and selective removal of smaller dead cells and cell debris. Even at these increasing perfusion rates, the bioreactor can be operated indefinitely at high cell density without any reason to terminate the bioreactor, such as clogged membranes in competing membrane based cell retention devices.

Figure 17:
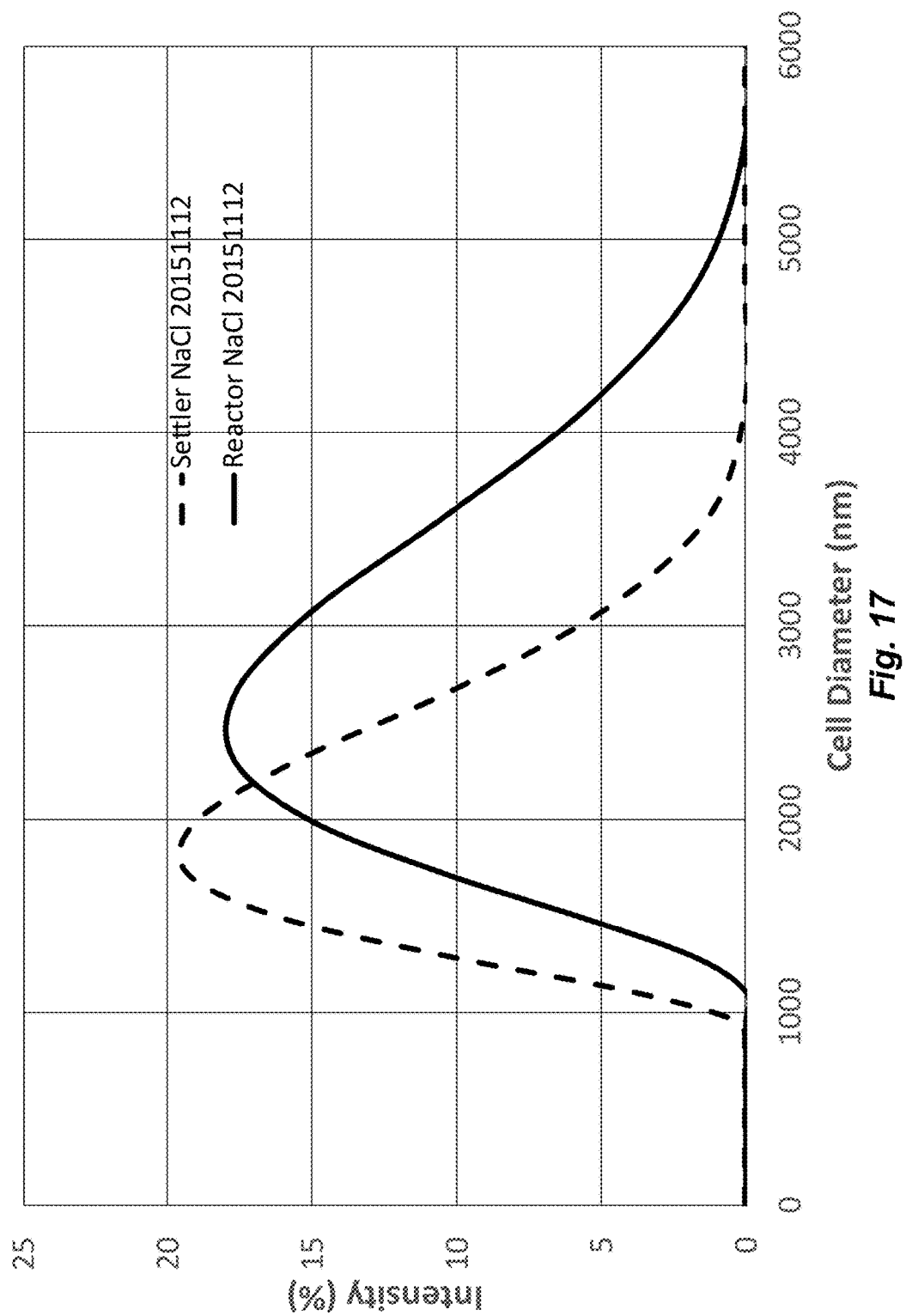
FIG. 17 shows particle size analysis of samples taken from the bioreactor and settler effluent from the apparatus set up as depicted in FIG. 15.

Samples from the bioreactor and settler effluent taken at the same time point were analyzed with a particle size analyzer. The normalized cell size distribution results shown in FIG. 17 clearly indicate that the settler effluent contains a significantly smaller cell size distribution compared to that found for the cells in the bioreactor. These results demonstrate that the settler removed the smaller dead cells and any cell debris preferentially in the effluent, while the larger live cells are preferentially returned to the bioreactor. Thus, the bioreactor is continuously cleaned by selective removal of dead cells and cell debris by the settler effluent and consequently there is no accumulation of dead cells and cell debris within the bioreactor, as happens routinely with all other cell retention devices.

Figure 18:
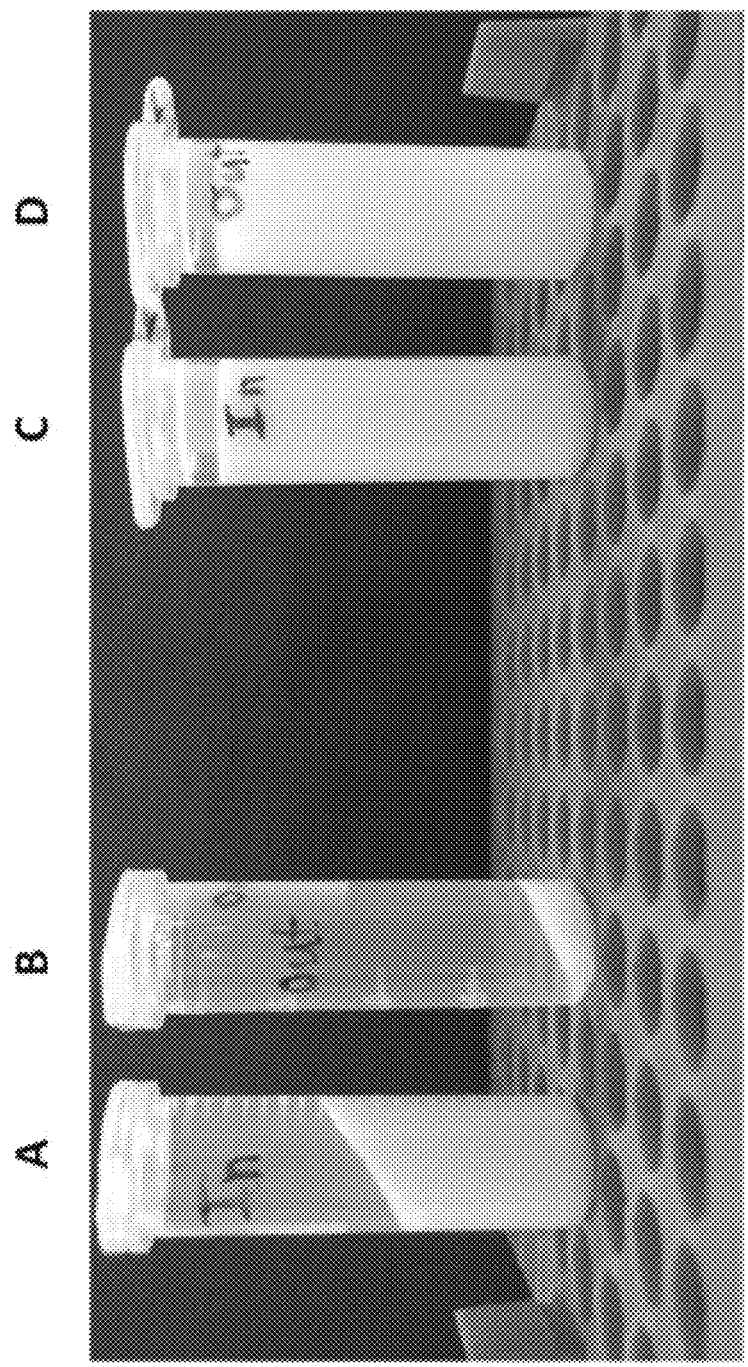
FIG. 18 shows centrifuge vials containing samples of effluent from the settler device (tube labeled 'D'), and from within the bioreactor (tube labeled 'C'), and, following centrifugation, cell pellets from effluent from the settler device (tube labeled 'B'), and cells pelleted from within the bioreactor (tube labeled 'A')

The bioreactor and settler effluent samples from an early time point during the perfusion culture were collected and centrifuged in small 2 ml vials. FIG. 18 shows centrifuge vials containing samples of effluent from the settler device (208) (tube labeled 'D') and from within the bioreactor (218) (tube labeled 'C') and the cell pellets following centrifugation: cells pelleted from effluent from the settler device (208) (tube labeled 'B') and cells pelleted from within the bioreactor (218) (tube labeled 'A'). The pelleted cells from the bioreactor occupy almost 50% of the wet packed cell volume in the vial (tube "A"), while the pelleted cells in the settler effluent occupy only about 5% of the wet packed cell volume of tube "B". These results again confirm that only a very small fraction of the intact smaller cells from the bioreactor are removed in settler effluent while most of the larger intact cells are preferentially returned to the bioreactor.

Figure 19:
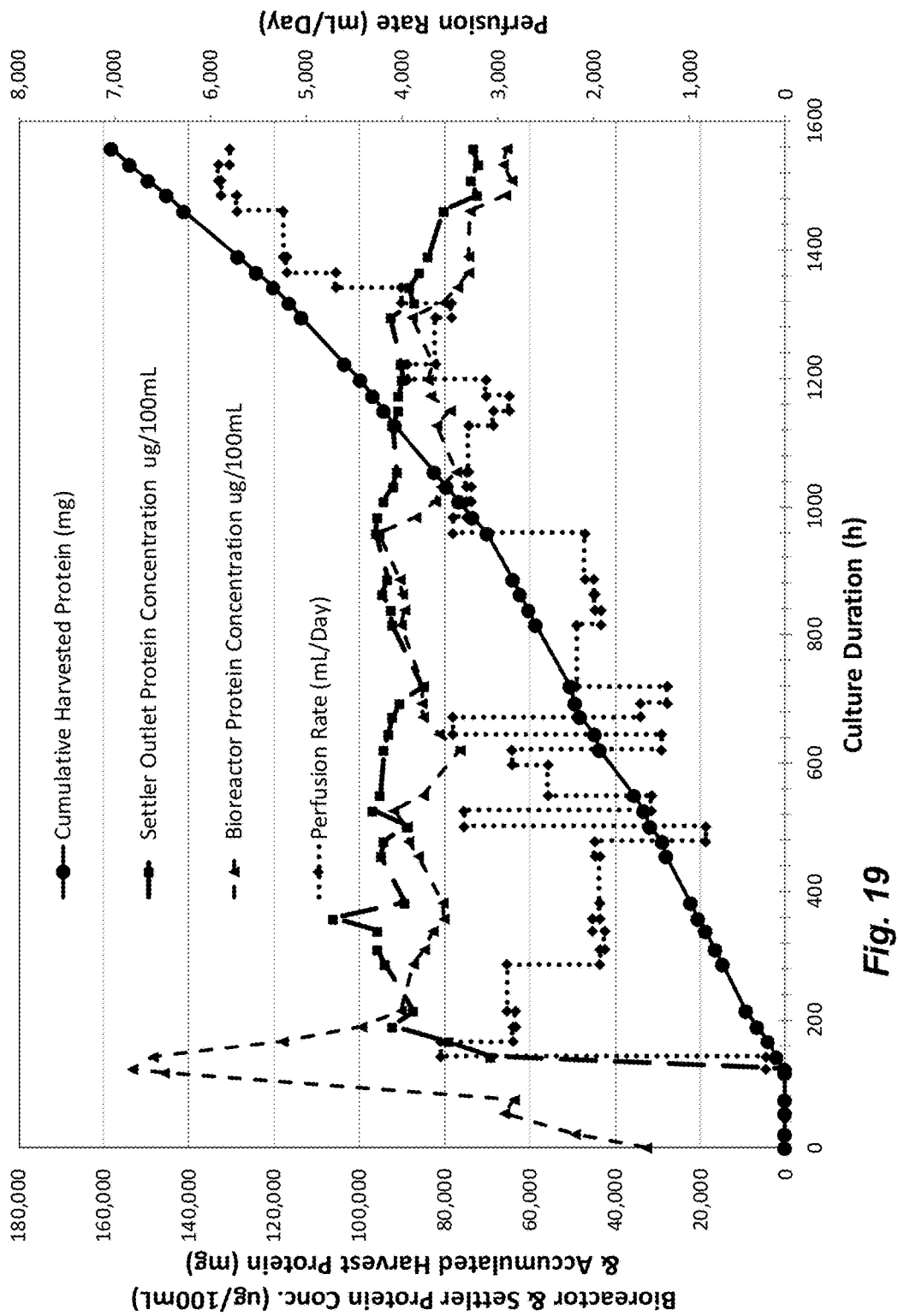
FIG. 19 is a graph of total protein concentrations in bioreactor and settler effluent and cumulative harvested protein.

Total protein concentrations in the bioreactor and settler effluent during this 2 month long perfusion operation were measured and shown in FIG. 19. These results show that after the initial batch and fed-batch operation, i.e. during the prolonged perfusion operation, total protein content in the effluent sample (squares) from the settler device (208) is consistently greater than the total protein content in the sample from the bioreactor (218) (triangles). These results suggest very strongly that there is no protein sieving inside the settler (208), as is commonly observed with membrane-based cell retention devices such as ATF in perfusion cultures of mammalian cells. Further these results suggest that there is some additional protein production in the settler (208), causing the effluent protein concentrations to be consistently higher than those in the bioreactor (218) at the same time.

The total accumulated protein in the harvest stream (circles) from the continuous perfusion bioreactor configuration illustrated in FIG. 15 can be compared with protein can be harvested in the cell-free supernatant of a single fed-batch bioreactor (218) performed over 158 hours or almost 6 days, and repeated again and again over the same culture duration of say 1600 hours. While fed-batch cultures typically have a long downtime to harvest or empty the bioreactor, clean the internal surfaces, sterilize in situ with steam, cool, refill the bioreactor with sterile medium, inoculate the bioreactor with fresh cells and then allow the cells to grow to high enough cell density to see significant increase in the protein titer, the continuous perfusion bioreactor continues to operate uninterrupted at high cell density and high production rate throughout the culture operation. Consequently, the total accumulated protein in the continuously harvested product stream is increasing, at a significantly faster rate as the perfusion rate is increased, and accumulates to 160 g, 5× higher protein amount than can be harvested in the cell-free supernatants from 8 repeated fed-batch culture operations in the same 5 liter bioreactor.

Example 2: Removing Yeast Cells from Beer

In large-scale brewing operations, yeast cells are removed from the product beer by filtration devices, which regularly get clogged, or centrifugation devices, which are expensive high-speed mechanical devices. Previously, hydrocyclones were unsuccessfully tested for this application (Yuan et al., 1996; Cilliers and Harrison, 1997). These devices can be readily replaced by the settler devices of this disclosure to clarify beer from the top outlets and remove the concentrated yeast cell suspension from the bottom outlet. Due to the increased residence time and enhanced sedimentation in the conical settler zones of this disclosure, the inventor has achieved successful separation of yeast cells from cell culture liquid, harvesting the culture supernatant containing only about 5% of the cells entering the settler device in its first operation. As the device can be scaled up or down to increase or decrease its cell separation efficiency, it is feasible to obtain completely cell-free beer from the harvest port, if desired. Thus, the devices of this disclosure may be particularly useful in brewing beer, as well as clarifying beer, and in continuous brewing arrangements.

Example 3: Mammalian Cell Perfusion Cultures

Enhanced sedimentation of murine hybridoma and recombinant mammalian cells in inclined settlers have already been demonstrated successfully (Batt et al., 1990 and Searles et al., 1994) and scaled up in lamellar settlers (Thompson and Wilson, U.S. Pat. No. 5,817,505, 1998). While the lamellar settlers are scaled up in three dimensions independently, a conical settler device of this disclosure can be scaled up in three dimensions simultaneously by simply increasing its radius, as discussed above. Thus, the settlers of this disclosure are more compact, contain much more inclined surfaces for settling on a smaller footprint, and are more easily scalable cell retention devices with proven applications in mammalian cell cultures secreting glycoproteins, such as monoclonal antibodies, and other therapeutic proteins. The clarified harvest output from the top port containing the secreted protein is harvested continuously from the cell retention device, while the concentrated cells from the bottom outlet are recycled back to the bioreactor, resulting in a high cell density perfusion bioreactor, that can be operated indefinitely, (i.e. over several months of continuous perfusion operation). The continuous high titer harvest from a single, 1000-liter, high cell density perfusion bioreactor can be more than the accumulated production from a large (>20,000 liter) fed-batch bioreactor on an annual basis.

Figure 20:
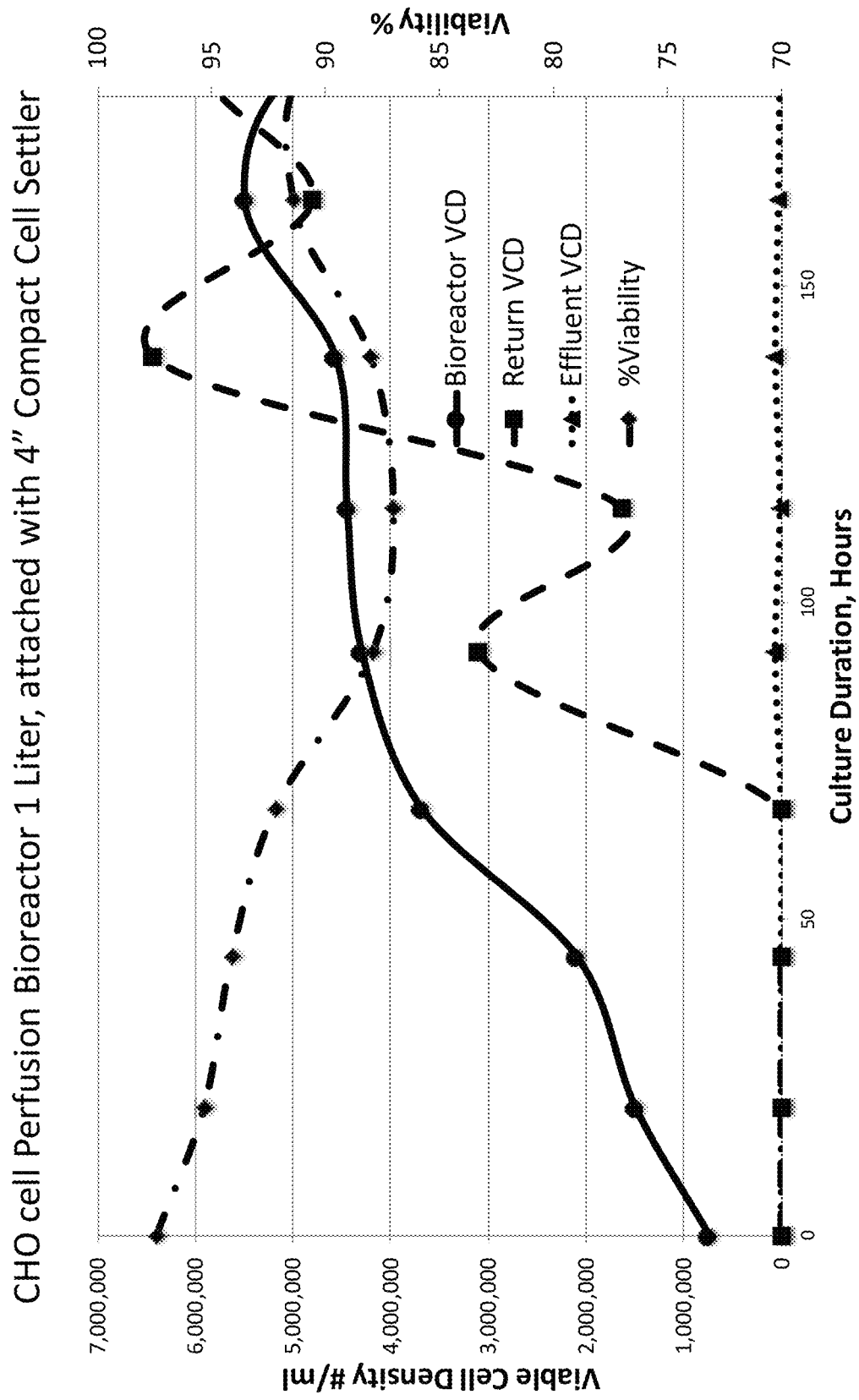
FIG. 20 is a graph of Chinese hamster ovary (CHO) cell perfusion bioreactor 1 Liter interconnected to a 4" compact cell settler of the present disclosure.

Recombinant Chinese hamster ovary cells, which are used commonly in the overexpression and secretion of therapeutic glycoproteins, are cultured in a 1-liter controlled bioreactor attached with a 4" compact cell settler (FIG. 14A), as shown schematically in FIG. 15. Viable cell densities in the bioreactor (circles), settler top effluent (triangles) and settler bottom return to the bioreactor (squares) are shown in FIG. 20. Soon after the perfusion operation starts at 60 hours, we can see that very few live cells are removed from the settler top effluent and increasing amount of viable cells are being returned to the bioreactor from the settler bottom outlet. Consequently the bioreactor viable cell density (VCD) is increasing gradually after the perfusion operation begins and more dramatically the viability percentage (diamonds) in the bioreactor increases when the perfusion begins.

Figure 21:
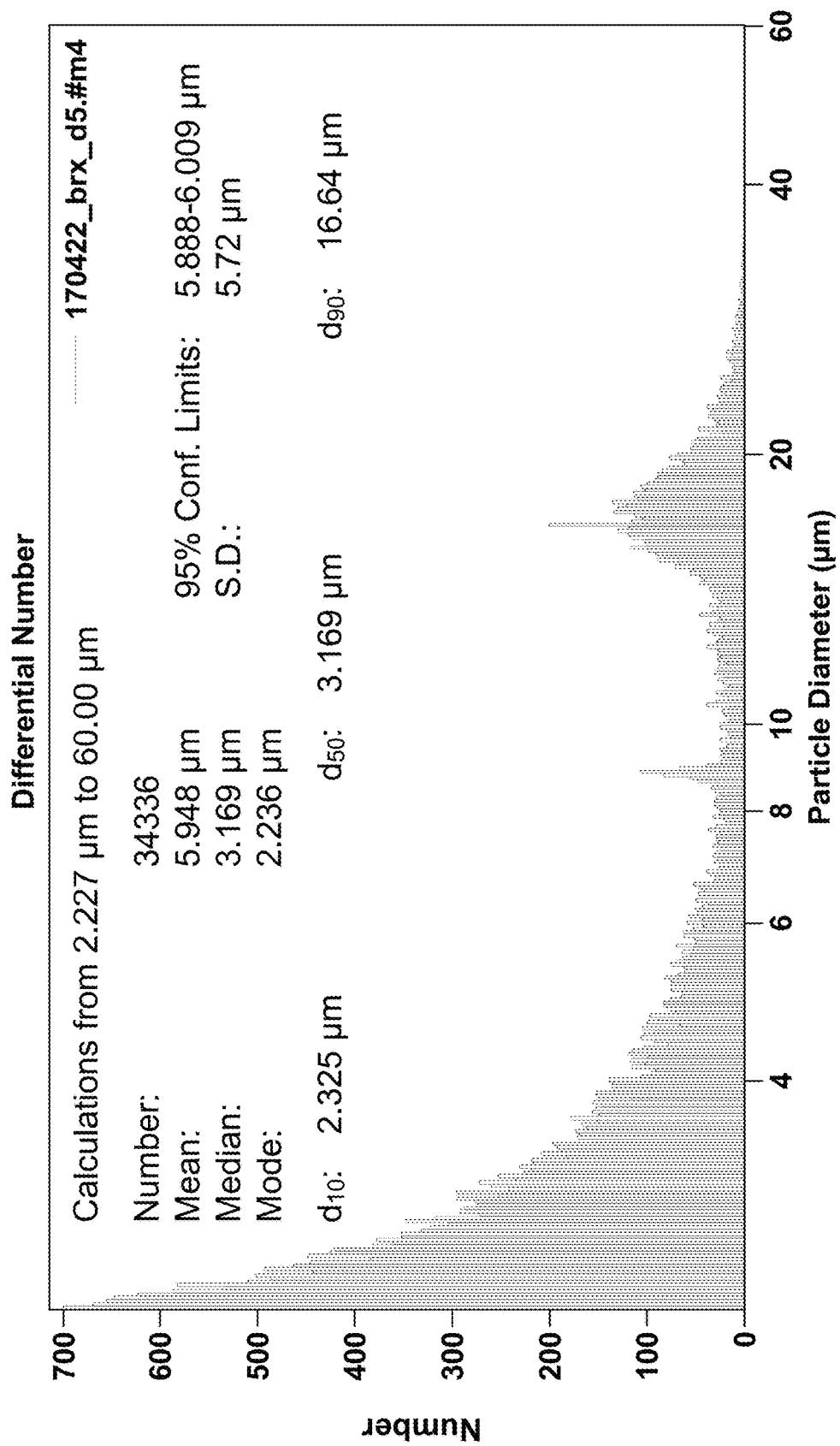
FIG. 21 is a histogram of cell/particle sizes of samples taken on day 5 from a bioreactor configured as shown in FIG. 15.
Figure 22:
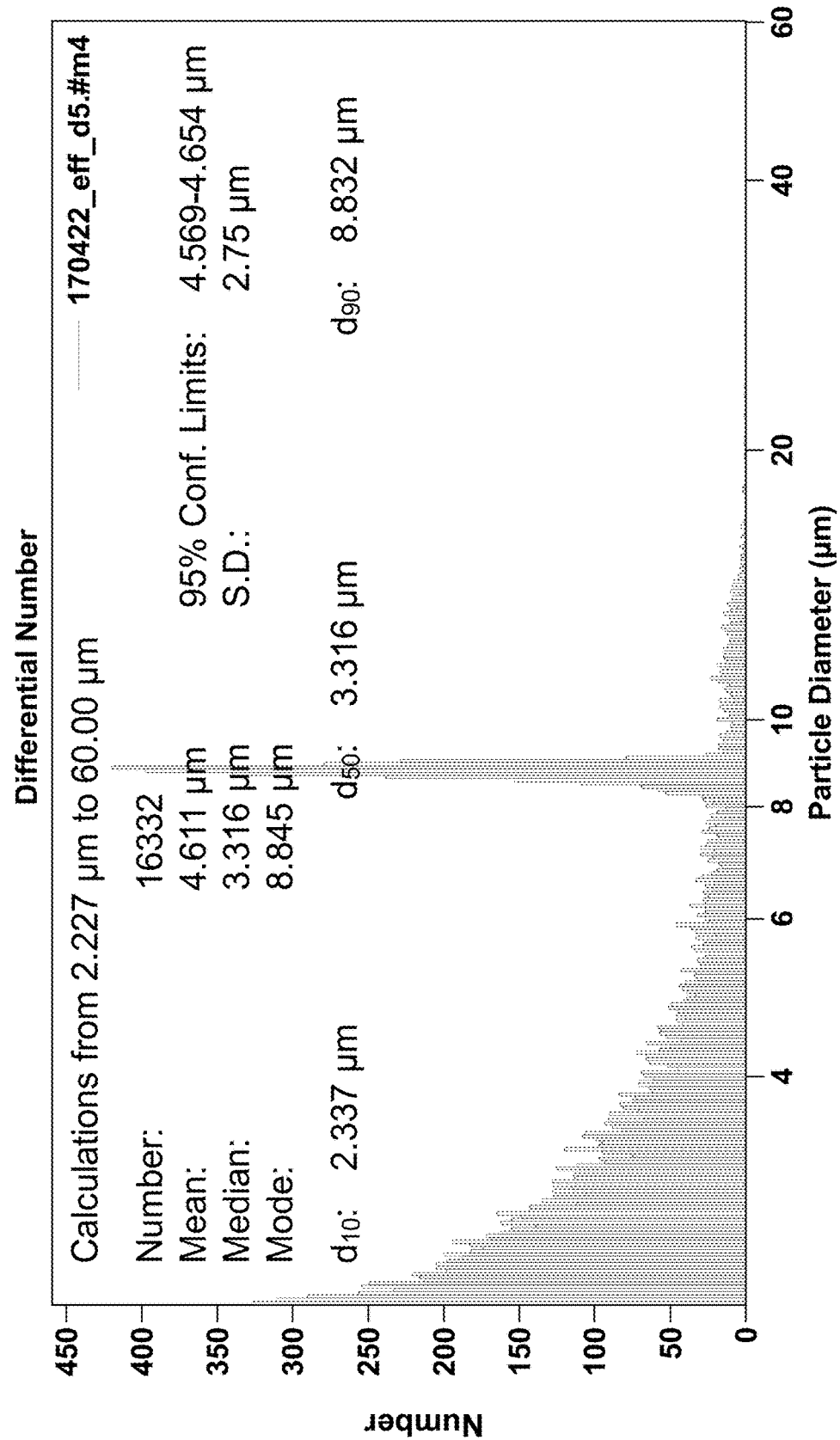
FIG. 22 is another histogram of cell/particle sizes of samples taken on day 5 from a top port of a cell settler device of the present disclosure interconnected to a profusion bioreactor as shown in FIG. 15.

Cell size distributions were measured on samples from the bioreactor and settler top effluent on day 5 and shown in FIGS. 21 and 22 respectively. FIG. 21 represents a histogram of cell/particle sizes measured by a Beckman-Coulter Multisize Analyzer for the bioreactor sample, showing a broad distribution of live cells and possibly doublets in sizes ranging from about 10 microns to about 30 microns with a peak of about 16 microns, a sharp peak of dead cells in sizes between 8 and 9 microns and huge tail of cell debris in the smaller size range smaller than 8 microns.

FIG. 22 represents another histrogram of cell/particle sized measured by the same instrument on the sample from the top port effluent of the compact cell settler (208), showing an enhanced peak of dead cells in size between 8 and 9 microns, a tail of cell debris in the sizes smaller than 8 microns and dramatically a total absence of any peak for live cells about 16 microns. These size measurements strongly demonstrate that settler top effluent removes selectively the smaller dead cells and cell debris from the perfusion bioreactor (218), while the larger live cells are continuously returned to the perfusion bioreactor (218). This selective removal of smaller dead cells and cell debris has been demonstrated by us (Batt et al. 1990 and Searles et al. 1994) with inclined plate settlers. The present disclosure of compact cell settlers again reproduced those successive results in a more compact and more easily scalable design. None of the other cell retention devices available today for mammalian cells exhibit any such selectivity in removing only the smaller dead cells and cell debris.

Example 4: Vaccines, Viruses or Virus-like Particles Production

Production of vaccines, such as viruses or virus-like particles (VLPs), is usually carried out by infection and lysis of live mammalian or insect cells in a batch or fed-batch bioreactor culture. Viruses or virus-like particles are released from the infected cell in a lytic process after large intracellular production of these viruses or virus-like particles. With the large difference in the size (sub-micron or nanometer scale) of these particles compared to the size (about 5-20 microns) of live mammalian and insect cells, the separation of the viruses or virus-like particles from the bioreactor culture is very simple. By controlling the harvest or outlet rate of cell culture broth containing mostly viruses or VLPs, along with cell debris, it is possible to retain a smaller number of the infective particles inside the bioreactor along with the growing live cells to continually infect and produce vaccines in a continuous perfusion bioreactor attached to a settler device of this disclosure for continuous harvest of viruses and VLPs.

Example 5: Solid Catalyst Particle Separation and Recycle

Separation of a solid catalyst particle for recycle into the reactor and reuse in further catalyzing liquid phase chemical reactions, such as Fischer-Tropsch synthesis, has been demonstrated before with lamellar settlers (U.S. Pat. No. 6,720,358, 2001). Many such two-phase chemical reactions, involving solid catalyst particles in liquid or gas phase reactions can be enhanced by the particle settling devices of this disclosure, which presents a more compact particle separation device to accomplish the same solids separation and recycle as demonstrated with lamellar settlers.

Example 6: Plant and Algal Cell Harvesting

Recombinant plant cell cultures secreting valuable products, while not yet commercially viable, are yet another field of potential applications for the settling devices of this disclosure. Inclined settlers have been used in several plant cell culture applications. Such devices can be replaced by the more compact conical spiral settler devices of this disclosure. With the size of plant cells being much higher than those of yeast or mammalian cells, the cell separation efficiency will be much higher with single plant cells or plant tissue cultures.

A more immediate commercial application of the settler devices of this disclosure may be in the harvesting of algal cells from large scale cultivation ponds to harvest biodiesel products from inside algal cells. Relatively dilute algal cell mass in large (acre sized) shallow ponds converting solar energy into intracellular fat or fatty acid storage can be harvested easily through the conical spiral settler device of this disclosure, and the concentrated algal cells can be harvested from the bottom outlet.

Example 7: Municipal Waste Water Treatment

Large scale municipal waste water treatment plants (using activated sludge or consortia of multiple bacterial species for degradation of biological and organic waste in sewage or waste water) commonly use large settling tanks and more modern versions of these plants use lamellar settlers to remove the clarified water from the sludge. The conical spiral settler devices of this disclosure can be scaled up to the larger sizes required in these plants, while remaining smaller in size than the large settling tanks or lamellar settlers currently used in these treatment plants.

Example 8: Industrial Process Water Clarification

Large scale water treatment plants, cleaning either industrial waste water or natural sources of turbid water containing suspended solids, use large scale settling tanks or lamellar inclined settlers. These large scale devices can now be replaced with the more compact conical spiral settler devices of this disclosure to accomplish the same goal of clarifying water for industrial reuse or municipal supply of fresh water.

Example 9: Capture and Purification of Monoclonal Antibodies on Protein A Coated Beads Cell culture supernatants containing monoclonal antibodies can be contacted with protein A coated microspheres or beads (40-200 microns) inside our settler via two different inlets, e.g. beads coming in from a top inlet and the cell culture supernatant coming in via the bottom port to maximizing their contacting and capture efficiency. Capture of monoclonal antibodies on protein A beads is very quick, typically under 10 min. of residence time inside the competing affinity chromatography columns. The protein A coated microspheric beads will settle down fast and can be kept in suspension and well mixed contact with the cell culture supernatant by pumping it in from the bottom inlet. The depleted cell culture supernatants can be removed continuously from the top outlet of cell settler (208 of the present disclosure in a batch loading operation. Any beads entrained with upward flowing liquid will settle on the inclined surfaces and return to the bottom stirred region. After loading close to the maximum binding capacity of the add beads, beads can be washed with the typical washing solution of about 3-5× volume of the settler to remove all unbound host cell protein along with dead cells cell debris which are present in the supernatant via the top outlet.

After completing thorough washing, elution media will be pumped in slowly to remove the bound antibodies into the liquid medium and concentrated antibody solution is removed via the top port, while retaining the beads inside the settler. After elution is completed, equilibration of the beads is conducted by pumping in the equilibration solution from the bottom inlet, while the beads are held in suspension by this incoming solution. After equilibration, next batch of cell culture supernatant is loaded into the settler to repeat the above four-step process, similar to the sequence used in a chromatography column. Some advantages of using the cell settler devices of the present disclosure for monoclonal antibody capture are that: (i) cell culture supernatant can be directly loaded to contact with the protein A beads, without the need for removing dead cells or cell debris commonly present in the supernatant; and (ii) more efficient immediate contacting of all the suspended beads with in the incoming supernatant, rather than the gradual or delayed exposure of monoclonal antibodies to the fixed bed of beads in the later parts of the column.

Example 10: Decanter/Cell Settler for In Situ Extraction of Secreted Organic Products from Yeast or any Other Cells into an Organic Layer Production and secretion of several fragrance and flavor compounds are being metabolically engineered into microbial yeast cells, such as *Saccharomyces cerevisiae*. Some of these compounds may be more toxic to the cells and can be extracted readily into an organic liquid to reduce the cellular toxicity as well as to increase the productivity of the yeast cells. Emulsions of organic liquid containing the secreted product and aqueous layer containing the productive microbial cells from the stirred tank bioreactor can be pumped into the inlet port (131) of the compact cell settler. Inside the quiet zones of the settler, the emulsion is separated easily into the organic layer floating on top and harvested via the top port (133) and aqueous layer containing the live and productive cells settling to the bottom and recycled to the bioreactor via bottom port (132). Any cellular debris will fractionate into the organic layer and easily removed from the top of settler. Live and productive cells in the aqueous layers are returned to the bioreactor to increase the cell densities and productivity inside the perfusion bioreactor.

Example 11: In Vitro Expansion of Various Mammalian Cells, Such as Stem Cells and CAR-T Cells for Autologous Cell Therapy in Our Compact Cell Settler that can be Used as a Stand-alone Perfusion Bioreactor Currently, the field of in vitro expansion of various mammalian cells such as stem cells and CAR-T cells is expanding rapidly with sterile single-use disposable culture bags as the bioreactors placed on rocking platform for mixing or inside a $CO_2$ incubator for pH control. Such bag bioreactors are increasingly operated in continuous perfusion mode to remove the accumulated waste metabolic by-products, such as ammonia and lactate, using microfiltration membranes as cell retention devices on the bag to maintain high cell viability during the expansion. However, during the prolonged perfusion operation, dead cells and cell debris accumulate in these bags and cannot be removed through the microfiltration membranes on the bag. The cell settler devices of this disclosure can be operated effectively as a stand-alone, air-lift bioreactors, operated in a continuous perfusion to bring in fresh nutrient and remove metabolic waste products, as well as to remove selectively any dead cells and cell debris. The bottom port can be used as an inlet for controlled mixture of multiple gases $CO_2$, $O_2$ and $N_2$ to maintain the desired pH and DO in the bioreactor. The rising air through the central portion entrains or carries up some cell culture liquid, provides a gentle mixing of the nutrients in the bioreactor, and exits at the top outlet, while the liquid is disengaged in the cylindrical portion of settler and is recycled over the conical settlers. The returning cell culture liquid can be sampled for continuous measurements of pH, DO, for inputs into computer controlling the inlet gas mixture and occasional sampling for cell density and viability as desired. After the desired cell expansion, concentrated live cells are collected via the bottom port by switching the gas flow to a cell collection bag. The major advantage of our cell settler/bioreactor is that it provides for a facile removal of dead cells and cell debris along with toxic metabolic waste by-products, resulting in a high cell density of live cells after in vitro expansion for autologous cell therapy.

Example 12: Continuous Separation of Precipitated and Concentrated Therapeutic Proteins Several therapeutic proteins (e.g. insulin analog glargine and monoclonal antibodies) can be precipitated by adding simple salts (e.g. zinc chloride for glargine, or ammonium sulfate for antibodies), adjusting pH, and other solvents (e.g. m-cresol or other phenolics for glargine and ethanol for antibodies). This precipitation is a low-cost alternative to chromatography in the downstream purification processes for these therapeutic proteins. Currently, these precipitation steps are carried out in the batch mode, followed by centrifugation or decantation to remove the supernatant from the precipitant.

Using the separation devices of the present disclosure, a continuous separation process may be implemented. The protein rich harvest medium (after removing any cells by micro filtration or centrifugation or other methods) is input into a compact cell settler of this disclosure, along with other required chemicals, such as solvents, or salts in a pH-modifying solution, such as NaOH or HCl. The precipitation process will occur inside the settler and the protein-rich precipitant can be continuously removed in the bottom outlet, away from the protein-depleted supernatant, which is removed continuously from the top outlet.

Example 13: Ex Vivo Expansion of Mesenchymal Stromal/Stem Cells (MSCs) on Microcarrier Beads and Purification of Expanded Stem Cells MSCs are capable of ex vivo expansion in the presence of suitable growth medium and are commonly grown attached to surfaces, such as tissue culture flasks, petri dishes, roller bottles, cell cubes, and microcarrier beads. Attached growth on microcarrier beads (size ranging from 100 microns to 500 microns) is very easily scalable as they are suspended in stirred or agitated bioreactors, controlled for optimal growth conditions such as pH, temperature, dissolved oxygen concentration and nutrient concentrations. However, separation of expanded stem cells from the microcarriers is a challenge, requiring enzymatic detachment, washing off excess enzyme quickly, and separating the stem cells from microcarrier beads. These different steps are currently attempted using labor-intensive and contamination-prone batch processing steps. Each of these difficult steps can be accomplished more easily in the bioreactor/cell sorter device shown in FIG. 14B which includes sensor probes (170) positioned within the cyclone housing (160). In one embodiment, the sensor probes comprise fluorescent probes to measure one or more of pH, dissolved oxygen (DO), glucose concentrations, temperature, and $CO_2$ levels within the cyclone housing. More specifically, with the settler device illustrated in FIG.

14B: (i) the excess enzyme is very easily washed or removed via the top port (155) by feeding in fresh nutrient medium via the bottom port (154) while the slower-setting detached cells and fast-settling, freshly denuded microcarrier beads are held in circulation inside the settler, (ii) bare microcarrier beads (100-500 microns) will settle much faster than the stem cells (10-20 microns) and can be removed from the bottom port (154) while the stem cells are circulated in suspension, and (iii) finally the expanded stem cells can be harvested via the bottom port (154) at the desired concentration for subsequent cell therapy applications.

Example 14: Co-culture of Stromal Cells on Microcarrier Beads to Secrete the Necessary Growth Factors to Support the In Vitro Expansion or Growth of Other Differentiated Cells, Such as T-lymphocytes or Cardiomyocytes Growth and differentiation of pluripotent stem cells into cardiomyocytes or activated lymphocytes (CAR-T cells) require expensive growth factors to be supplemented to the growth bioreactor. This cost can be reduced by co-culturing the desired cells with engineered mesenchymal stem cells (MSCs) that secrete the desired growth factors into the growth medium. These growth factor secreting cells support the growth of other desired cells, such as CAR-T cells, cardiomyoctyes, etc. This co-culture can be effected inside the bioreactor/cell sorter combination devices of this disclosure, and the cost of production or expansion of such cells is significantly reduced. The expanded cells can be easily removed from the co-culture by feeding in fresh medium at a required flow rate to remove the expanded single cells or cell aggregates, while keeping larger, microcarrier beads inside the bioreactor/cell settler.

Example 15: Fractionation or Sorting of any Mixed-cell Population, Such as from Bone Marrow, into Several Distinct Sub-populations with Desirable or Undesirable Characteristics After loading the bioreactor/cell sorter device of the present disclosure with some initial bolus of a mixed cell population (such as bone marrow cells), we can feed in fresh nutrient medium at slow, step-wise increasing flow rates, such that the smallest cells (e.g. platelets, red blood cells, etc.) leave via top effluent stream at the lowest flow rates, followed by bigger cell types (lymphocytes, mononuclear cells, etc.) at increasingly higher flow rates, and then by the biggest cell types (such as macrophages, megakaryocytes, etc.) at the highest flow rates. By increasing the nutrient feed and the top effluent flow rates at slowly-increasing step-wise flow rates, relatively pure populations of a single desired cell type is obtained leaving the bioreactor/cell sorter device in a healthy cell culture growth medium so they can be propagated further for subsequent use.

Example 16: In Vitro Production of Universal Red Blood Cells

Novel genetic engineering methods are under development for directed differentiation of hematopoietic stem cells into erythroid cell lineage. Proerythroblast cells, the earliest committed stage in erhthropoiesis, are rather large (12-20 microns), up to three times larger than a normal erythrocyte. Polychromatophilic normoblasts, the subsequent stage in erythroid lineage, is smaller (12-15 microns) than the proerythroblast cells. Orthochromatophilic normoblast cells, the nucleated erythroid precursor cells, are still smaller (8-12 microns), followed by the still smaller mature enucleated red blood cells. (Geiler, C., Andrade, I., Clayton, A., and Greenwald. D. 2016, Genetically engineered in vitro erythropoiesis, International Journal of Stem Cells, 9: 53-59). Based on size fractionation capabilities of the bioreactor/cell sorter devices of this disclosure, all the larger precursor cells are retained, and only the smallest mature enucleated red blood cells are removed from the top effluent of the device, while all the larger precursor cells are continually expanding inside the bioreactor/cell sorter device.

Example 17: Large-scale Platelet Production

Ex vivo expansion of high-ploidy megakaryocytic cells in controlled bioreactor culture conditions and their shearing off into smaller platelet cells is increasingly understood at a fundamental level (Panuganti, S., Schlinker, A. C., Lindholm, P. F., Papoutsakis, E. T., and Miller, W. M. 2013, Three-stage ex vivo expansion of high-ploidy megakaryocytic ells: Toward large-scale platelet production, Tissue Engineering Part A, 19: 998-1014). As this understanding develops further, these necessary culture parameters can be obtained and controlled inside these bioreactor/cell sorter devices for growth and differentiation of megakaryocytic cells, while harvesting only the mature, sheared off smaller platelets via the top outlet from the settler.

To provide additional background, context, and to further satisfy the written description requirements of 35 U.S.C. § 112, the following references are incorporated by reference herein in their entireties: U.S. Pat. No. 5,624,580, U.S. Patent App. Pub. 2009/159523, U.S. Patent App. Pub. 2011/097800, U.S. Patent App. Pub. 2012/180662, U.S. Patent App. Pub. 2014/011270.

The foregoing examples of the present disclosure have been presented for purposes of illustration and description. These examples are not intended to limit the disclosure to the form disclosed herein. Consequently, variations and modifications commensurate with the teachings of the description of the disclosure, and the skill or knowledge of the relevant art, are within the scope of the present disclosure. The specific embodiments described in the examples provided herein are intended to further explain the best mode known for practicing the disclosure and to enable others skilled in the art to utilize the disclosure in such, or other, embodiments and with various modifications required by the particular applications or uses of the present disclosure. It is intended that the appended claims be construed to include alternative embodiments to the extent permitted by the prior art.

What is claimed is:

1. A particle settling device comprising:
    a cyclone housing including:
        a first conical portion;
        a second conical portion;
        a cylindrical portion located between the first and second conical portions;
        at least one inlet for introducing liquids into the cyclone housing;
        a first outlet port in the first conical portion for harvesting a clarified liquid;
        a second outlet port in the second conical portion for harvesting a concentrated liquid;
        a sensor to measure dissolved $CO_2$ ($pCO_2$) within the cyclone housing, the sensor positioned in one of the second conical portion and a line interconnected to the second outlet port; and a first stack of cones located within the cyclone housing and occupying the first conical portion and at least part of the cylindrical portion, each cone of the first stack of cones including a truncated apex and an open base, the truncated apex of each cone being oriented towards one of the first outlet port and the second outlet port, wherein the truncated apex of each cone defines a substantially central opening.

2. The device of claim 1, wherein the sensor is further operable to measure at least one of pH, dissolved oxygen (DO), and glucose within the cyclone housing.

3. The device of claim 1, wherein the cyclone housing is formed of a plastic.

4. The device of claim 1, wherein at least one cone in the first stack of cones consists entirely of a plastic.

5. The device of claim 1, wherein an angle of inclination for a surface of a cone in the first stack of cones is between about 30 degrees to about 60 degrees from vertical.

6. The device of claim 1, wherein at least one surface of a cone in the first stack of cones is coated with a silicone.

7. The device of claim 1, wherein the at least one inlet is positioned below the first stack of cones of the cyclone housing.

8. The device of claim 1, wherein the at least one inlet is associated with the second conical portion of the cyclone housing.

9. The device of claim 1, wherein the first outlet port is configured as a liquid harvest outlet formed at an apex of the first conical portion at an uppermost portion of the cyclone housing, the first outlet port in liquid communication with an interior and an exterior of the cyclone housing.

10. The device of claim 1, wherein each cone of the first stack of cones is spaced from an interior surface of the cyclone housing.

11. The device of claim 1, wherein the sensor is positioned in the second conical portion.

12. The device of claim 1, wherein the sensor comprises a fluorescent probe, and wherein at least a portion of the second conical portion proximate to the sensor is transparent or translucent.

13. The device of claim 1, wherein the second conical portion is transparent or translucent.

14. A method of settling particles in a suspension, comprising:
    (a) introducing a liquid suspension of particles into a particle settling device which includes a cyclone housing having:
        a first conical portion;
        a second conical portion;
        a cylindrical portion located between the first and second conical portions;
        at least one inlet for the liquid suspension to enter the cyclone housing;
        a first port for harvesting a clarified liquid;
        a second port for discharging a concentrated liquid suspension;
        a sensor to measure dissolved $CO_2$ ($pCO_2$) within the cyclone housing, the sensor positioned in one of the second conical portion and a line interconnected to the second port; and
        a first stack of cones located within the cyclone housing and occupying the first conical portion and at least part of the cylindrical portion, each cone of the first stack of cones including (i) a truncated apex, and (ii) an open base, wherein the truncated apex of each cone is oriented toward one of the first conical portion and the second conical portion, wherein the truncated apex of each cone defines a substantially central opening;
    (b) collecting the clarified liquid from the first port; and,
    (c) collecting the concentrated liquid suspension from the second port.

15. The method of claim 14, wherein the liquid suspension comprises at least one of a recombinant cell suspension, an alcoholic fermentation, a suspension of solid catalyst particles, a municipal waste water, and industrial waste water.

16. The method of claim 14, wherein the liquid suspension comprises at least one of mammalian cells, bacterial cells, yeast cells and plant cells.

17. The method of claim 14, wherein the liquid suspension comprises at least one of algae cells, plant cells, mammalian cells, murine hybridoma cells, stem cells, CAR-T cells, red blood precursor and mature cells, cardiomyocytes, yeast in beer, and eukaryotic cells.

18. The method of claim 14, wherein the liquid suspension comprises recombinant microbial cells selected from at least one of *Pichia pastoris, Saccharomyces cerevisiae, Kluyveromyces lactis, Aspergillus niger, Escherichia coli*, and *Bacillus subtilis*, and wherein the clarified liquid includes secreted proteins or enzymes.

19. The method of claim 14, wherein the liquid suspension comprises one or more of microcarrier beads, affinity ligands, and surface activated microspherical beads.

20. The method of claim 14, wherein introducing a liquid suspension comprises directing the liquid suspension from a plastic disposable bioreactor bag into the particle settling device.

21. The method of claim 14, wherein the clarified liquid collected comprises at least one of biological molecules, organic or inorganic compounds, chemical reactants, and chemical reaction products.

22. The method of claim 14, wherein the clarified liquid collected comprises at least one of hydrocarbons, polypeptides, proteins, alcohols, fatty acids, hormones, carbohydrates, antibodies, glycoproteins, terpenes, isoprenoids, polyprenoids, and beer.

23. The method of claim 14, wherein the clarified liquid collected comprises at least one of biodiesel, insulin, brazzein, antibodies, growth factors, colony stimulating factors, and erythropoietin (EPO).

24. The method of claim 14, further comprising:
    removing dead cells from the cyclone housing through the first port, wherein the first port is formed through an uppermost portion of the first conical portion; and introducing a nutrient medium into the cyclone housing through the second port.

25. The method of claim 14, wherein the sensor comprises a fluorescent probe, and wherein the sensor is further operable to measure at least one of pH, dissolved oxygen (DO), and glucose.

26. The method of claim 14, further comprising introducing at least one of $O_2$, $CO_2$, and $N_2$ into the cyclone housing to alter a pH level and a concentration of dissolved oxygen within the cyclone housing.

27. The method of claim 14, further comprising using data received from the sensor to adjust one or more of pH, dissolved oxygen concentration, and $pCO_2$ within the cyclone housing.

* * * * *